United States Patent [19]

Kriesel et al.

[11] Patent Number: 5,328,464
[45] Date of Patent: Jul. 12, 1994

[54] CLOSED DRUG DELIVERY SYSTEM

[75] Inventors: Marshall S. Kriesel, Saint Paul; Thomas Thompson, Richfield, both of Minn.

[73] Assignee: Science Incorporated, Bloomington, Minn.

[21] Appl. No.: 34,908

[22] Filed: Mar. 19, 1993

Related U.S. Application Data

[63] Continuation-in-part of Ser. No. 870,553, Apr. 17, 1992, which is a continuation-in-part of Ser. No. 513,917, Apr. 24, 1990, Pat. No. 5,122,116.

[51] Int. Cl.⁵ .............................. A61M 37/00
[52] U.S. Cl. .............................. 604/83; 604/84; 604/85; 604/88; 604/89; 604/122; 604/132; 604/247; 604/248; 604/406; 604/414; 604/415; 604/416; 604/890.1; 128/DIG. 12
[58] Field of Search ............ 604/83, 84, 85, 88, 604/89, 90, 122, 249, 132, 406, 416, 415, 414, 890.1, 247; 128/DIG. 12

[56] References Cited

U.S. PATENT DOCUMENTS

| 3,469,578 | 9/1969 | Bierman | 604/246 |
| 5,019,047 | 5/1991 | Kriesel | 604/131 |
| 5,122,116 | 6/1992 | Kriesel et al. | 604/249 |
| 5,169,389 | 12/1992 | Kriesel | 604/132 |
| 5,205,820 | 4/1993 | Kriesel | 604/85 |
| 5,236,418 | 8/1993 | Kriesel | 604/85 |

Primary Examiner—C. Fred Rosenbaum
Assistant Examiner—Mark Bockelman
Attorney, Agent, or Firm—J. E. Brunton

[57] ABSTRACT

An apparatus for controllably intermixing two or more components in a sterile, closed environment to produce a flowable substance and then for expelling the flowable substance from the apparatus at a precisely contolled rate. The apparatus is particularly useful for medical applications and includes a dispenser portion with its own stored energy element provided in the form of an elastomeric membrane and a coupling mechanism for coupling a drug vial to the dispenser portion for controlled mixing a medicament contained within the drug vial with a diluent stored within the dispenser portion of the apparatus via a sterile pathway.

30 Claims, 27 Drawing Sheets

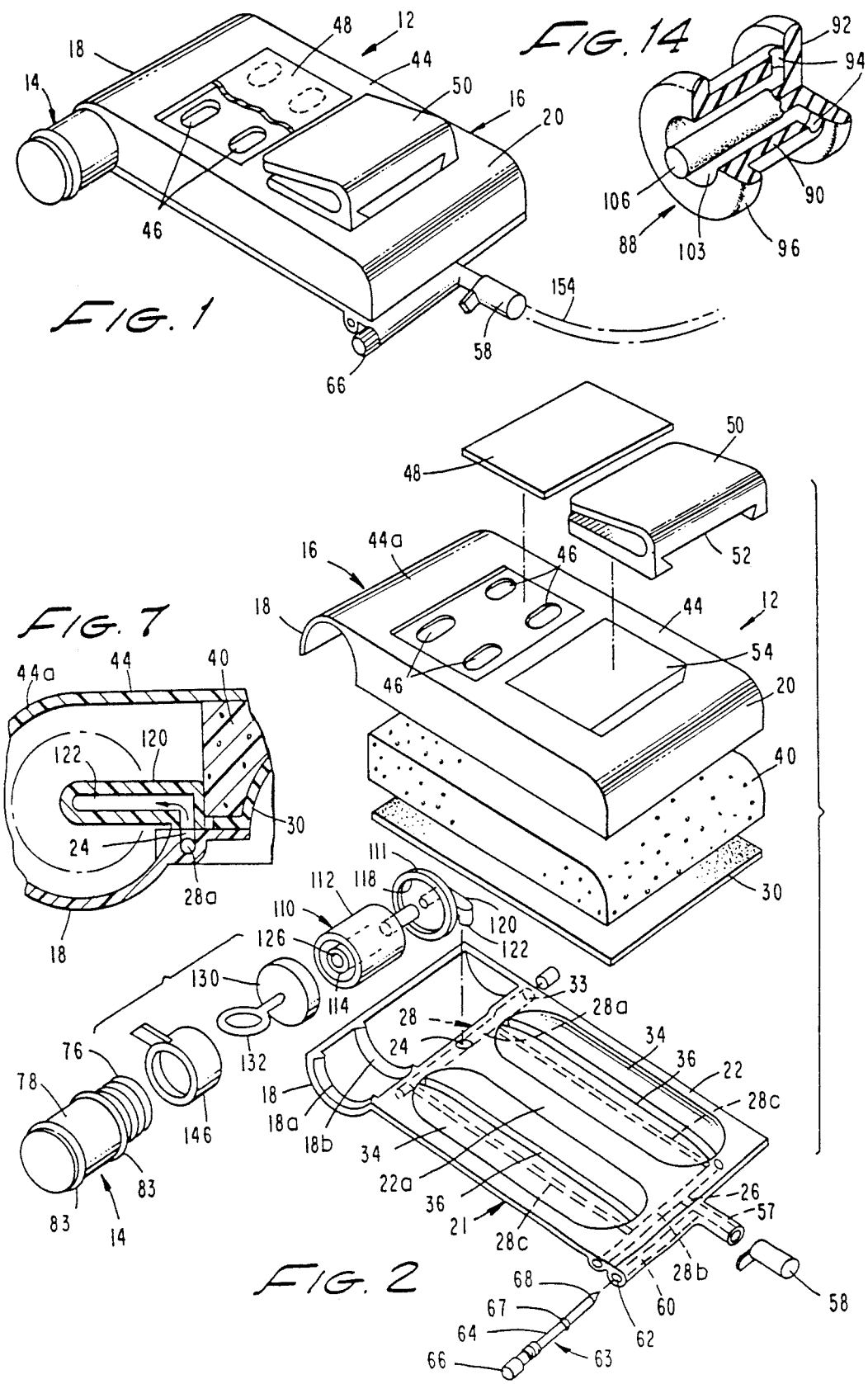

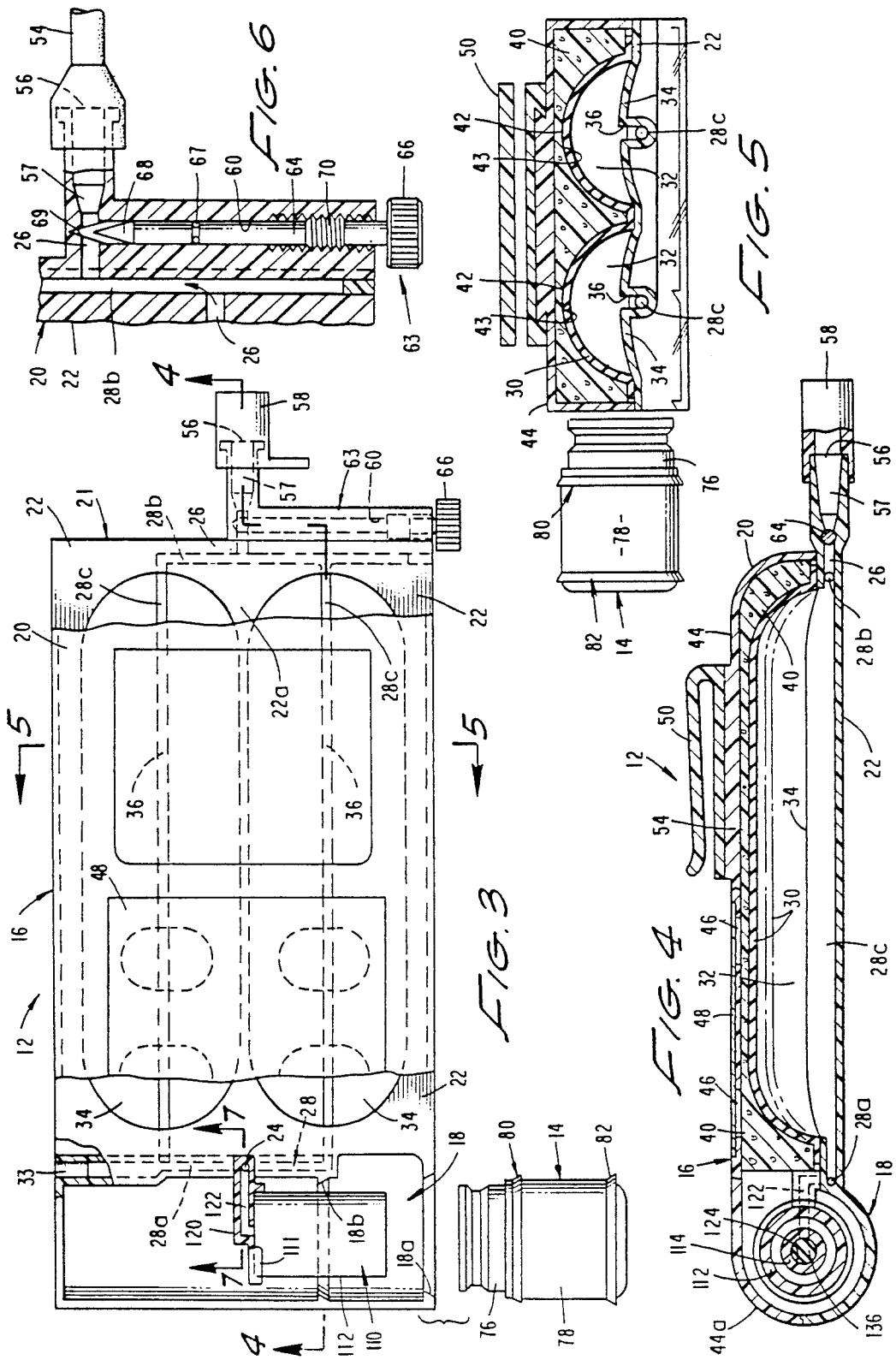

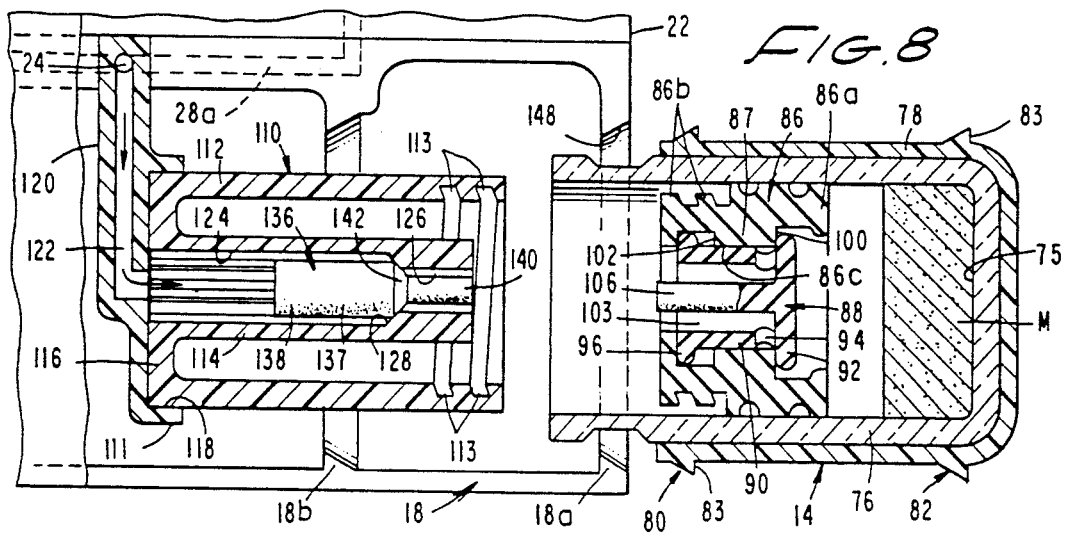
FIG. 8
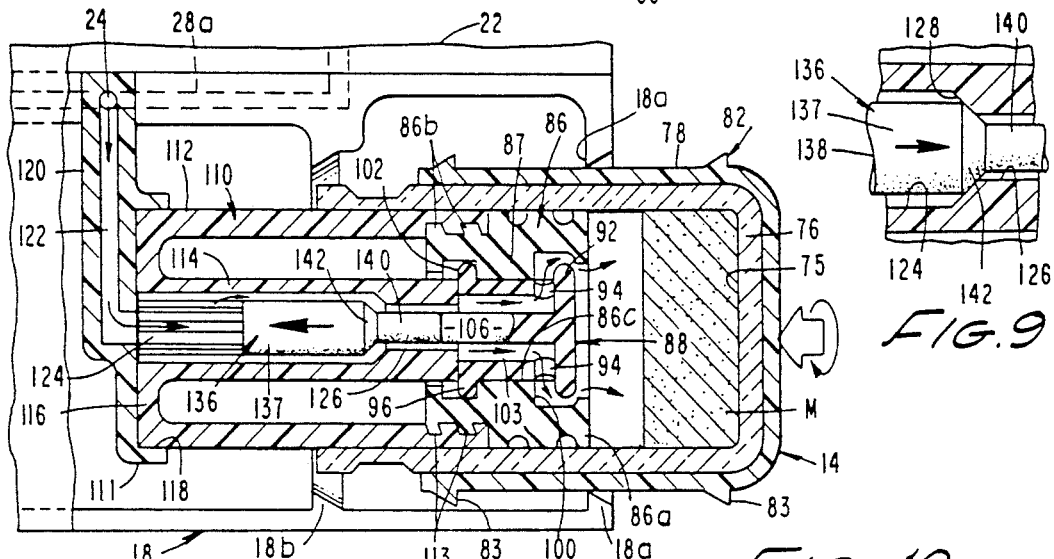
FIG. 9
FIG. 10
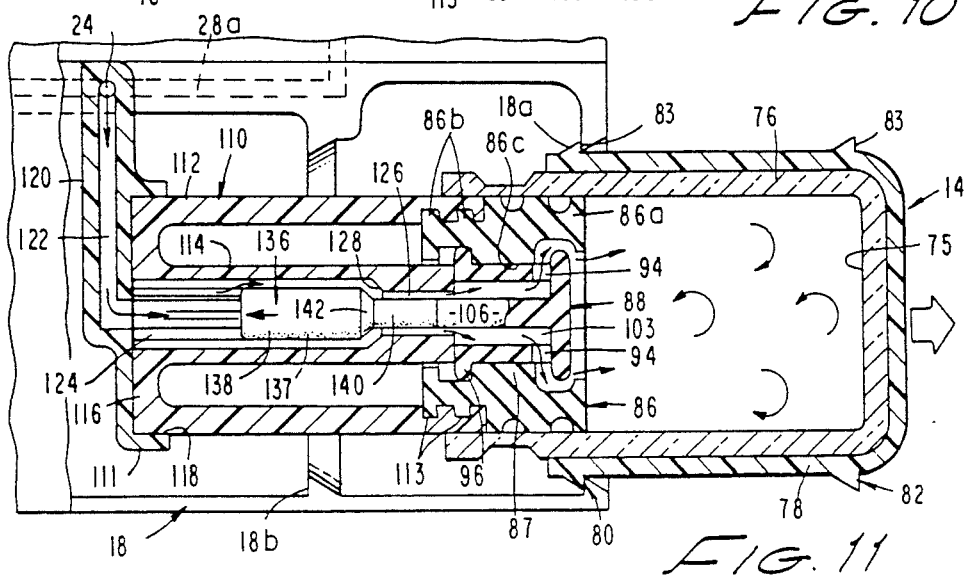
FIG. 11

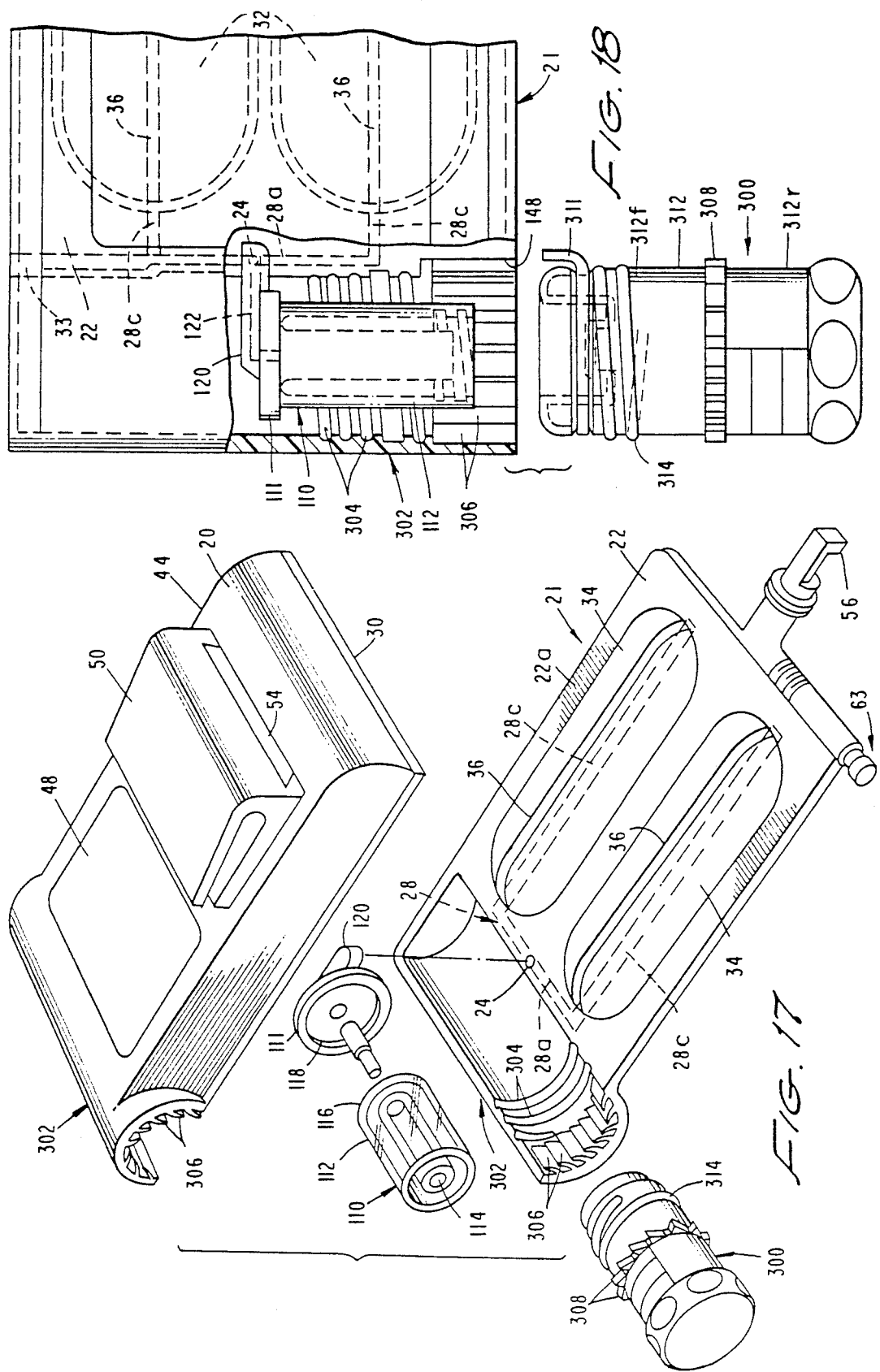

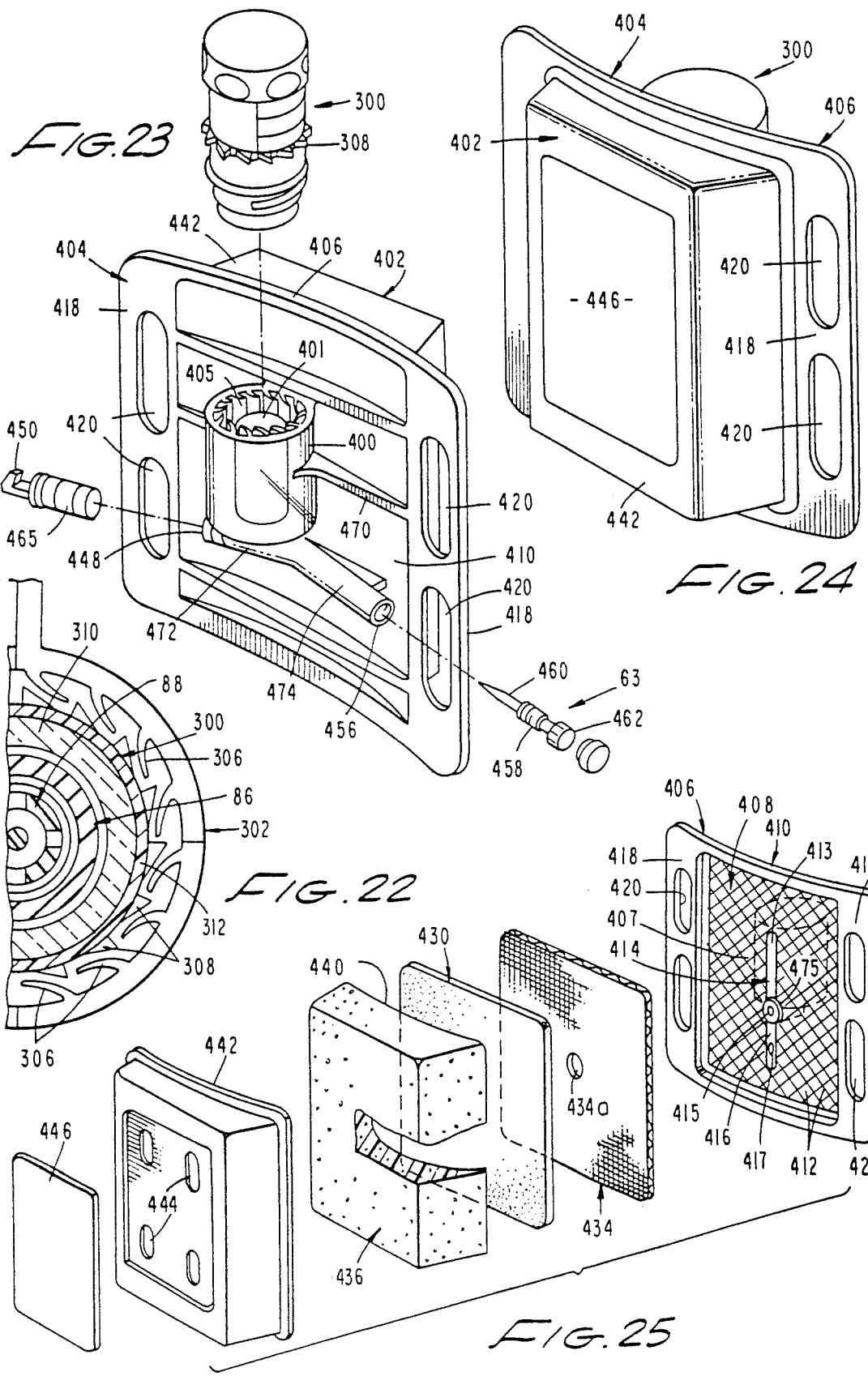

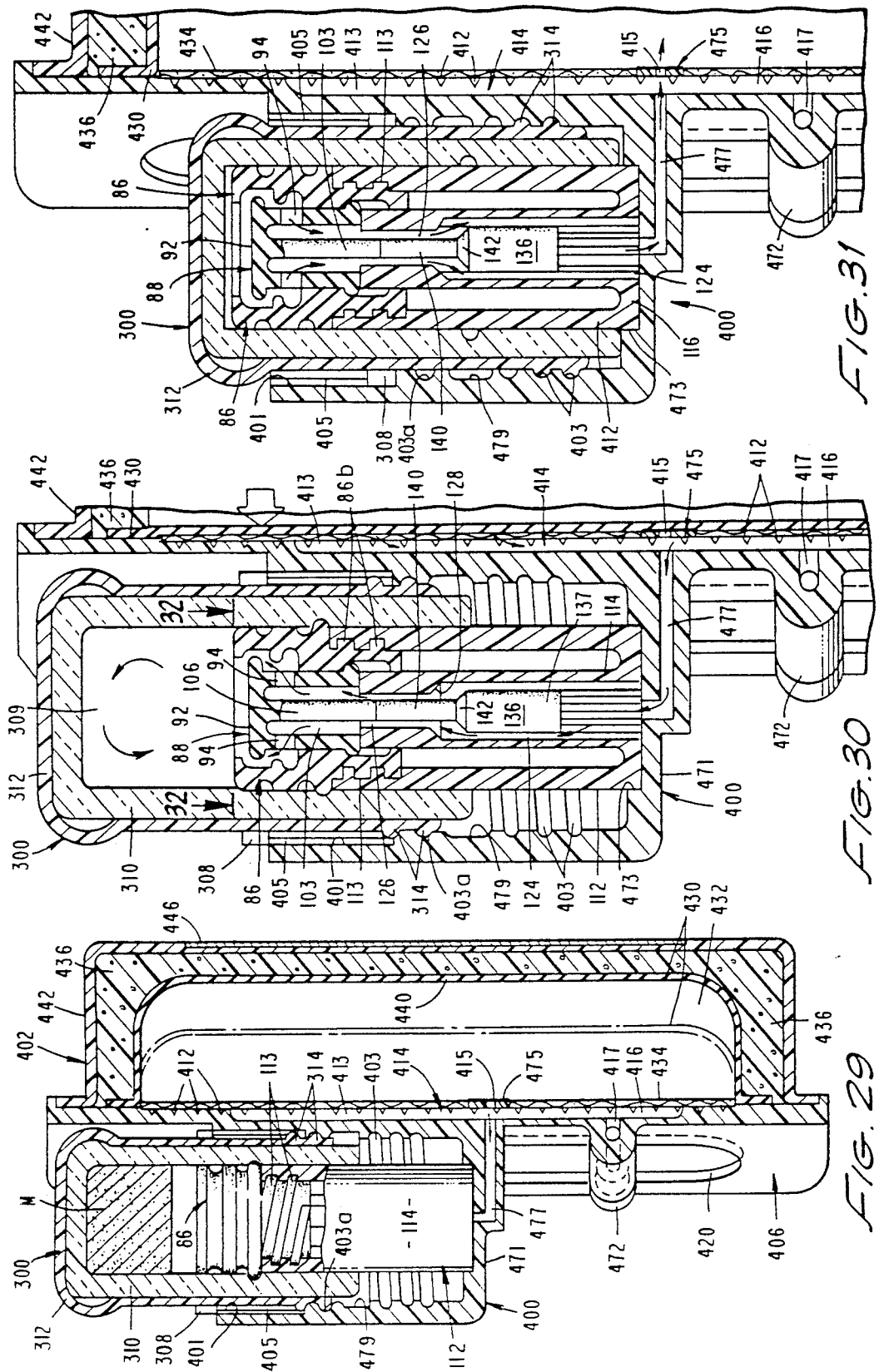

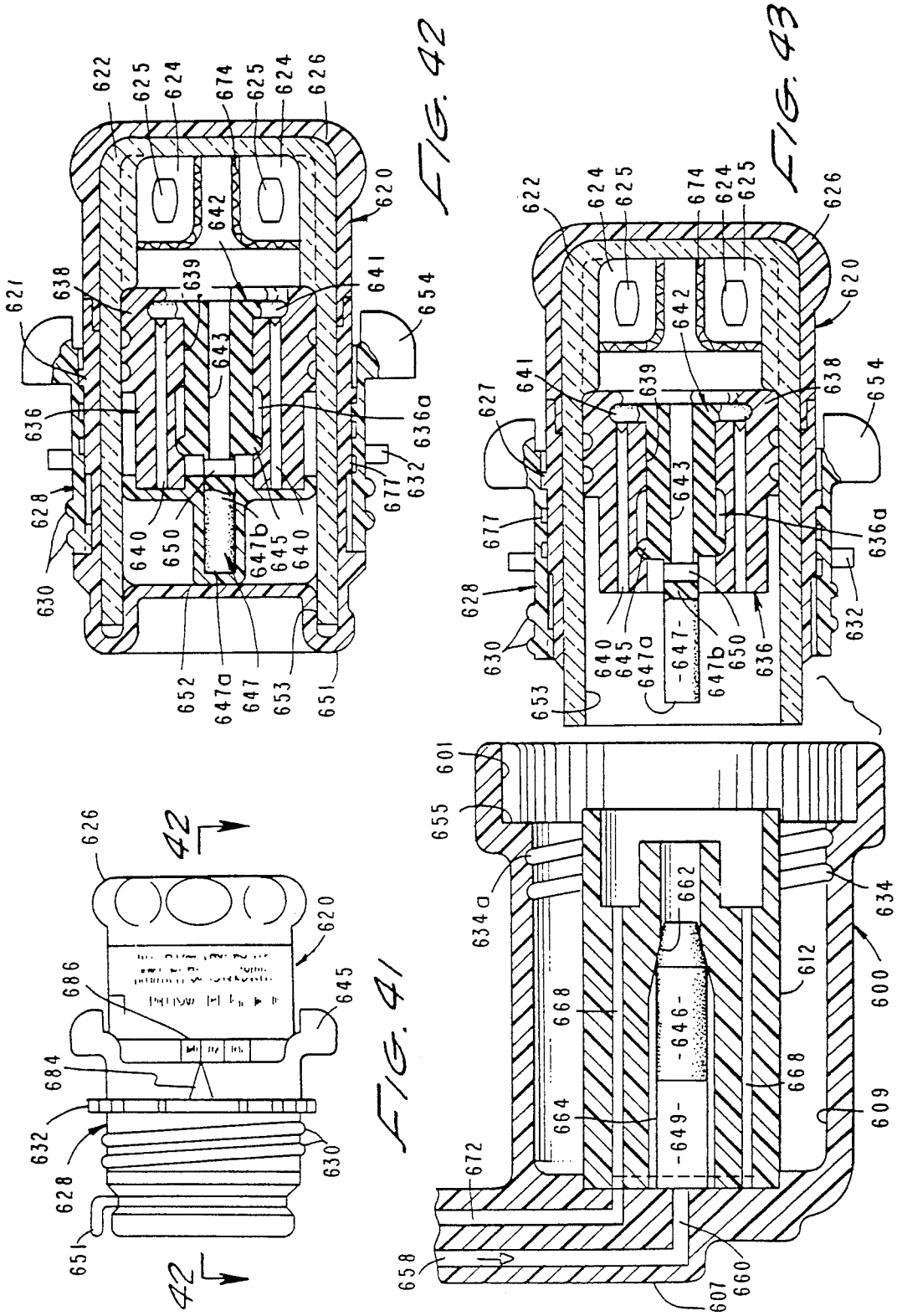

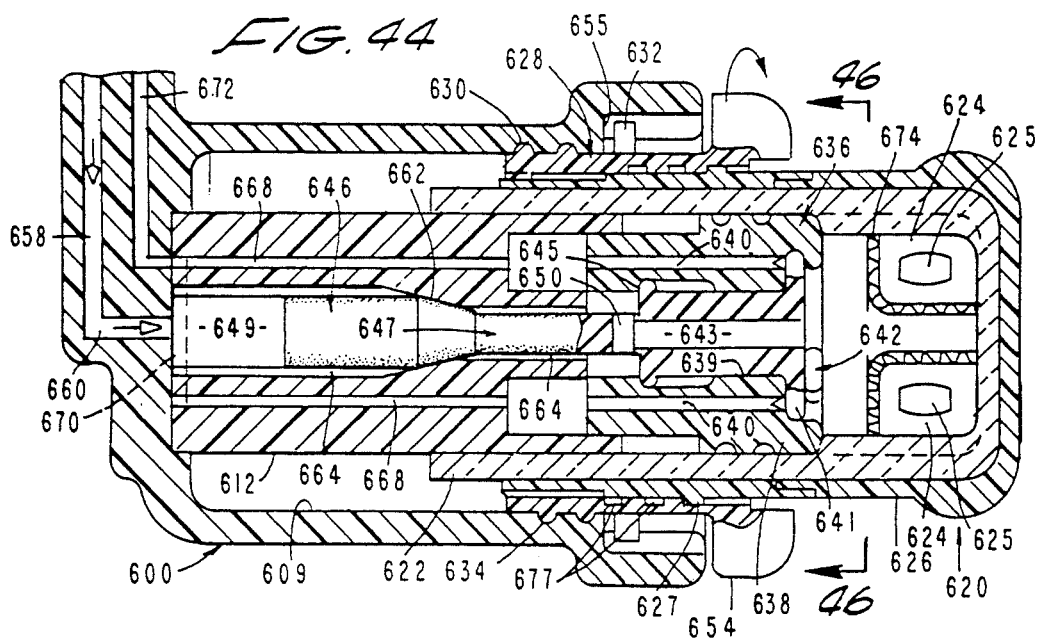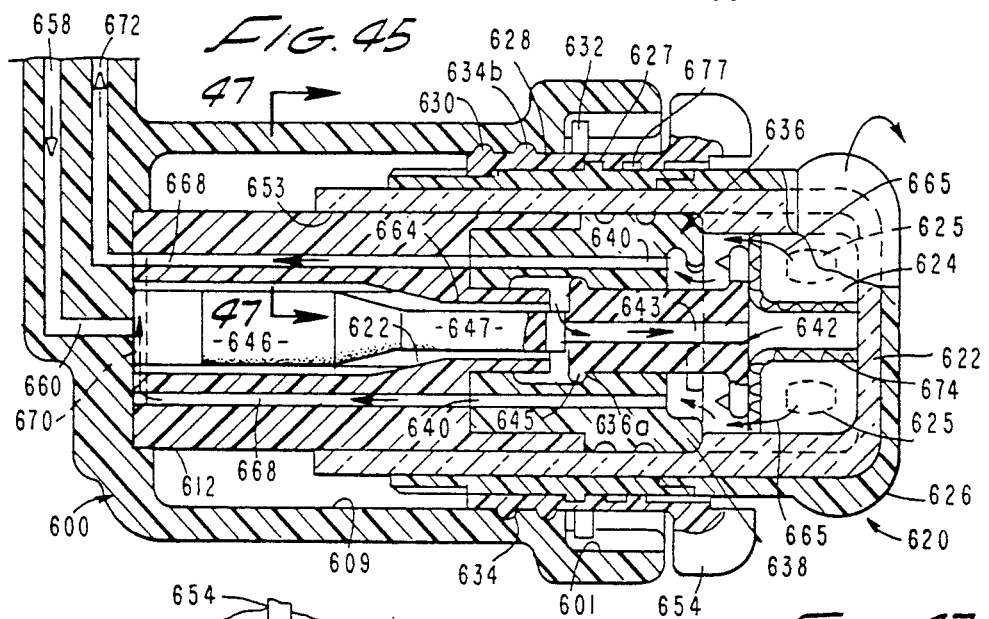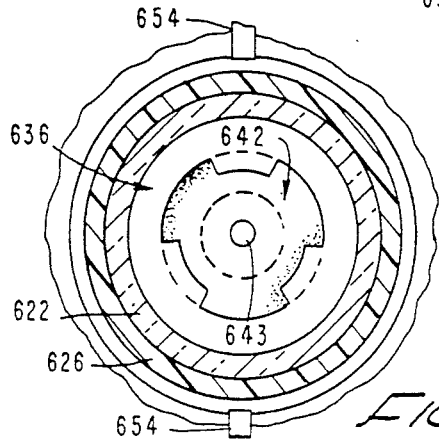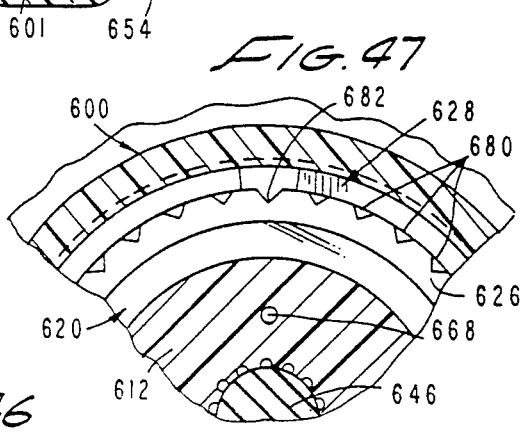

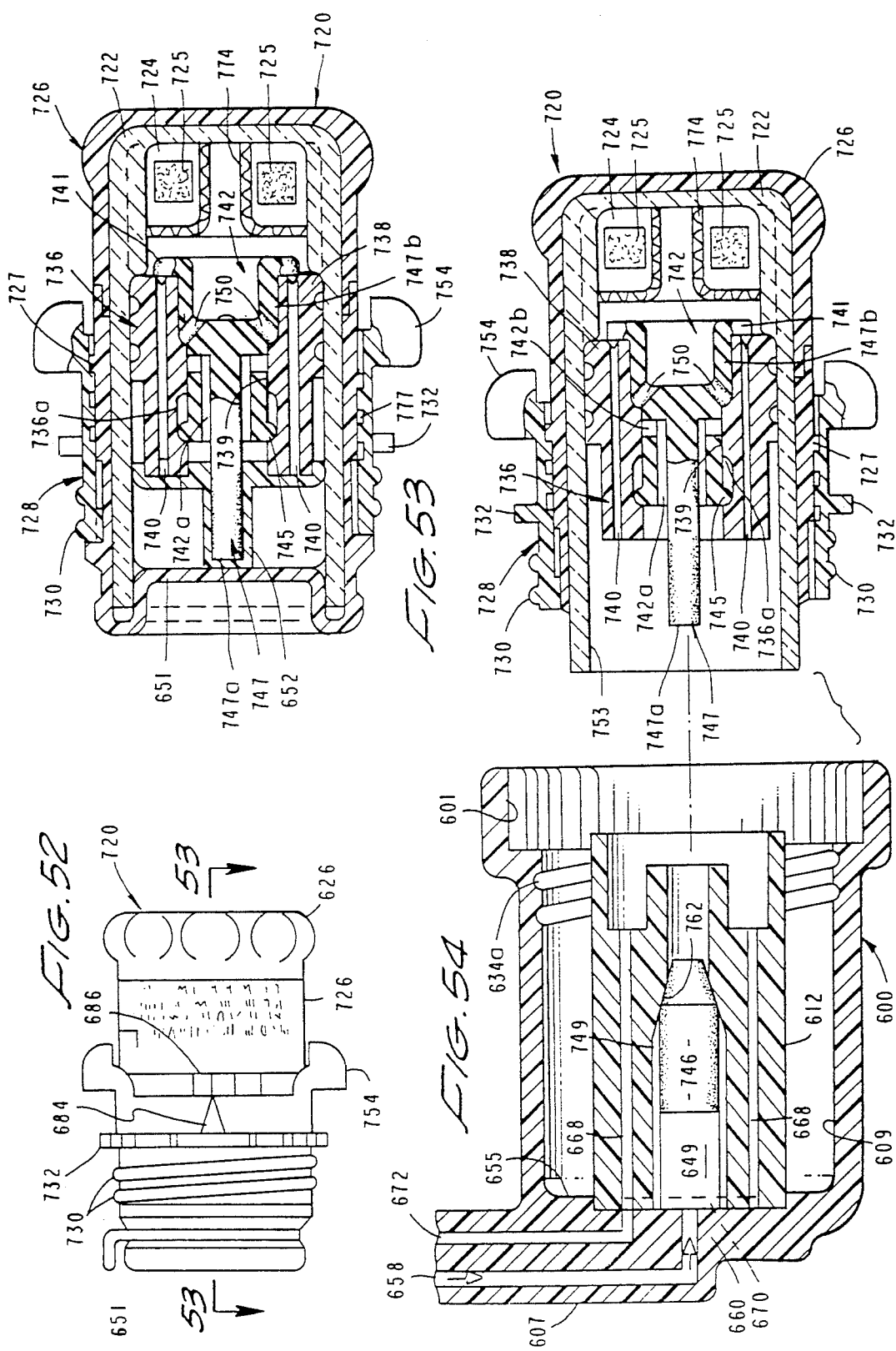

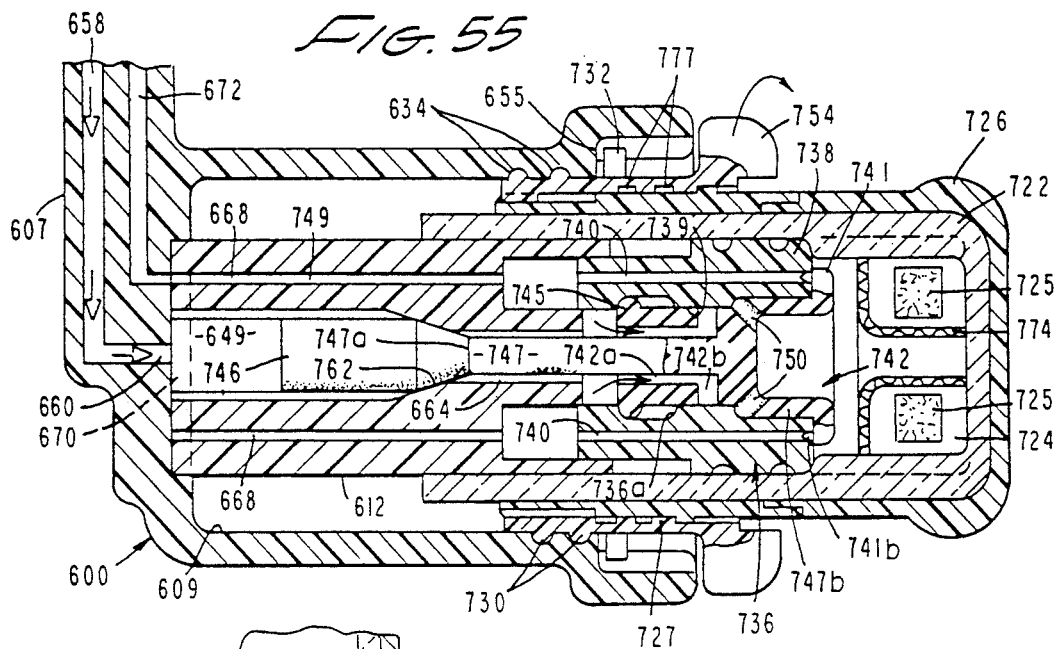
FIG. 55
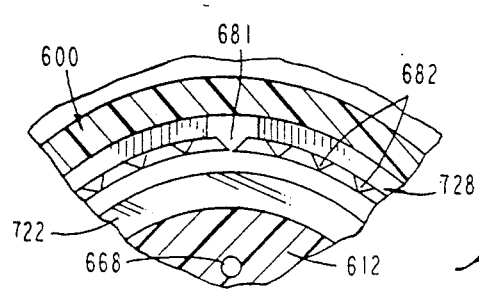
FIG. 62
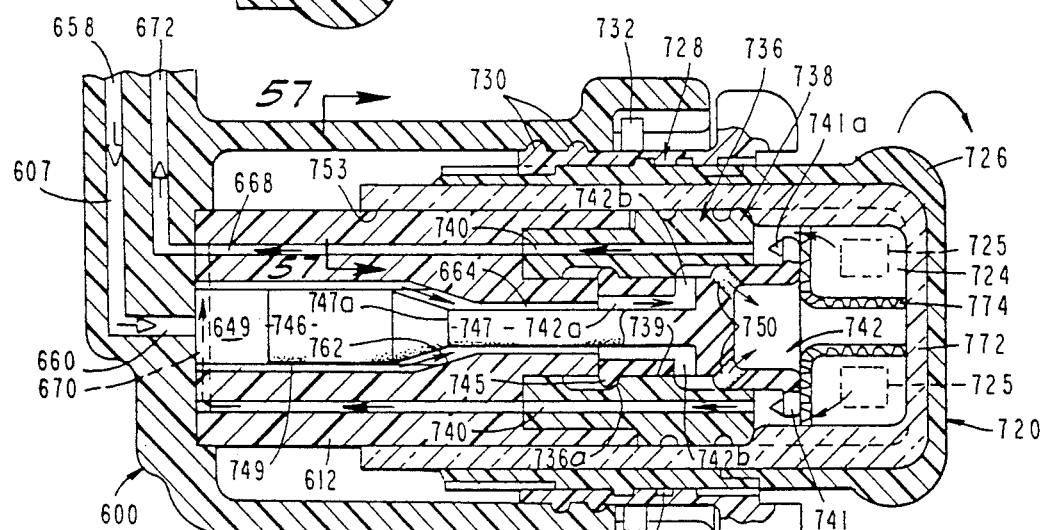
FIG. 56
FIG. 57

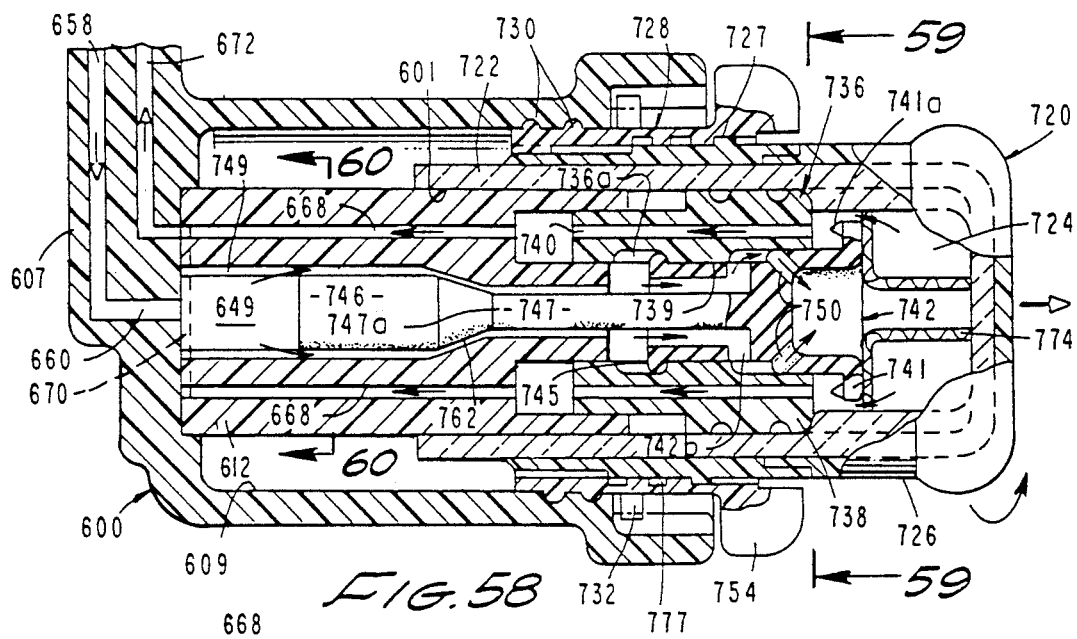
FIG. 58
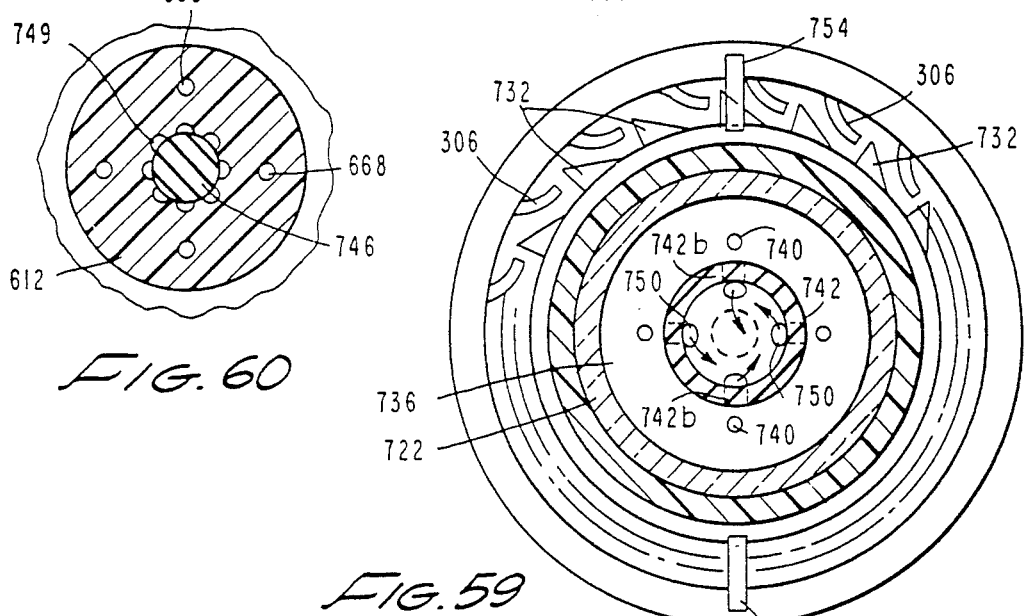
FIG. 60
FIG. 59
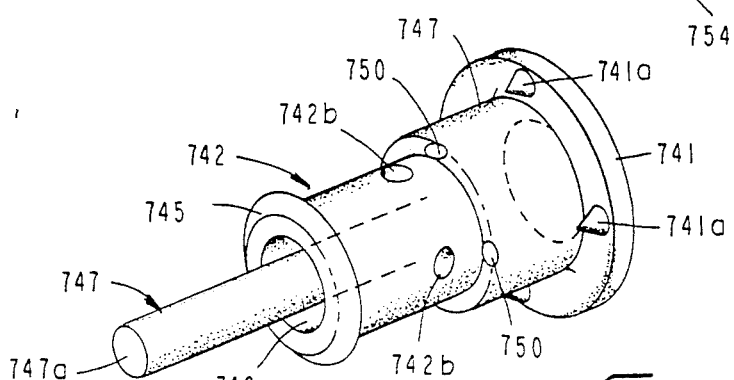
FIG. 61

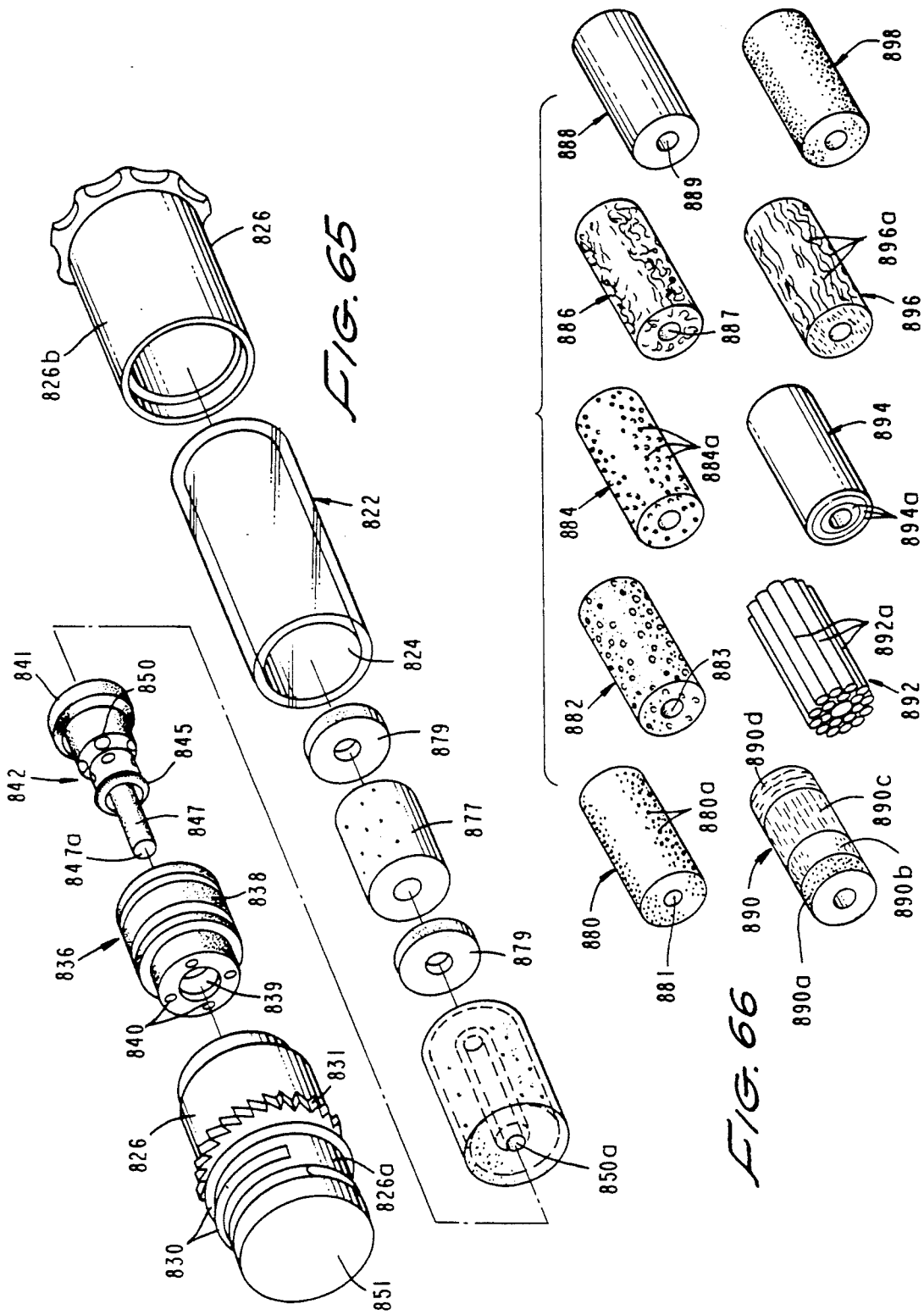

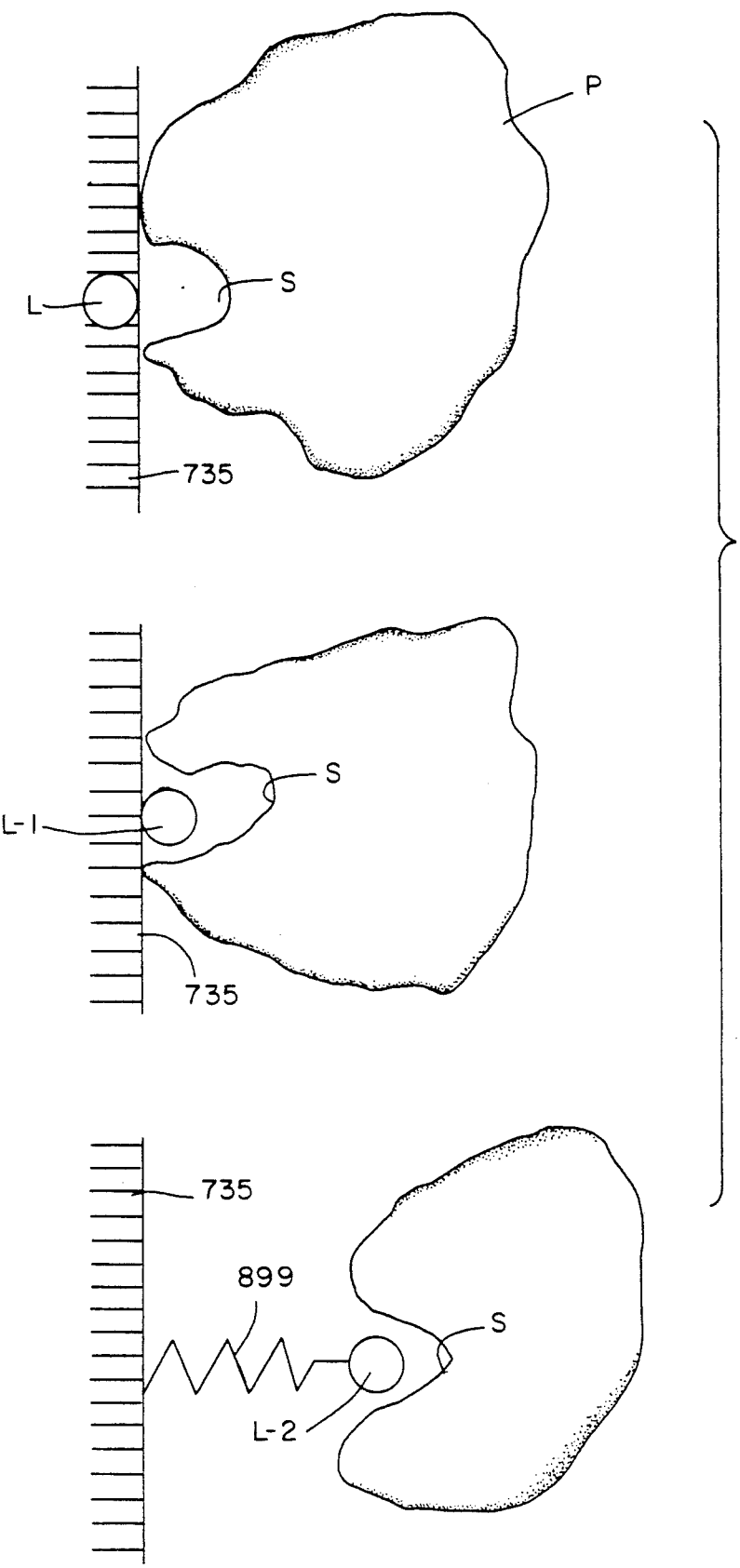

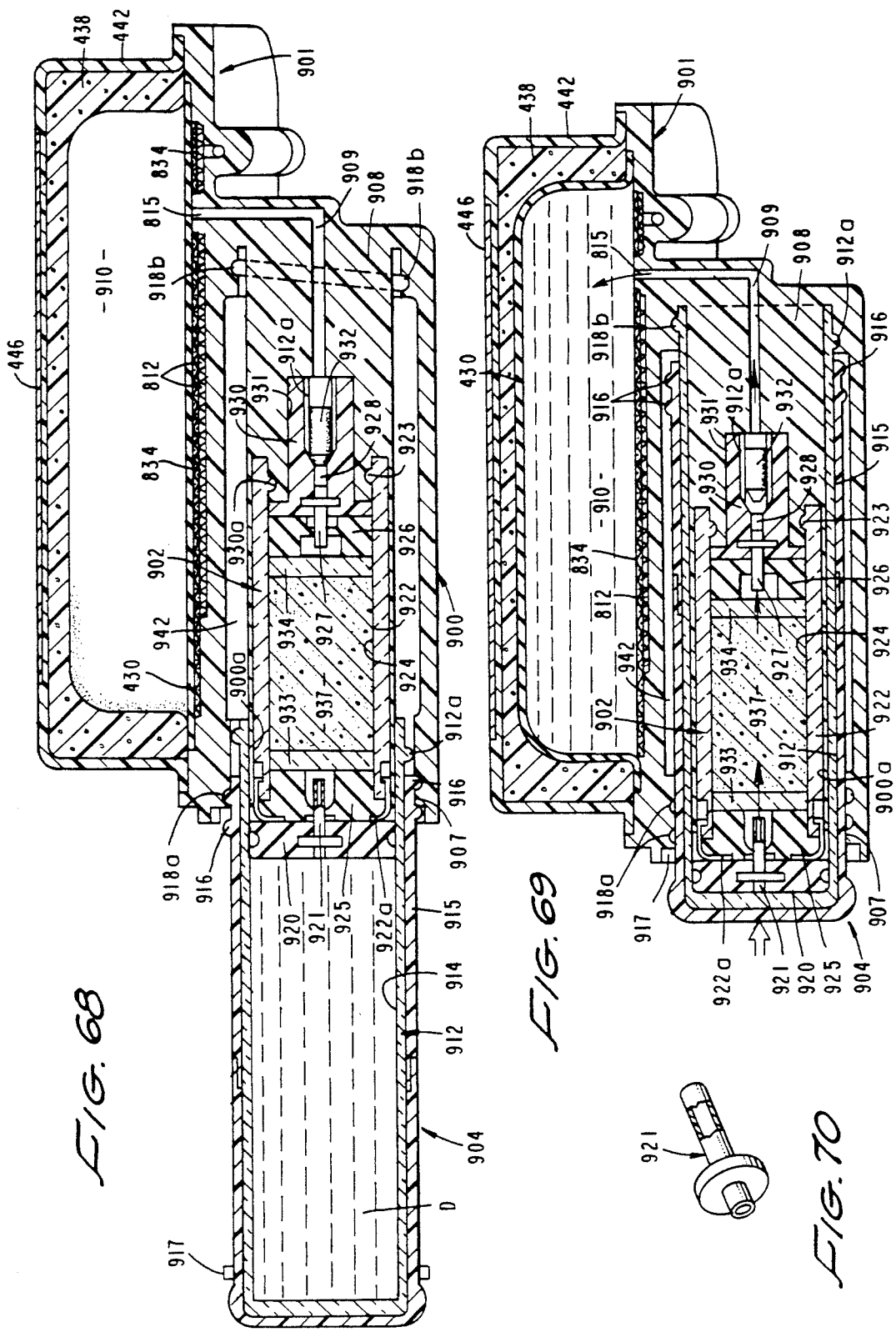

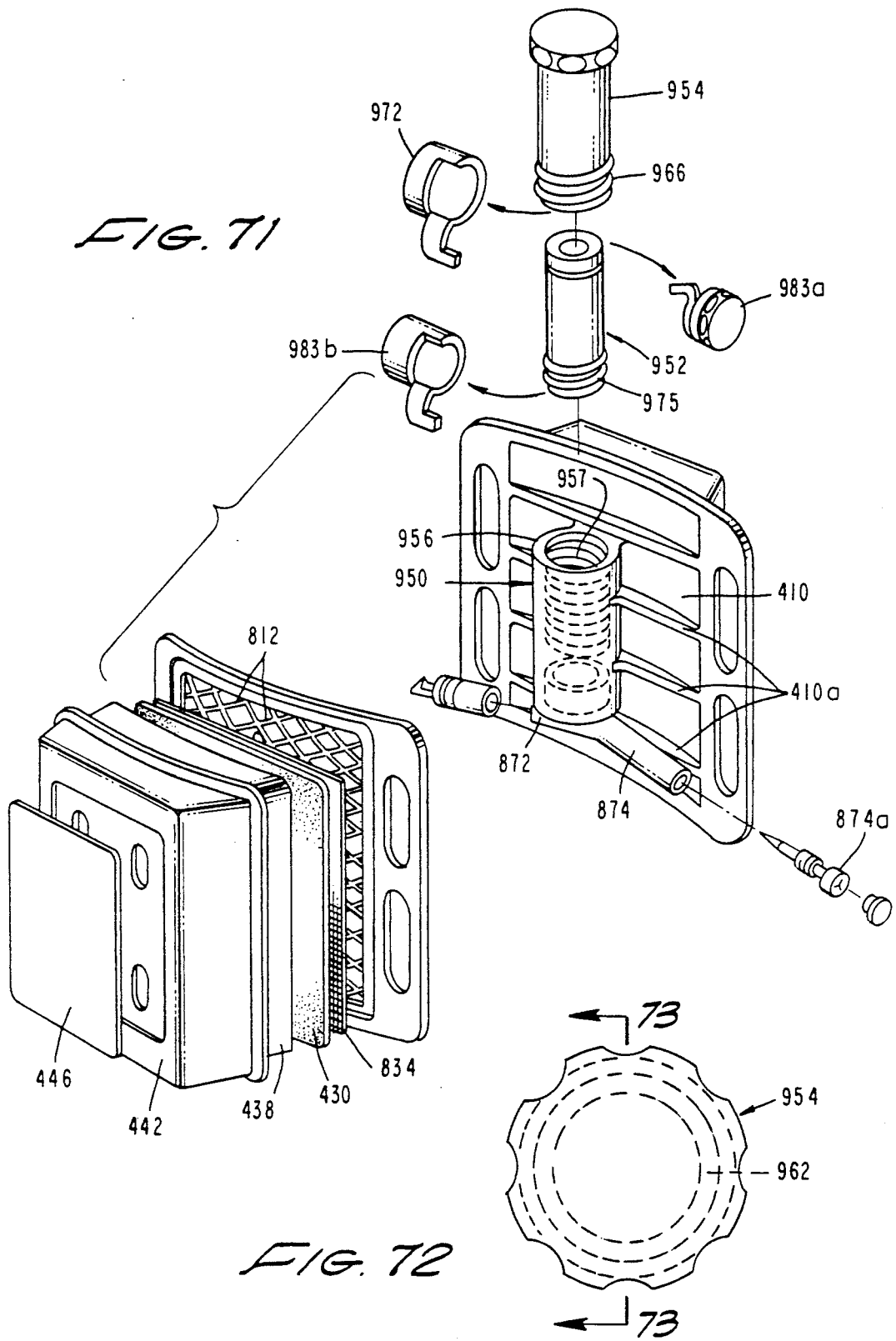

CLOSED DRUG DELIVERY SYSTEM

BACKGROUND OF THE INVENTION

This is a Continuation In Part application of pending Ser. No. 07/870,553 filed Apr. 17, 1992 which is a Continuation In Part of Ser. No. 07/513,917 filed Apr. 24, 1990, now U.S. Pat. No. 5,122,116.

FIELD OF THE INVENTION

The present invention relates generally to fluid mixing and delivery systems. More particularly, the invention concerns an apparatus for intermixing selected medicaments to form a flowable substance and for then infusing the substance into a patient at a precisely controlled rate.

DISCUSSION OF THE INVENTION

Medicament delivering systems that can separately store and then controllably intermix a selected medicament with a diluent for infusion into a patient at a controlled rate have come into wide use. In the prior art systems the diluent is generally packaged in flexible plastic containers having administration ports for connection to an administration set which delivers the container contents from the container to the patient. The drug is often packaged in a separate, closed container and is mixed with the diluent shortly before infusion of the medicament in the patient.

Drugs are typically packaged separately from the diluent for a number of reasons. One important reason is that certain drugs do not retain their efficacy when mixed with a diluent and, therefore, the mixture cannot be stored for any appreciable length of time. Another reason is that many drug manufacturers do not produce medical fluids in containers for intravenous delivery. As a general rule, drugs are packaged in powder form in small, closed containers, or vials, for later mixing with a suitable diluent. In many instances it is necessary to mix the drug with the diluent immediately prior to delivery to the patient to insure that the drug will not separate from the diluent prior to or during infusion.

Infusion of medicaments is most often accomplished in a hospital environment and the nurse, doctor or other medical personnel mixes the drug and diluent shortly before administration of the drug to the patient. This mixing step can be time consuming and hazardous, as for example, when toxic drugs are used. Additionally, many of the prior art mixing devices are crude and imprecise making accurate, sterile and thorough mixing of the drug and the diluent difficult, time consuming and not well suited for use in the home environment.

Several types of closed drug delivery systems are presently in use. These systems typically comprise a flexible container such as a plastic bag to which a drug vial can be coupled. The flexible container usually contains a liquid diluent and often includes a frangible member that allows fluid passage only when broken. When the drug vial is coupled with the flexible container, the stopper of the drug vial is pierced and the frangible member ruptured so as to allow sterile communication between the drug vial and the liquid diluent contents of the flexible container. Mixing of the drug with the diluent is accomplished by manipulating the flexible container. Exemplary of prior art systems of the aforementioned character are those disclosed in U.S. Pat. No. 4,583,971 issued to Bocquet, et al. and in U.S. Pat. No. 4,606,734 issued to Larkin.

Another prior art closed delivery and mixing system is disclosed in U.S. Pat. No. 4,458,733 issued to Lyons. The Lyons apparatus includes a compressible chamber with a liquid component therein, the compressible chamber including gas-trapping and reservoir compartments in open communication. The gas trapping compartment can be connected to a container such as a drug vial having a mixing component therein. After a pathway between the vial and the gas trapping compartment is opened, mixing is accomplished through manipulation of the compressible chamber.

Another very successful prior art, dual container system is described in U.S. Pat. Nos. 4,614,267 issued to Larkin and 4,614,515 issued to Tripp and Larkin. In this system, a flexible diluent container includes a tubular port which provides means for securing thereto a stoppered medicament vial as well as a stopper removal means. The stopper removal means includes an engagement element, or extractor, which is attached to a removable cover and seals the inner end of the port. In use, as the vial is advanced into the tubular port, the vial stopper moves into engagement with the extractor which grips the stopper enabling it to be pulled from the vial as the cover is pulled from the port. Once the stopper has been removed from the vial, the contents of the vial can be dumped into the diluent in the bag and mixed therewith through manipulation of the bag.

The prior art devices of the character described in the preceding paragraphs typically use the traditional gravity flow method for infusion of the medicament mixture into the patient. Such a method is cumbersome, imprecise and typically requires bed confinement of the patient. Also, the flexible bag must be maintained in a substantially elevated position and periodic monitoring of the apparatus by the nurse or doctor is required to detect malfunctions of the infusion apparatus.

The apparatus of the present invention overcomes the drawbacks of the prior art by totally eliminating the need for a flexible bag, the cumbersome manipulative mixing of the medicaments using the flexible bag and the undesirable gravity infusion method which is typically followed when the flexible bag is used. As will be described in the paragraphs which follow, the apparatus of the present invention makes use of recently developed gas permeable elastomeric films and similar materials, which, in cooperation with a plate-like base define a fluid chamber that initially contains the first component, such as a diluent. Adjacent the base and in communication with the fluid chamber is a sterile coupling means for operably interconnecting a container such as a drug vial containing the second component. To enable controlled, sterile intermixing of the first and second components, the apparatus includes flow control means for controlling the flow of fluid through internal passageways which interconnect the fluid chamber and the drug vial.

The apparatus of the present invention is small, compact, easy to use and inexpensive to manufacture. The apparatus provides a sterile, closed delivery system which can readily be used by ambulatory patients and in home care environment. Connector elements are provided on the housing of the device which permits the apparatus to be conveniently affixed to the patient's clothing or to be strapped to the patients body.

The apparatus of the invention can be used with minimal professional assistance in an alternate health care environment, such as the home. By way of example, devices of the invention can be used for intermixing numerous medicaments with suitable diluents and for the continuous infusion of medicament mixtures such as antibiotics, analgesics, hormonal, anticoagulants, clot dissolvers, immuno suppressants, and like medicinal agents. Similarly, the apparatus can be used for I-V chemotherapy and can accurately deliver fluids to the patient in precisely the correct quantities and at extended microinfusion rates over time.

SUMMARY OF THE INVENTION

It is an object of the present invention to provide a compact, lightweight, low-profile apparatus for controllably intermixing two or more components in a closed environment to produce a flowable substance and then for expelling the flowable substance at a precisely controlled rate. More particularly, it is an object of the invention to provide such an apparatus for medical applications which can be used in either a home care or hospital environment for the precise mixing and infusion of diluents and selected medicaments to an ambulatory patient at controlled rates over extended periods of time.

It is another object of the invention to provide an apparatus of the aforementioned character which includes a dispenser portion with its own stored energy means and coupling means for operably interconnecting a drug vial to the dispenser portion for controlled mixing of the medicament within the drug vial with a diluent stored within the dispenser portion via a sterile pathway.

Another object of the invention is to provide an apparatus of the class described which permits extremely accurate fluid mixing and delivering, and one which is highly reliable and easy to use by lay persons in a nonhospital environment.

Another object of the invention is to provide an apparatus which includes an internal fluid reservoir storage chamber that can be factory prefilled with a diluent or one which can readily be filled in the field shortly prior to use.

Another object of the invention is to provide an apparatus of the character described in the preceding paragraph in which the reservoir is provided with an elastomeric energy source that can be subjected to gamma sterilization and extended thermal sterilization temperatures without degradation of integrity and performance.

Another object of the invention is to provide an apparatus in which intermixed fluids can be delivered to the patient either at a fixed rate or at precisely metered variable rates and one which is operational in all attitudes and altitudes.

Still another object of the invention is to provide an apparatus of the class described which includes means for securely interlocking the drug vial with the dispenser portion of the apparatus.

Yet another object of the invention is to provide an apparatus as described in the preceding paragraph which is provided with means for attaching the apparatus to the clothing of the patient or to the patients body.

A further object of the invention is to provide a low profile, fluid delivery device of laminate construction which can be manufactured inexpensively in large volume by automated machinery.

Another object of the invention is to provide a device of the character described in which fluid is dispelled from the apparatus through a cooperating infusion set by a thin, distendable membrane cooperatively associated with a thin, plate-like base.

Another object of the invention is to provide an apparatus of the aforementioned character in which the distendable membrane can be a single elastomeric film, a laminate construction or a composite that is permeable to gases at least in one direction, whereby gases within the intermixed fluids can be released from the fluid chamber and not injected into the patient.

Yet another object of the invention is to provide an apparatus of the class described in which a thin, planar filter element is disposed within the fluid chamber for filtering the reservoir outflow to the patient.

BRIEF DESCRIPTION OF THE DRAWINGS

FIG. 1 is a generally perspective view of one form of the drug delivery system of the present invention.

FIG. 2 is an exploded perspective view of the device shown in FIG. 1.

FIG. 3 is a top plan view of the apparatus shown in FIG. 1 partly broken away to show internal construction.

FIG. 4 is a cross-sectional view taken along lines 4—4 of FIG. 3.

FIG. 5 is a cross-sectional view taken along lines 5—5 of FIG. 3.

FIG. 6 is an enlarged cross-sectional view of the lower right hand portion of the apparatus as viewed in FIG. 3 illustrating construction of the shut-off and metering valve of the apparatus.

FIG. 7 is an enlarged cross-sectional view taken along lines 7—7 of FIG. 3.

FIG. 8 is a fragmentary cross-sectional view illustrating the first step involved in interconnecting the drug vial with the device of the invention.

FIG. 9 is an enlarged fragmentary view illustrating the check valve of the apparatus in a closed position.

FIG. 10 is a cross-sectional view similar to FIG. 8 illustrating the second step in the interconnection of the drug vial with the device of the invention.

FIG. 11 is a cross-sectional view similar to FIG. 10 illustrating the next step in the interconnection of the drug vial with the apparatus and showing the intermixing of fluids contained within the infusion portion of the device with the medicament contained within the vial which has been interconnected with the infusion portion of the device.

FIG. 14 is an enlarged fragmentary view partly in cross-section illustrating the construction of the valving mechanism of the drug vial.

FIG. 17 is a generally perspective view of another alternate form of the apparatus of the invention.

FIG. 18 is fragmentary plan view of the apparatus shown in FIG. 17 partly broken away to show internal construction of the infusion portion of the apparatus prior to the coupling therewith of another form of the drug container or vial.

FIG. 22 is a fragmentary cross-sectional view taken along lines 22—22 of FIG. 21 showing the means for interlocking the drug vial with the infusion portion of the device.

FIG. 23 is a rear perspective view of still another embodiment of the invention.

FIG. 24 is a generally perspective front view of the apparatus of the embodiment shown in FIG. 23.

FIG. 25 is a generally perspective, exploded view of the apparatus of this latest form of the invention.

FIG. 29 is a cross-sectional view illustrating the initial step in the coupling of the drug container with the infusion portion of the device.

FIG. 30 is a cross-sectional view similar to FIG. 11 showing the intermixing of the diluent contained within the infusion portion of the device with the medicament contained within the drug vial.

FIG. 31 is a cross-sectional view showing the transfer step wherein the intermixed fluids are transferred to the reservoir of the infusion portion of the device.

FIG. 41 is a plan view of the drug container of this form of the invention.

FIG. 42 is an enlarged cross-sectional view taken along lines 42—42 of FIG. 43.

FIG. 43 is an enlarged cross-sectional view showing the drug vial assembly in position to be mated with the coupling means.

FIG. 44 is an enlarged cross-sectional view illustrating the initial mating of the drug vial assembly with the infusion portion of the device.

FIG. 45 is an enlarged cross-sectional view similar to FIG. 46 illustrating the intermixing of the diluent with the drug upon the rotation of the drug vial relative to the coupler means to permit fluid to flow from the fluid reservoir of the apparatus toward the mixing chamber.

FIG. 46 is a cross-sectional view taken along lines 46—46 of FIG. 44.

FIG. 47 is a cross-sectional view taken along lines 47—47 of FIG. 45.

FIG. 52 is a plan view of another form of the drug vial assembly of the present invention.

FIG. 53 is an enlarged cross-sectional view of the vial shown in FIG. 54.

FIG. 54 is an enlarged cross-sectional view showing the new drug vial in position to be mated with the coupling means of the apparatus.

FIG. 55 is an enlarged cross-sectional view showing the initial mating of the drug vial with the infusion portion of the apparatus.

FIG. 56 is an enlarged cross-sectional view showing the initial intermixing of the diluent with the beneficial agent contained within the alternate form of the drug vial.

FIG. 57 is a fragmentary cross-sectional view taken along lines 57—57 of FIG. 56.

FIG. 58 is an enlarged cross-sectional view similar to FIG. 56 showing the throttling down of the flow of fluid toward the mixing chamber of the drug vial.

FIG. 59 is a cross-sectional view taken along lines 59—59 of FIG. 58.

FIG. 60 is a cross-sectional view taken along lines 60—60 of FIG. 58.

FIG. 61 is a generally perspective view of the fine control valving means of the container assembly of this last form of the invention.

FIG. 62 is a fragmentary cross-sectional view of the portion of the mixing chamber of the device showing the medicament in a tablet form.

FIG. 65 is a generally perspective, exploded view of the container assembly of this last form of the invention.

FIG. 66 is a a generally perspective view of various forms of adding means, or substrate assemblies, of this later form of the invention FIGS. 66A, 66B, 66C, and 66D are general diagramatic views illustrating various means for affinity attachment of ligands, protein molecules and enzymes to the substrates.

FIG. 68 is an enlarged cross-sectional view of the embodiment shown in FIG. 67 in an assembled configuration ready for use with the fluid reservoir in an uncharged configuration.

FIG. 69 is an enlarged cross-sectional view similar to FIG. 68 but showing the fluid reservoir in a changed configuration.

FIG. 70 is an enlarged, generally perspective view of one of the blunt-end cannulas of the apparatus.

FIG. 71 is a generally perspective, exploded view of yet another form of the invention.

FIG. 72 is an end view of the diluent container of the apparatus.

DESCRIPTION OF THE INVENTION

Figure 12:
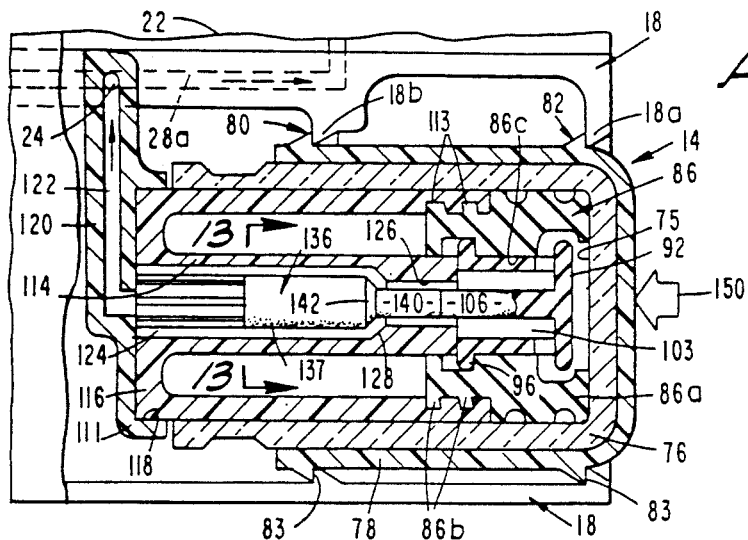
FIG. 12 is a cross-sectional view similar to FIG. 11 but illustrating the further step of transferring the intermixed fluids contained within the drug vial to the reservoir of the infusion portion of the device of the invention.

Referring to the drawings and particularly to FIGS. 1 and 2, the apparatus of one form of the present invention, generally designated by the numeral 12, is used for intermixing a first component contained within a separate container, such as a drug vial 14, with a second component contained within a storage reservoir disposed internally of the infusion portion of the apparatus to form an injectable fluid and then for infusing the fluid into a patient at a controlled rate. In this first embodiment of the invention, shown in FIGS. 1 through 11, the apparatus comprises a housing 16 having a first cylindrical portion 18 and a second infusion device portion 20.

As best seen by referring to FIG. 2, first portion 18 includes coupling means for operably coupling container 14 with the infusion portion of the device. Second portion 20 of housing 16, the construction of which will be described in greater detail hereinafter, comprises the infusion device portion of the apparatus and includes a base assembly 21 having a generally planner, plate-like base 22. Base 22 includes a fluid inlet 24 and a fluid outlet 26 which are in communication via a multi-legged fluid passageway 28. Fluid passageway 28 includes a first transversely extending leg 28a which is in communication with fluid inlet 24, a second, spaced-apart transversely extending leg 28b and a pair of longitudinally extending legs, or conduits, 28c which interconnect legs 28a and 28b. Transversely extending leg 28b is in communication with fluid outlet 26 in the manner shown in FIG. 2.

Turning also to FIGS. 4 and 5, the apparatus of this form of the invention further includes a distendable membrane 30 constructed of an elastic material. Membrane 30 is adapted to fit over base 22 and cooperate therewith to define one or more diluent storage reservoirs, or chambers 32. Membrane 30 is distendable by fluid introduced under pressure into chamber 32 through a sealable inlet port 33 provided in base 22. The elastic character of membrane 30 is such that the membrane, after being distended has a tendency to return to its original less distended configuration. This causes the fluid to flow outwardly of the apparatus through fluid outlet 26 upon opening the flow control means of the invention. The details of construction of both the flow control means and of membrane 30 will be discussed in the paragraphs which follow.

Disposed intermediate distendable membrane 30 and the upper planner surface 22a of base 22 is means for creating an ullage within chamber 32. This means is here provided in the form of a pair of spaced apart outwardly extending protuberances 34. Each of the protuberances 34 is provided with a longitudinally extending first passageway or conduit 36. When the apparatus is assembled in the manner illustrated in FIGS. 4 and 5, passageways 36 are superimposed directly over spaced-apart fluid conduits 28c and the membrane engaging means, shown here as protuberances 34, extend upwardly into fluid chambers 32 defining ullage therewith. In operation of the device, as distendable membrane 30 attempts to return to its less distended configuration, it will move toward engagement with the upper surfaces of protuberances 34 and, in so doing, will efficiently force the fluid contained within chambers 32 into conduits 28c through passageways 36 (FIG. 5). The configuration of protuberances 34 ensure that substantially all of the fluid within chambers 32 will be controllably dispelled therefrom as the membrane returns toward its original planar configuration.

Superimposed over distendable membrane 30 is a porous plastic, free venting, structural filler member 40. As best seen by referring to FIG. 5, member 40 is provided with a pair of longitudinally extending, concave channels 42 having interior walls 43 against which membrane 30 initially engages when it is outwardly distended by fluid flowing from an inlet 33 provided in base assembly 21 into chambers 32 under pressure.

Superimposed over and sealably enclosing base 22 and member 40 is a cover means shown here as a hard plastic cover 44. Cover 44 includes a first portion 44a which comprises the upper segment of cylindrical portion 18 of housing 16 (FIG. 2). As will be described further hereinafter, cylindrical portion 18 houses the coupling means of the apparatus, which includes first flow control means, for operably coupling the drug vial with the infusion portion of the device. Cover 44 also includes gas venting means here provided as a plurality of apertures 46 formed within the upper wall of cover member 44. When distendable membrane 30 is constructed of a gas permeable material, gas venting means, including apertures 46, permit any gases contained within the fluids introduced into chambers 32 to pass through the gas permeable membrane, through filler 40 and to atmosphere through the gas venting means. A medicament label 48, which may also be permeable to gases, covers vent apertures 46. Forming still another part of cover assembly 44 is a removable belt clip 50 provided with a dovetailed mortise 52 adapted to be slidably receivable over an up-standing mating tenon 54 formed on the upper surface of cover member 44.

Base assembly 21 also includes an outlet port 56 which is normally closed, by a removable cover member 58. Outlet port 56 is in communication with fluid outlet 26 via a conduit 57. Outlet port 56 is also in communication with a transversely extending passageway 60 which terminates at its outer end in an opening 62 (FIG. 2). Receivable within opening 62 is an outlet flow control means shown here as a shut-off and fluid metering means 63 which comprises a needle valve of standard construction having an elongated valve stem or member 64 which is closely receivable within passageway 60 (FIGS. 2 and 6). Provided at one end of stem 64 is a control knob 66. Provided at the opposite end is a tapered portion 68 adapted to cooperate with a valve seat 69 provided on base 22 for either substantially blocking or for controllably restricting the flow of fluid outwardly of the device through conduit 57 and outlet port 56. As best seen in FIG. 6, passageway 60 is internally threaded to threadably receive external threads 70 formed on stem 64. With this construction, by rotating control knob 66, valve member 64 can be moved axially of passageway 60 to controllably move tapered portion 68 of the valve relative to passageway 57 and into engagement with valve seat 69 so as to control fluid flow through passageway 57. An O ring 67 is provided to seal stem 64 relative to passageway 60.

Turning now to FIG. 8, the construction of the container, or drug vial portion 14 of the apparatus of the present invention, is there illustrated. In this form of the invention, the container includes second flow control means for controlling the flow of fluid into and out of an internal chamber 75 of a vial 76. Closely received over vial 79 is a plastic cover, or overpackage 78 which is provided with vial interlocking means shown here as a pair of spaced apart, circumferentially extending safety interlocks 80 and 82, the purpose of which will presently be described. Each of the circumferentially extending interlocks 80 and 82 is provided with a radially outwardly extending flat surface 83 which is adapted to lockably engage one of a pair of spaced apart annular stops 18a and 18b provided internally of cylindrical portion 18 (see also FIG. 2). Annular stops 18a and 18b comprise novel stop means which are adapted to interengage the vial interlocking means provided on the drug vial assembly to prevent removal of the drug vial from cylindrical portion 18 after it has been introduced and mated therewith.

The second flow control means of this first form of the invention comprises a plunger 86 which is substantially sealably receivable within vial 76. Vial 76 is movable relative to plunger 86 between a first position shown in FIGS. 8 and 10 and a second position shown in FIG. 11 and from the second position to a third position shown in FIG. 12. Plunger 86 is generally cylindrical in shape having a skirt portion 86a adapted to substantially sealably engage the inner walls of vial 76. Plunger 86 also includes first connector means, or interengagement means, shown here as threads 86b, for interconnection with the coupling means of the apparatus. Disposed within a central passageway 86c formed interiorly of the plunger is a plunger valve means here provided as a valve assembly 88. Referring also to FIG. 14, valve assembly 88 includes a cylindrically-shaped central portion 90 closed at one end by a disk-shaped member 92. Fluid passageways 94 are provided through the cylindrical wall of central portion 90 proximate member 92, which member is preferably integrally formed with portion 90. Provided at the opposite end of central portion 90 is an annular shaped member 96.

As best seen in FIGS. 8 and 10, plunger 86 is provided with a central portion 87 which includes spaced-apart, radially, inwardly extending seats or shoulders 100 and 102. When the valve assembly 88 is in the closed position shown in FIG. 8, the periphery of member 92 is substantially sealably seated against shoulder 100 and annular portion 96 is spaced apart from shoulder 102. On the other hand, when the valve is in the open position shown in FIG. 10, the periphery of member 92 is spaced apart from shoulder 100 and annular portion 96 of the valve member is in engagement with shoulder 102. If desired, central portion 90 can be constructed to provide support to a stem 106 as stem 106 moves axially of the central body portion. With the valve in the open position shown in FIG. 10, fluid can flow from the central passageway 103 of the valve through radially extending passageways 94 and into the vial in the manner indicated by the arrows of FIG. 10.

Valve assembly 88 is moved from the closed position into the open position by operating means, here comprising a plunger stem portion 106 which is integrally formed with disk-shaped member 92 and, as shown in FIGS. 8 and 14, extends axially of valve passageway 103. As will be presently described, the operating means functions to operate the first and second control means of the invention, including valve assembly 88, for controlling the flow of fluid into and out of drug vial 14.

Before discussing the mode of operation of the operating means, the previously identified coupling means for coupling the container 14 with portion 18 of the housing will be discussed. As best seen by referring to FIGS. 2, 3, and 8, the coupling means here comprises a sterile coupling assembly 110 which is supported centrally of cylindrical housing portion 18 by a rigid coupling support 111 which extends transversely of housing portion 18. Coupling assembly 110 comprises an outer cylindrical portion 112 having second connector means or internal threads 113 and a co-axially aligned, inner cylindrical portion 114. Inner portion 114 is held rigidly in position within outer portion 112 by means of a circular shaped end wall 116 (FIG. 8). As best seen by also referring to FIG. 2, end wall 116 is closely received within a recess or socket 118 formed in coupling support 111. Also forming a part of coupling support 111, is a radially extending connector element 120 having an internal fluid passageway 122 which is adapted to communicate with inlet 24 of base 22 when support 111 is positioned within cylindrical portion 18 in the manner shown in FIGS. 3 and 8. Passageway 122 communicates with a passageway 124 which is defined by the interior walls of cylindrical portion 114. A smaller diameter fluid passageway 126 joins passageway 124 at a value seat defining, tapered wall portion 128 (FIG. 8).

Turning also to FIG. 9, a coupling valve means, generally designated by the numeral 136, which also forms a part of the coupling means of the present invention, is reciprocally movable within passageway 124 and functions to control the flow of fluid through passageway 126 in a manner presently to be described. As indicated in FIGS. 8 and 9, coupling valve means 136 includes a valve element 137 having a body portion 138 and a coupling stem portion 140. At the junction of portions 138 and 140 is a tapered wall 142 which is adapted to substantially sealably engage the valve seat defined by tapered wall portion 128 when the valve is in the closed configuration shown in FIG. 8. When the apparatus of the invention is in a storage mode, the open end of coupling 110 is closed by a removable sealing cap 130 which is provided with a pull tab 132 for use in removing the cap from the sterile coupling (FIG. 2).

In operating the apparatus of the invention, the drug vial closure cap 146 (FIG. 2) is first removed from the drug vial 14. This done the closure cap 130, which closes the passageway of the sterile closure element 110, is removed and the open end of the drug vial 14 is inserted through open end 148 of cylindrical portion 18 (FIG. 8). As the drug vial 14 is received within open end 148, locking member 80 on the overpackage will slip past stop member 18a on cylindrical portion 18 and threads 86b will move into mating engagement with threads 113 provided on coupler member 112. Rotation of the drug vial in a clockwise direction will cause the plunger to couple with coupling member 112 in the manner shown in FIG. 10. As the parts are coupled together, stem 106 of the container valve will engage stem 140 of valve means 136 simultaneously axially moving both valve member 137 of the first flow control means and valve member 92 of the second flow control means into the open position shown in FIG. 10. With the valves of the flow control means in this position, distendable membrane 30 will cause the fluid contained within chambers 32 to flow under pressure past the valve seat 128 into fluid passageway 126 of the coupler means and then into passageway 103 of the container valve means. The fluid under pressure will next flow through radially extending passageways 94 of the container valve and rapidly into the interior of container 76 in the manner shown by the arrows in FIG. 10. This rush of fluid under pressure into the drug vial initiates the mixing or reconstitution process.

As illustrated in FIG. 11, the fluid flowing into the drug vial will mix with the medicament M contained within the vial in the manner shown to form a flowable substance comprising a mixture of the liquid which was stored within chambers 32 and the medicament M which was stored within the drug vial. It is important to note that, as the fluid under pressure rushes into the drug vial, the drug vial will move outwardly into the position shown in FIG. 11 wherein surface 83 of the vial locking means or locking member 80 provided on the plastic overpackage will engage first stop means or member 18a provided interiorly of cylindrical housing portion 18. It is to be noted that in this position, the plunger 86 has traveled from an intermediate position within vial 76, as shown in FIG. 8, to an outward position shown in FIG. 11 wherein plunger 76 is located proximate the open mouth of the glass container 76. Contained air, if any, within vial 76 assists in the turbulent mixing process.

Figure 13:
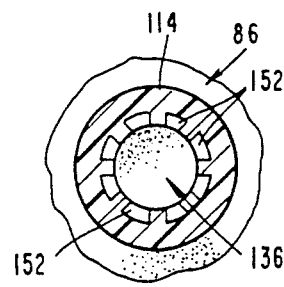
FIG. 13 is a cross-sectional view taken along lines 13—13 of FIG. 12.

The reconstituted mixture, the medicament M stored within container 14, and residual air if any is next transferred back into the infusion device reservoir by exerting an inward pressure on the drug vial in the direction of the arrow 150 of FIG. 12. As the drug vial 14 is reinserted into cylindrical portion 18, the reconstituted mixture contained in the drug vial is directed through radial passageways 94, of the drug vial valve into passageway 103 of the valve, into passage 126, passed valve seat 128 and into passageway 124 of the coupling means. The fluid will then flow into chambers 32 via passageways 122 and 28 (FIG. 5). Entrained air, if any, will vent to atmosphere through gas permeable elastomeric membrane 30 by the permeation transport process. As illustrated in FIG. 13, the interior wall of inner cylindrical member 114 of the coupling means is provided with a plurality of circumferentially spaced fluid passageways 152 to facilitate flow of fluid to and from the chambers 32 provided within the drug infusion portion of the apparatus.

It is to be observed from FIG. 12 that continued inward pressure exerted on the drug vial 14 will cause locking member 80 provided on overpackage 78 to slip past and lockably engage second stop member 18b provided internally of cylindrical chamber 18. Similarly locking member 82 will slip past first stop member 18a of cylindrical portion 18 and lock against locking member 18a. With the parts of the apparatus in the configuration shown in FIG. 12, the drug vial 14 is non-removably locked in position within cylindrical chamber 18 of housing 16.

The flow of the reconstituted mixture of the first and second components contained within the vial 14 into chambers 32 due to the telescopic movement of the drug vial into cylindrical portion 18 will urge the partially distended membrane 30 into the distended configuration shown in FIG. 5. Once distended, membrane 30 will continuously exert a pressure on the now fully intermixed fluid contained within chambers 32 so that upon the removal of cap 58 and the opening of needle valve 64, the newly reconstituted drug and diluent comprising the combined intermixed fluid components will be infused into the patient at a controllable rate through any suitable interconnection means such as an infusion needle connected to the conduit shown in dotted lines in FIG. 1 and designated by the numeral 154. As previously discussed, the rate of infusion of the liquid from the apparatus of the invention into the patient can be precisely controlled through the manipulation of the needle valve 64.

Contributing to the superior performance of the apparatus of the invention are the several state-of-the art materials used in the construction of the apparatus. These materials markedly contribute to the reliability, accuracy and manufacturability of the apparatus. Before discussing the alternate forms of the invention shown in the drawings, a brief review of the materials used in constructing the apparatus of the invention is in order.

With respect to the base 22 and cover 44, a wide variety of materials can be used, including; metals, rubber or plastics that are compatible with the liquids they contact. Examples of such materials are stainless steel, aluminum, latex rubber, butyl rubber, nitrile rubber, polyisiprene, styrene-butadiene copolymer, silicones, polyolefins such as polypropylene and polyethylene, polyesters, polyurethane, polyamides and polycarbonates.

Considering next the elastic distendable membrane 30, this important component can be manufactured from several alternate materials including rubbers, plastics and other thermoplastic elastomers. These include latex rubber, polyisoprene (natural rubber), butyl rubber, nitrile rubber, polyurethanes, Ethylene-Butadiene-Styrene Copolymers, Silicone modified Polyurethanes, fluorocarbon elastomers, fluorosilicones, fluoralkoxyphosphazene ploymers and other polymer multicomponent systems including copolymers (random, alternating, block, graft, crosslink and starblock), mechanical poly-blends and interpenetrating polymer networks.

Examples of materials found particularly well suited for this application include; silicone polymers (polysiloxanes) and high performance silicone elastomers made from high molecular weight polymers with appropriate fillers added. These materials are castable into thin film membranes and have high permeability (which allows maximum transport of vapor and gas), high bond and tear strength and excellent low temperature flexibility and radiation resistance. Additionally, silicone elastomers retain their properties over a wide range of temperature ($-80°$ to $200°$ C.) are stable at high temperatures, and exhibit tensile strengths up to 2,000 lb./in$^2$ elongation up to 600%.

Further, silicone (polyorganosiloxanes) are thermally stable, hydrophobic organometallic polymers with the lowest P-P interaction (of all commercially available polymers. This fact coupled with the flexibility of the backbone results in a low Tg ($-80°$ C.) and an amorphous rubbery structure for the high MW (polydimethylsiloxanes). Silicone rubber membranes are considerable more permeable to gases than membranes of any other polymer. Depending on the medicinal fluid used and the filling of the storage mode, which will determine the desired mass transport characteristics of the membrane (permeability and selectivity), other materials of choice include polyurethane-polysiloxane copolymers, blends and IPN's. By example, polydimethylsiloxane (PDMS) and polyurethane (PU) multicomponent IPN containing 10%-20% weight of PU shows enhanced initial modulus relative to that of PDMS itself.

Interpenetrating polymer networks (IPNS) are unique blends of cross-linked polymers containing essentially no covalent bonds, or grafts between them. True IPNS are also homogeneous mixtures mixtures of component polymers. Further examples of an additional candidate materials would be a polyurethane-polysiloxane (IPN) bilaminated with a polyparaxylene or alternately bilamination of polydimethylsiloxane (PDMS) and polyparaxylene. Coextruded laminates of this type can be selected according to the desired gas permeability for vapor and $O_2$, $N_2$ and $CO_2$ diffusion and their specific selectivity requirements as well as for direction of gas migration when appropriately layered. Additionally, interfacial surface layers of various materials of on the order of 5 to 20 angstroms thick can be provided on the membrane to establish a biocompatible interface without substantially effecting the membrane permeation rate.

With respect to the structural filter 40, many types of porous plastic materials can be used. In certain embodiments of the invention, this component can be produced from one of several polymer groups. The plastic structure of this component typically contains an intricate network of open celled omni directional pores. The pores can be made in average sizes for 0.8 micron to 2,000 micron and, gives the porous plastic a unique combination of venting and structural strength. Further, the material is strong, lightweight, has a high degree of chemical resistance and, depending on the particular configuration of the apparatus, can be flexible. The degree of hardness can range from soft, resilient or rigid, and depending on the specific micro diameter range desired, the following polymers can be employed: Polypropylene(PP), Ultra high molecular weight polyethylene (UHMW PE), High density polyethylene (HDPE), Polyvinylidene Fluoride (PVDF), Ethylene-vinyl acetate (EVA), Styrene Acrylonitrile (SAN), Polytetrafluoroethylene (PTFF).

An alternate material for use in constructing the cover 40 and base 22 so as to serve as a non-permeable gas barrier, is a material sold by B-P Chemicals International of Cleveland, Ohio, under the name and style "Barex". This material, is a clear rubber modified Acrylonitrile Copolymer which has wide application in the packaging industry because of its superior gas barrier, chemical resistance and extrusion (thermoforming) and injection molding capabilities. Structures using this or similar barrier materials can be manufactured in either monolayer or coextrusion (with such other materials as polyethylene, polypropylene, polystyrene and other modified styrenes). Combinations of different materials can be used to enhance the desired physical properties of the thermoformed part.

Figure 15:
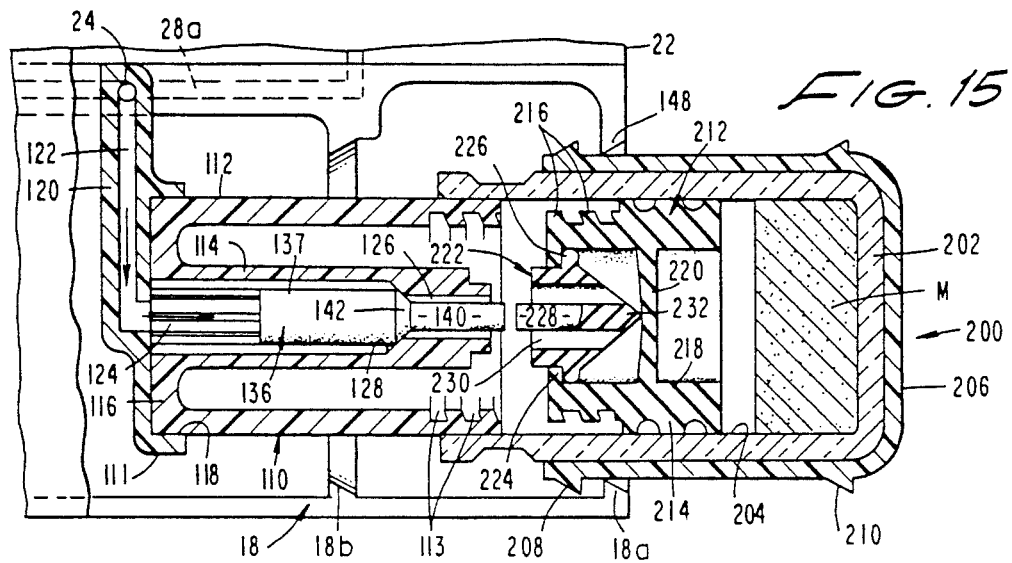
FIG. 15 is a fragmentary cross-sectional view similar to FIG. 10 but showing an alternate embodiment of a drug vial usable with the apparatus of the invention.
Figure 16:
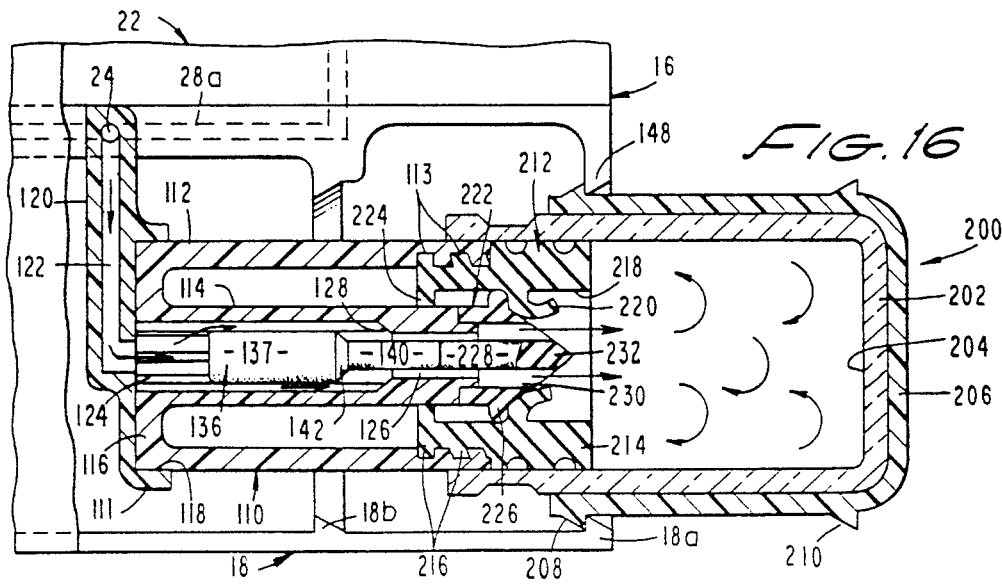
FIG. 16 is a fragmentary cross-sectional view similar to FIG. 11 and illustrating the intermixing of fluids contained within the infusion portion of the device with the medicament contained within the second form of the drug vial shown in FIG. 15.

Turning now to FIGS. 15 and 16, a second embodiment of the present invention is there shown. In this form of the invention, the first and second portions of the housing, and the infusion device portion of the apparatus are identical in construction and operation to those of the first embodiment just described and like numbers are used to identify like components. However, the container assembly, generally designated in FIGS. 15 and 16 by the numeral 200, is somewhat different.

Container assembly 200 comprises a glass vial 202 having a chamber 204 for containing a medicament M. A plastic cover or overpackage 206 is closely received over vial 202 and includes first and second locking members 208 and 210 which are identical to locking members 80 and 82 as previously described. Housed within vial 202 is the second flow control means of this form of the invention for controlling the flow of fluid into and out of chamber 204. Here the second flow control means comprises a plunger 212 substantially sealably received within vial 202. Plunger 212 is of generally similar construction to plunger 86 being cylindrical in shape and having a skirt portion 214 adapted to substantially sealably engage the inner wall, of vial 202. Plunger 212 also includes similar connector means shown here as threads 216 for interconnection with threads 113 provided on coupling number 112.

In this second form of the invention, however, plunger 212 has an internal passageway 218 which is normally blocked by a transversely extending, frangible or pierceable diaphragm 220. A first valve means, here provided as a vale assembly 222, is disposed within passageway 218 and, in cooperation with diaphragm 220, controls fluid flow through passageway 218. Plunger 212 includes an inwardly extending flange 224 against which a flange 226 provided on valve assembly 222 normally seats (FIG. 15). Valve assembly 222 also includes a stem 228, which, in this form of the invention, comprises a part of the operating means for operating the coupling valve and the plunger valve. A fluid passageway 230 surrounds stem 228. Stem 228 is integrally formed with the plunger body which terminates in a point 232. As indicated in FIG. 15, when valve assembly 222 is in the normal position shown in FIG. 15, point 232 is in engagement with diaphragm 220.

In operating the apparatus of this second form of the invention, when plunger 214 is threadably connected to coupler member 112 in the manner shown in FIG. 16, valve assembly 222 will be moved to the right by stem 140 of the coupling valve 136 and diaphragm 220 will be ruptured. At the same time, valve 136 will be axially moved into the open position permitting the fluid contained within the reservoir of the delivery portion of the device to flow through passageways 230 into chamber 204 of the vial 202 and to mix with the medicament M. The fluid under pressure flowing from the reservoir of the delivery portion of the device forces the container assembly outwardly to the position shown in FIG. 16 with locking member 208 engaging stop member 18a provided on the first portion 18 of housing 16. After this reconstitution process, the reconstituted fluid is forced into the reservoir of the delivering portion of the device in the manner previously described by pushing the container assembly to the left as shown in FIG. 16 and into a locked position similar to that shown in FIG. 12 and earlier described.

Turning now to FIGS. 17 through 22, still another form of the invention is there illustrated. The infusion device portion of this embodiment of the invention is substantially identical in construction and operation to that of the first two forms of the invention, and like numerals are used to identify like component parts. However, the coupling portion of the device is slightly different, as is the construction of the drug vial assembly identified here by the numeral 300.

The infusion device portion of this third embodiment of the invention also includes a base assembly 21 having a generally planner base 22. Base 22 has a fluid inlet 24 and a fluid outlet 26 (not shown) which are in communication via a multi-legged fluid passageway 28. As before, fluid passageway 28 includes a first transversely extending leg 28a which is in communication with fluid inlet 24, a second, spaced-apart, transversely-extending leg 28b (not shown) and a pair of longitudinally extending legs, or conduits, 28c which interconnect legs 28a and 28b. Transversely extending leg 28b is in communication with fluid outlet 26 in the manner shown in FIG. 2.

The apparatus of this form of the invention also includes a distendable membrane 30 constructed of an elastic material. Membrane 30 is adapted to fit over base 22 in the manner previously described and cooperates therewith to define one or more diluent storage reservoirs, or chambers 32 of the character shown in FIG. 5. Membrane 30 is distendable by fluid introduced under pressure into chambers 32 through a sealable inlet port 33 provided in base 22 (FIG. 18). As in the previously described embodiments, the elastic character of membrane 30 is such that the membrane, after being distended has a tendency to return to its original less distended configuration. This causes the fluid to flow outwardly of the apparatus through the fluid outlet port upon opening the flow control means of the invention.

Disposed intermediate distendable membrane 30 and the upper planner surface 22a of base 22 is means for creating an ullage within chambers 32. This means is once again provided in the form of a pair of spaced-apart, outwardly extending protuberances 34. Each of the protuberances 34 is provided with a longitudinally extending first passageway or conduit 36. When the apparatus is assembled in the manner illustrated in FIGS. 4 and 5, passageways 36 are superimposed directly over spaced-apart fluid conduits 28c and membrane engaging means, shown here as protuberances 34, extend upwardly into fluid chambers 32 defining ullage therewithin. The operation of the distendable membrane 30 to efficiently force the fluid contained within chambers 32 outwardly of the device through outlet 56 is as previously described. The construction and operation of the outlet flow control means, or shut off and fluid metering means 63 is also as previously described.

Superimposed over distendable membrane 30 is a porous plastic, free venting, structural filler member 40 (not shown in FIG. 17), which, in turn, is covered by a cover 44 of the character previously described.

The first portion of the housing, designated in FIG. 17 by the numeral 302, is of a slightly different construction than first housing portion 18. Rather than being provided with stop members 18a and 18b of the character shown in FIG. 2, first housing portion 302 is here provided with internal threads 304, the purpose of which will presently be described. Portion 302 is also provided with container locking means shown here as resilient ratchet teeth 306 which interface and interlock with mating ratchet teeth 308 provided on the drug vial container assembly.

Figure 19:
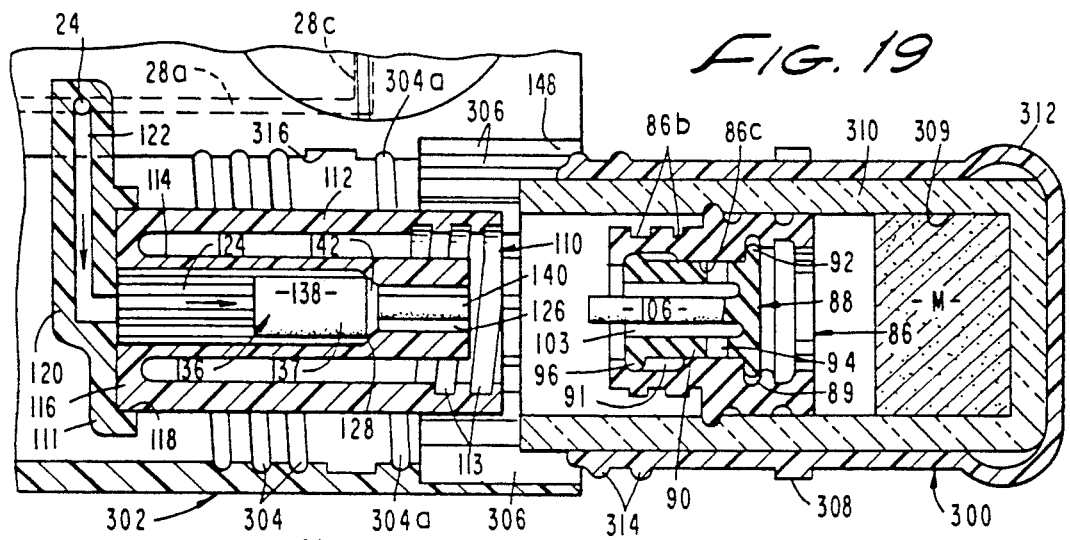
FIG. 19 is an enlarged cross-sectional view illustrating the initial step in mating the drug container shown in FIG. 18 with the infusion portion of the device.

The coupling means of this third form of the invention is substantially identical to the coupling means of the earlier described embodiments and comprises a sterile coupling assembly 110 which is supported centrally of cylindrical housing portion 302 by a rigid coupling support 111 which extends transversely of housing portion 302. Coupling assembly 110 comprises an outer cylindrical portion 112 having internal threads 113 (FIG. 19) and a coaxially aligned inner cylindrical portion 114. As before, inner portion 114 is rigidly held in position within outer portion 112 by means of a circular shaped end wall 116 (FIG. 19). As best seen by also referring to FIG. 19, end wall 116 is closely received within a recess or socket 118 formed in coupling support 111. Also forming a part of coupling support 111, is a radially extending connector element 120 having an internal fluid passageway 122 which is adapted to communicate with inlet 24 of base 22 when support 111 is positioned within cylindrical portion 302 in the manner shown in FIGS. 17 and 18.

Turning to FIG. 19, passageway 122 communicates with a passageway 124 which is defined by the interior walls of cylindrical portion 114. A smaller diameter fluid passageway 126 joins passage 124 at a valve seat defining tapered wall portion 128. A valve means, generally designed by the numeral 136, which is of the character previously described, is reciprocally movable within passageway 124 and functions to control the flow of fluid through passage 126 in a manner presently to be described. As indicated in FIGS. 8 and 9, valve means 136 includes a valve element 137 having a body portion 138 and a stem portion 140. At the junction of portions 138 and 140 is a tapered wall 142 which is adapted to substantially sealably engage the valve seat defined by tapered wall portion 128 when the valve is in the closed configuration shown in FIG. 19. When the apparatus of the invention is in a storage mode, the open end of coupling 112 is preferably closed by a removable sealing cap 130 of the character shown in FIG. 1.

Figure 20:
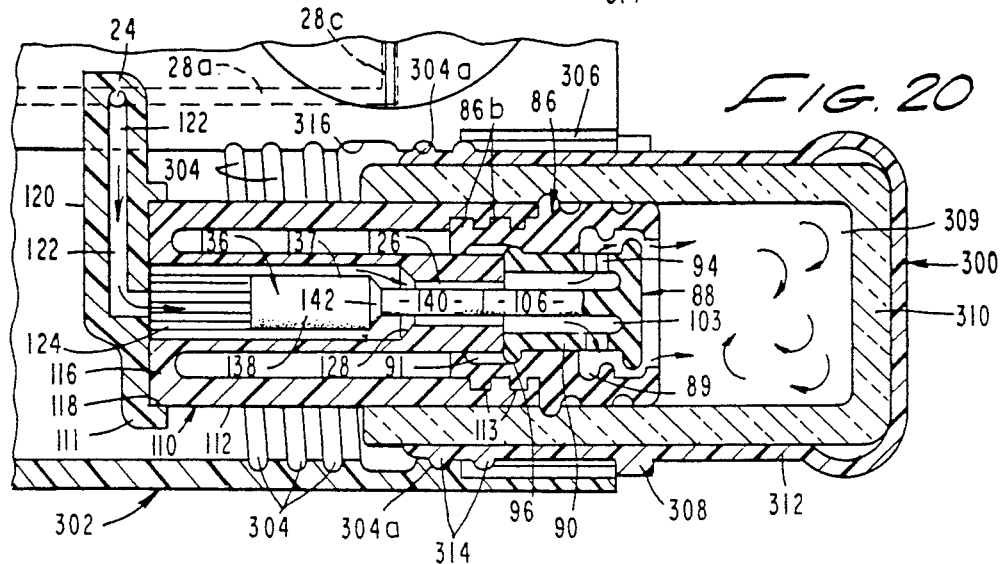
FIG. 20 is a cross-sectional view similar to FIG. 11 showing the intermixing of the diluent contained within the infusion portion of the device with the medicament contained within this latest form of drug vial.

In this form of the invention shown in FIGS. 17 through 21, container assembly 300 includes second flow control means for controlling the flow of fluid into and out of an internal chamber 309 of a glass vial 310.(FIG. 19) which contains the medicament M. The second flow control means of this form of the invention is similar in construction and operation to that previously described and includes a plunger 86 which is substantially sealably receivable within vial 310. Plunger 86 also includes connector means, shown as threads 86b, for interconnection with the coupling means of the apparatus. As before, valve assembly 88 controls fluid flow through passageway 86c formed within plunger 86 and is operated by operating means of the character previously described. However, as seen in FIGS. 19 and 20 plunger 86 includes circumferentially extending, annular channel portions 89 and 91 which substantially sealably engage members 92 and 96 respectively of member 90.

Glass vial 310 is enclosed in a multi-part cover, or overpackage 312 which surrounds vial 310 and includes the previously identified, circumferentially extending ratchet teeth 308. Provided proximate the open end of cover 312 are external threads 314 which are adapted to mate with internal threads 304 provided within cylindrical portion 302 of the apparatus housing. Vial 310 (FIG. 18) is closed by a tear-away removable closure cap such as 311 which is integrally formed with the forward part 312f of overpackage 312.

In operating the apparatus of this third form of the invention, vial closure cap 311 is first removed from the drug vial assembly 300. This done closure member 130, which closes the passageway of the sterile closure element 110, is also removed and the open end of the drug vial assembly 300 is inserted into open end 148 of cylindrical portion 302 (FIG. 19). As the drug vial 310 is received within open end 148, threads 314 will move toward a first internal thread 304a provided within cylindrical portion 302 (FIG. 19). Simultaneously threads 86b will move toward mating engagement with threads 113 provided on coupler member 112. Rotation of the drug vial in a clockwise direction will cause threads 314 to mate with first internal thread 304a and will cause threads 86b on plunger 86 to mate with threads 113 on coupling member 112 in the manner shown in FIG. 20. Teeth 308 provided on overpackage 312 will also move to a location proximate ratchet teeth 306. As the plunger couples with member 112, stem 106 of the container valve will engage stem 140 of valve means 136 simultaneously moving both valve member 137 of the first flow control means and valve member 92 of the second flow control means into the open position shown in FIG. 20. With the valves of the flow control means in this open position, distendable membrane 30 will cause the fluid contained within chambers 32 to flow under pressure past the valve seat 128 into fluid passageway 126 of the coupler means and then into passageway 103 of the container valve means. The fluid under pressure will next flow through radially extending passageways 94 of the container valve and rapidly into the interior 309 of the glass container 310 in the manner shown by the arrows in FIG. 20. This flow of fluid under pressure into the drug vial initiates the mixing or reconstitution process.

As depicted by the arrows in FIG. 20, the fluid flowing into the drug vial will thoroughly mix with the medicament M contained within the vial in the manner shown to form a drug active flowable substance comprising a mixture of the diluent stored within chambers 32 and the medicament M which was stored within the drug vial.

After the medicament M is mixed with the diluent, the drug vial assembly is once again rotated in a clockwise direction. During this further rotation, threads 314 on the drug vial will move through a circumferentially extending space 316 provided within cylindrical portion 302. As shown in FIG. 20, space 316 functions as a dwell space and is located intermediate first thread 304a and threads 304. Continued clockwise rotation of the drug vial assembly will cause threads 314 to mate with threads 304 moving the drug vial assembly from the position shown in FIG. 20 to the seated position shown in FIG. 21. Ratchet teeth 308 on the overpackage will also mate with resilient ratchet teeth 306 provided within housing portion 302. As best seen in FIG. 22, ratchet teeth 306 are constructed so that they are yieldably deformable in a manner to permit the drug vial assembly to be freely rotated in a clockwise direction, but are designed to engage teeth 308 in the manner shown in FIG. 22 to preclude block counter-clockwise rotation of the vial assembly. With this construction, once the drug vial assembly is mated with cylindrical housing portion 302 it cannot be easily removed.

Figure 21:
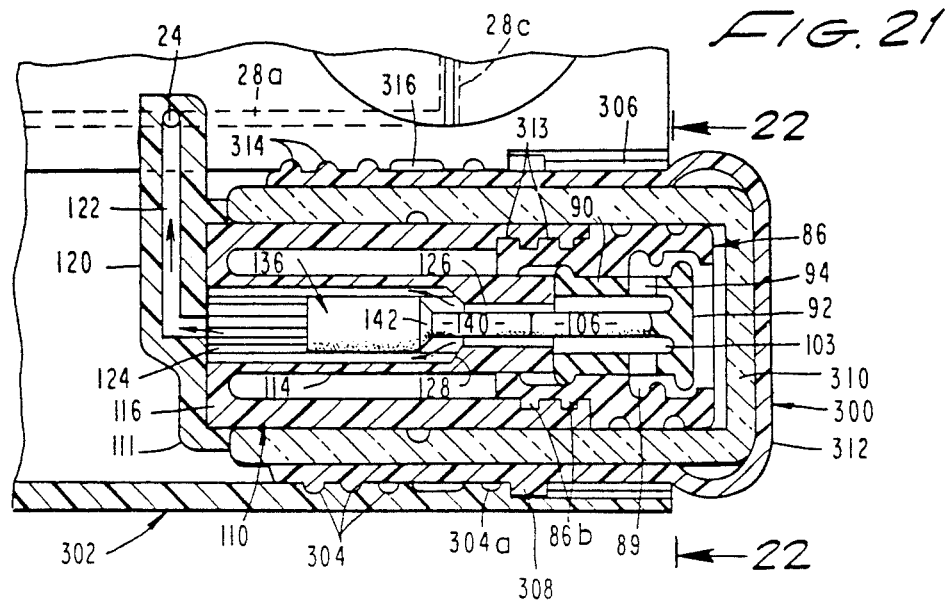
FIG. 21 is a cross-sectional view similar to FIG. 12 showing the transfer step wherein the intermixed fluids are transferred from the drug vial to the reservoir of the infusion portion of the device.

Movement of the drug vial assembly into the position shown in FIG. 21 causes the reconstituted mixture to be transferred back into the infusion device via passageways 94, 103, 126, 124, 122 and 28 for introduction into chamber 30 and further mixing with the diluent and for later infusion into the patient in the manner previously described.

A label covering the peripheral surface of overpackage 12 and joining the forward and rear portions 312f and 312r, can be provided with indicia in the form of numbers, color codes, or the like, to indicate the interconnection, reconstitution and transfer location function of the vial assembly with respect to cylindrical housing 302. Such indicia are useful in training lay persons in the operation of the apparatus.

Referring to FIGS. 23 through 33, another embodiment of the invention is there illustrated. This fourth form of the invention is quite different in overall appearance, but similarly includes a drug vial or container assembly of identical construction and operation to that of container assembly 300 of the third form of the invention. Accordingly, like numerals are used in FIGS. 23 through 33 to identify like container assembly component parts. The coupling members of the coupling means of the present form of the invention are also identical to those previously described in connection with FIGS. 17 through 22. However, the cylindrically shaped first portion of the apparatus housing which houses the coupling means, here identified by the numeral 400, is of slightly different construction, as is the second housing portion that houses the infusion portion of the device. The device of this fourth form of the invention is generally larger than the devices of the earlier described embodiment and is designed to dispense larger volumes of medicaments.

Turning particularly to FIGS. 23, 24 and 25, the second or infusion portion, generally designated by the numeral 402, comprises a base assembly 404 which includes a curved base member 406 having front and back surfaces 408 and 410. The central portion 407 of base member 406 is provided with a multiplicity of small, crossing fluid flow micro-channels 412 which communicate with a longitudinally extending, central collection fluid passageway 414 having spaced-apart portions 413 and 416 (FIG. 29). The function of these channels and parts will be described presently. The side portions 418 of base member 406 are provided with spaced-apart apertures 420 which can be used to grip the device during handling or can accept straps for use in connecting the device to the patients body.

Figure 27:
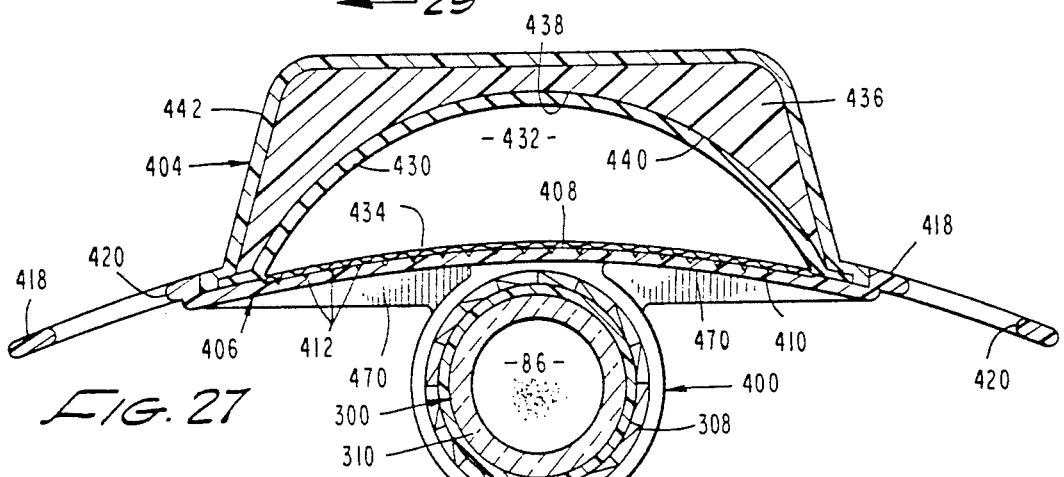
FIG. 27 is a cross-sectional view taken along lines 27—27 of FIG. 26.

A thin, generally planar distendable elastomeric membrane, or member, 430 is termally bound and cooperates with central portion 407 of base 406 to form a chamber 432 (FIG. 27). Member 430 is distendable out of plane in the manner shown in FIG. 27 by the introduction of fluid into the chamber under pressure. As the distendable member 430 is distended by fluid pressure, internal stresses are formed in the member which continuously urge it to return to its original less distended configuration.

Forming an important aspect of this latest form of the apparatus of the invention is the provision of filter means which is disposed internally of chamber 432 for filtering fluids flowing from chamber 432 into fluid passageways 412 formed in base member 406. The filter means also functions as an interfacial bubble trap. In the embodiment of the invention here shown, the filter means is provided in the from of a thin, micro-porous film, laminate or composite membrane 434 which is fitted over the front surface 408 of base 406 in the manner shown in FIG. 27. Front surface 408 provides support means for filter 434. Membrane 434 can be constructed from a wide variety of filtering materials of a character well understood by those skilled in the art, including Cellouous Acetate, Polytetraflouroethylene, Polypropylene, Polyvinylidene Flouride and Polyurethane/Polyethylene Composite.

Superimposed over distendable membrane 430 is a porous plastic, free venting, structural filler member 436. As best seen by referring to FIG. 27, member 436 is provided with a centrally disposed, longitudinally extending, concave channel 438 having an interior wall 440 against which membrane 430 initially engages when it is maximally, outwardly distended by fluid flowing into chamber 432 under pressure. Member 436 can be constructed of the same materials as previously described in connection with member 40.

Extending over and sealably enclosing member 436 is a cover means shown here as a hard plastic cover 442. Cover 442 inclues gas venting means here provided as a plurality of apertures 444 formed within the upper wall of the cover member. When distendable member 430 is constructed of a material of high gas permeability, gas venting means, including apertures 444, permit gases contained within the fluids, if any, then introduced into chamber 432 to pass through the gas permeable membrane, through filler 436 and to atmosphere through the gas venting means. A medicament label 446 having a removable portion, covers vent apertures 444. In certain applications, the cover and base can be constructed of similar materials of the character previously described.

Figure 28:
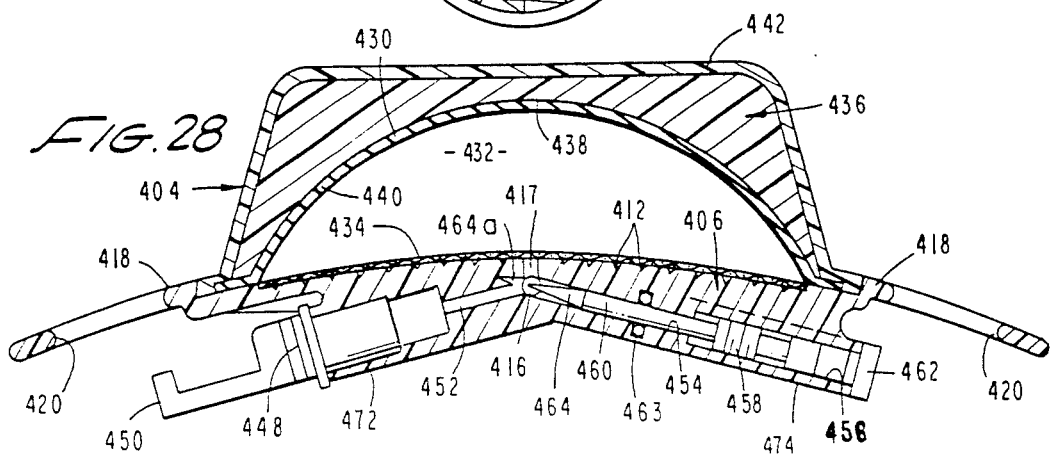
FIG. 28 is a cross-sectional view taken along lines 28—28 of FIG. 26.
Figure 32:
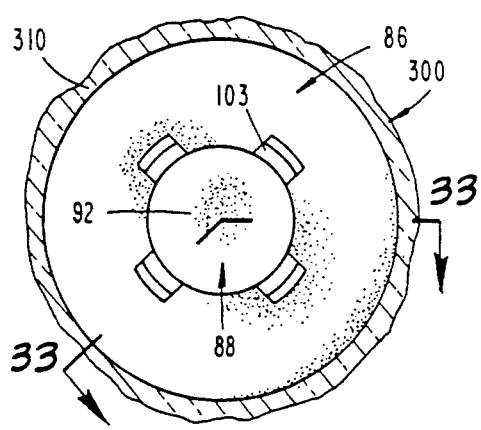
FIG. 32 is a cross-sectional view taken along lines 32—32 of FIG. 30.
Figure 33:
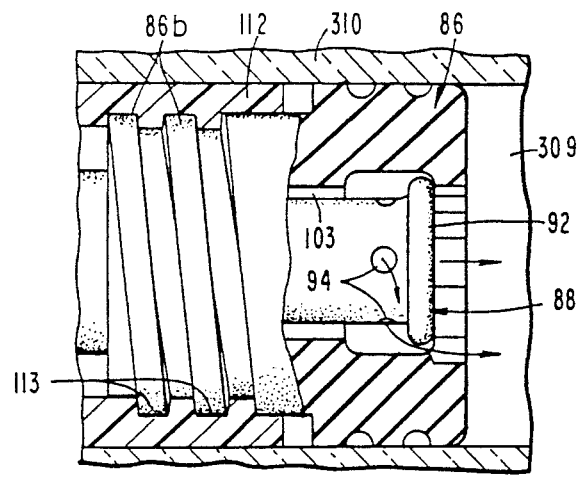
FIG. 33 is a cross-sectional view taken along lines 33—33 of FIG. 32.

Base assembly 404 also includes an outlet or delivery port 448, which is normally closed, by a removable cover member 450. Outlet port 448 is in communication with fluid passageway 414 and an outlet 417 via a conduit 452 (FIG. 28). Outlet port 448 and passageway 452 are also in communication with a transversely extending passageway 454 formed in base 406 which terminates at its outer end in an opening 456 (FIG. 28). Receivable within opening 456 (FIG. 23) is an outlet flow control means shown here as a shut-off and fluid metering means of the character previously discussed herein and identified in FIGS. 2 and 6 by the numeral 63. In the manner previously described, needle valve means 63 functions to either substantially close or to controllably restrict the flow of fluid outwardly of the device through passageway 414 and outlet port 448. As seen in FIG. 28, passageway 454 is internally threaded to threadably receive external threads 458 formed on a stem 460. With this construction, by rotating a control knob 462 attached to stem 460, the valve member can be moved axially of passageway 454 to controllably move tapered portion 464 provided on stem 460 proximate its inner end relative to passageway 454 and into engagement with a valve seat 464a provided in base 406 (FIG. 28). An O-ring 463 is provided to seal stem 460 relative to passageway 454. Alternatively to, or in conjunction with, the needle valve, passageway 452 can be initially sealed by an internal structural septum 465 (FIG. 23) which can be pierced by an I-V administration set piercing spike. This type of recipient port a septum structure is well known in the art.

Figure 26:
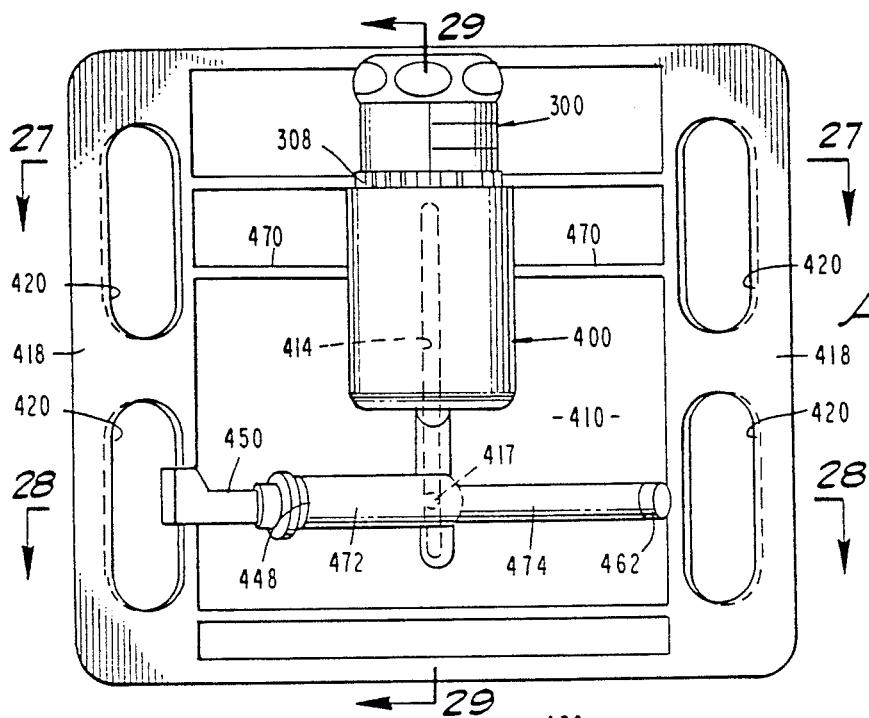
FIG. 26 is a bottom view of the apparatus.

Turning to FIGS. 23 and 29, the construction of the container assembly 300 can be seen to be of similar construction to that shown in FIGS. 17 through 22. The container assembly, the details of construction of which will not be repeated here, is receivable within cylindrical housing portion 400 and the plunger 86 is initially mated with the coupling member 112 in the manner previously described (See also FIGS. 32 and 33). In this latest form of the invention, cylindrical portion 400 is integrally connected to the back or concave surface 410 of base member 406 by means of a connector flange 470 (FIG. 23). Portion 400 also includes a transversing extending base wall 471 having a socket 473 which supports coupling member 112 in a manner bast seen in FIG. 30. Base wall 471 is provided with a passageway 477 which communicates with passageway 124 of coupling member 114 and with passageway 414 of base 402 via port 415. Similarly, an outlet passageway housing 472 and a needle valve housing 474 extend angularly outwardly from back surface 410 (FIGS. 26 and 28). It is to be noted that the front surface 408 of base member 406 is provided with an upstanding mounting boss 475 which surrounds port 415 and to which filter 434 is bonded. Filter 434 is provided with an aperture 434a which peripherally receives boss 475 so that fluid can flow freely through port 415 between channel 414 and chamber 432. (FIG. 25).

In operating the apparatus of this fourth form of the invention, the device is held by one of the side portions 418 and, with the vial closure cap and the cap which closes the passageway of the sterile coupling element 110, removed, the open end of the drug vial assembly 300 is inserted into open end 401 of cylindrical portion 400 (FIG. 23). As best seen by referring to FIGS. 29 and 30, as the drug vial 310 is received within open end 401, threads 314 will move toward a first internal thread 403a provided within cylindrical portion 400. Simultaneously threads 86b will move toward mating engagement with threads 113 provided on coupler member 112. Rotation of the drug vial in a clockwise direction will cause threads 314 to mate with first internal thread 403a and will cause threads 86b on plunger 86 to mate with threads 113 on coupling member 112 in the manner shown in FIG. 30. Teeth 308 provided on overpackage 312 will also move to a location proximate ratchet teeth 405 provided on cylindrical housing portion 400. As the plunger couples with member 112, stem 106 of the container valve will engage stem 140 of valve means 136 simultaneously moving both valve member 137 of the coupling flow control means and valve member 92 of the container flow control means into the open position shown in FIGS. 30 and 33. With the valves of the flow control means in this open position, distendable membrane 430 will cause the fluid contained within chamber 432 to flow under pressure through port 15 (FIGS. 25 and 30) into passageway 477, into passageway 124, past the valve seat 128 into fluid passageway 126 of the coupler means and then into passageway 103 of the container valve means. The fluid under pressure will next flow through radially extending passageways 94 of the container valve and rapidly into the interior 309 of the glass container 310 in the manner shown by the arrows in FIG. 30. This flow of fluid under pressure into the drug vial initiates the mixing or reconstitution process.

As depicted by the arrows in FIG. 30, the fluid flowing into the drug vial will thoroughly mix with the medicament M contained within the vial in the manner shown to form a flowable substance of drug active concentrate comprising a mixture of the diluent stored within changer 432 and the medicament M which was stored within the drug vial.

After the medicament M is mixed with the diluent, the drug vial assembly is once again rotated in a clockwise direction in the manner shown in FIG. 31. During this further rotation, the vial will move through a circumferentially extending space 479 proved within cylindrical portion 400. As before, space 479 functions as a dwell space and is located intermediate first thread 403a and threads 403. Dwell space 479 provides momentary residence time allowing system back-filling and drug reconstitution. Continued clockwise rotation of the drug vial assembly will cause threads 314 to mate with threads 403 moving the drug vial assembly from the position shown in FIG. 30 to the position shown in FIG. 31. Ratchet teeth 308 on the overpackage will also mate with resilient ratchet teeth 405 provided within housing portion 400 so as to substantially lock the vial in position within housing portion 400.

Continued movement of the drug vial assembly into the final position shown in FIG. 31 causes the reconstituted mixture to be substantially transferred back into chamber 432 of the infusion device via passageways 94, 103, 126, 124, 477 and 414 and through port 415 for later controlled infusion of the reconstituted drug active medicament into the patient via the filter 434 and the multiplicity of fluid collection passageways 412, into passageway 414 through port 417 and outwardly of the device through passageway 452 and outlet 448. As previously discussed, the rate of flow fluid through outlet 448 is controlled by the needle valve means 63.

Once again, a label covering the peripheral surface of overpackage 312 is preferably provided with indicia in the form of numbers, color codes or the like to indicate the interconnection, reconstitution and transfer functions of the vial assembly with respect to cylindrical housing 400.

Turning to FIGS. 34 through 38, the latest embodiment of the present invention is shown. This final embodiment is similar in many respects to the embodiment of FIGS. 23 through 33 and like numbers are used to identify like component parts. More particularly, the infusion container portion of the device along with coupling members 112 and 114 are identical to those previously described as is the coupling valve means 136 and the operating means. However, the cylindrical housing portion 500, while mounted on the back surface 410 of the base 406 is of a slightly different construction as is the drug vial assembly 502. The details of construction of these different elements and the method of operation of this last form of the invention will be described in the paragraphs which follow.

Figure 34:
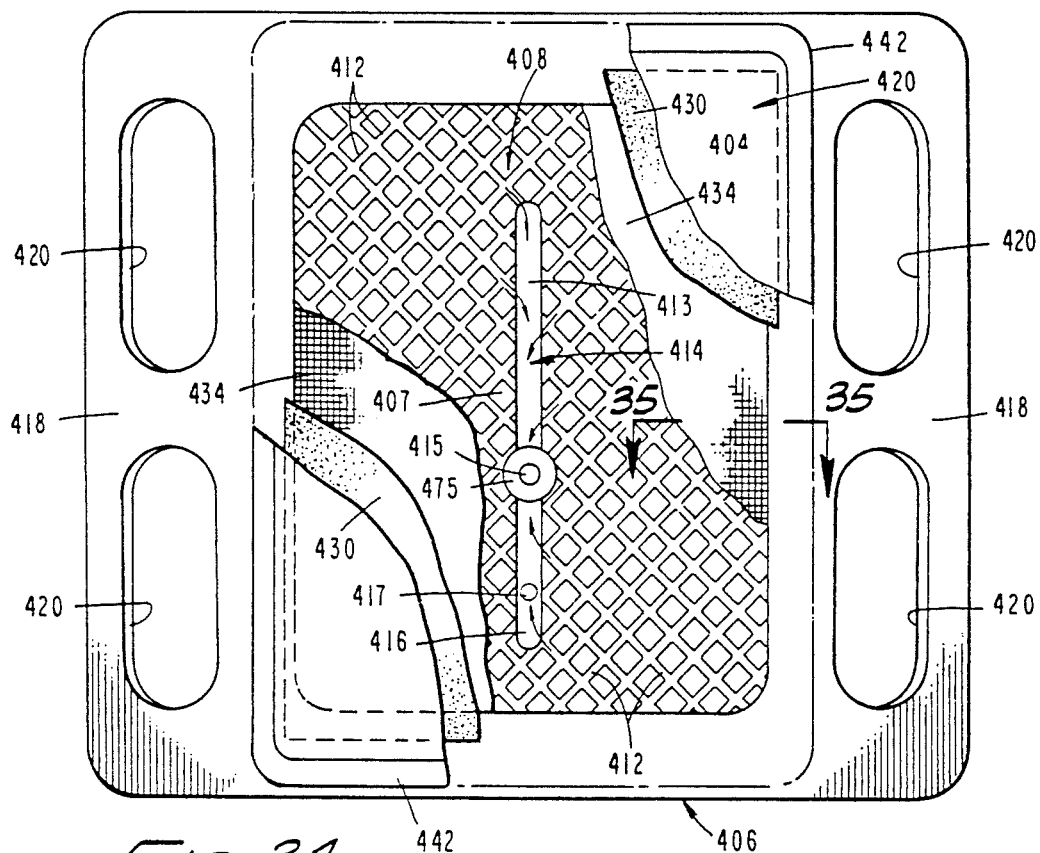
FIG. 34 is a plan view partly broken away to show internal construction of this further form of closed drug delivery apparatus of the present invention.
Figure 35:
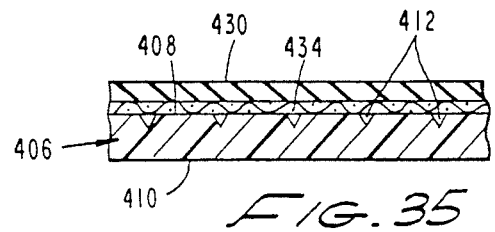
FIG. 35 is a fragmentary cross-sectional view taken along lines 35—35 of FIG. 34.
Figure 36:
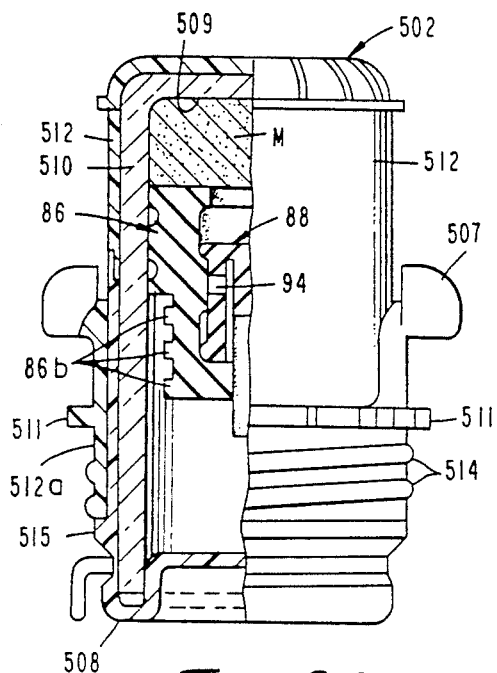
FIG. 36 is a side view, partly in cross-section of the drug vial of this last embodiment of the invention.

Turning first to FIGS. 34 and 35, the base assembly can be seen to be quite similar to that shown in FIG. 25 having a curved base member 406 provided with a multiplicity of flow micro-channels 412 which communicate with a central passageway 414 having spaced-apart portions 413 and 416. Side portion 418 having apertures 420 are as previously described. The apparatus also includes a distendable elastic membrane 430 and filter means 434 which function as before. Turning to FIG. 36, the drug vial or container assembly 502 of this form of the invention, includes second flow control means for controlling the flow of fluid into and out of an internal chamber 509 of a vial 510 which contains the medicament M. The second flow control means of this form of the invention is identical in construction and operation to that previously described and includes a lower durometer plunger 86 which is substantially sealably receivable within vial 510. Plunger 86 also includes connector means, shown as threads 86b, for interconnection with the coupling means of the apparatus. As before, valve assembly 88 controls fluid flow through flow passageways formed within plunger 86 and is operated by operating means of the character previously described.

Vial 510 is enclosed in a multi-part cover, or overpackage member 512 which surrounds vial 510. Overpackage member 512 is, in turn, telescopically received within a collar 512a which includes system interlock stops 511. Provided proximate the lower end of collar 512a are external threads 514 which are adapted to mate with internal threads 504 provided within cylindrical portion 503 of the apparatus housing. Vial 510 is closed by an integral tear-off type closure such as 508 (FIG. 36). Collar 512a is also provided with circumferentially spaced finger grips 507, the purpose of which will presently be described. Overpackage member 512 includes locking means for locking the cover assembly to the cylindrical portion 503. This locking means is here provided in the form of an annular member 515 located proximate the lower end of member 512.

Figure 37:
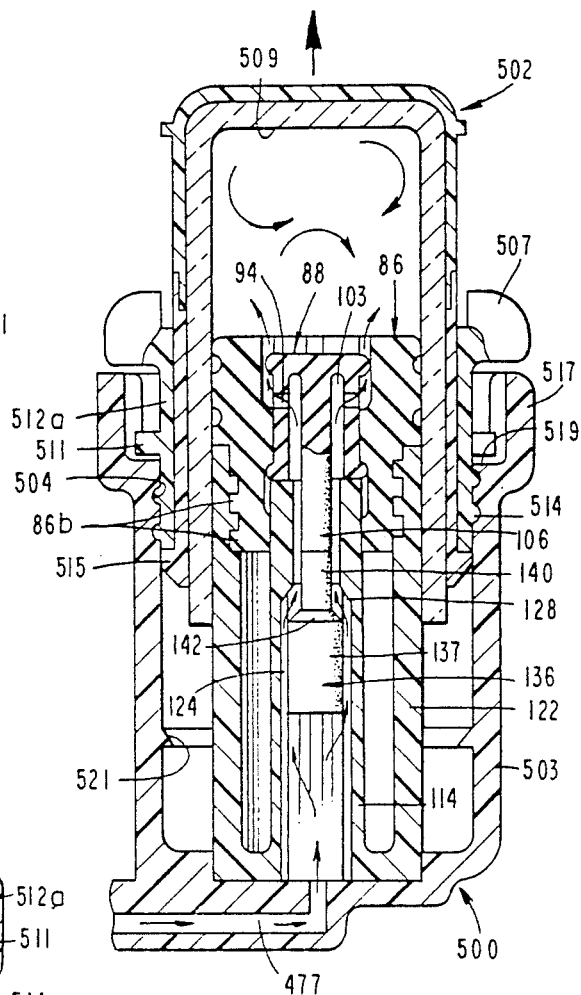
FIG. 37 is a cross-sectional view illustrating the drug vial coupled with the delivery portion of the device to accomplish the initial mixing step.
Figure 38:
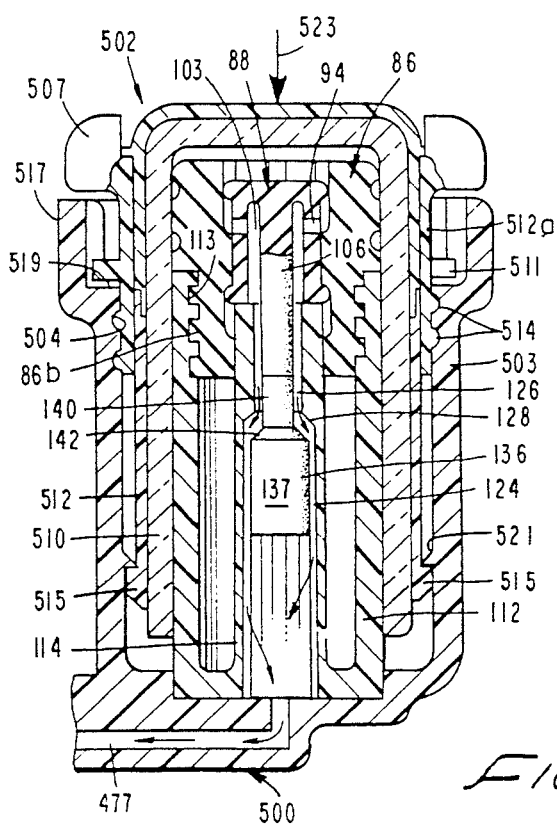
FIG. 38 is a cross-sectional view showing the transfer of the intermixed fluids within the drug vial to the reservoir of the infusion portion of the device.

Turning to FIG. 37, cylindrical portion 502 of the housing of this latest form of the invention has an enlarged diameter mouth 517 which is adapted to receive stops 511 and which defines a radially extending annular surface 519 against which stops 511 engage. Longitudinally spaced apart from surface 519 is a circumferentially extending, inwardly protruding annular stop member 521 which, in a manner presently to be described, is adapted at the completion of the cycle, to lockably engage annular member 515 provided on overpackage member 512.

In operating the apparatus of this final form of the invention, vial closure 508 is first removed from the drug vial assembly 300. This done, the open end of the drug vial assembly 502 is inserted into sterile mouth 517 of cylindrical portion 503 (FIG. 37). Using finger grips 507 from control, threads 514 are threadably mated with internal threads 504 provided within cylindrical portion 503. Vial assembly 502 is then pushed forward to move threads 86b on plunger 86 into proximity with threads 113 provided on coupler member 112. Further rotation of the drug vial in a clockwise direction, using grips 507, will then cause threads 86b on plunger 86 to mate with threads 113 on coupling member 112 in the manner shown in FIG. 37. As the plunger couples with member 112, stem 106 of the container valve will engage stem 140 of valve means 136 simultaneously axially moving both valve element 137 of the first flow control means and valve member 88 of the second flow control means into the open position shown in FIG. 37. With the valves of the flow control means in this open position, distendable elastic membrane 30 will cause the fluid contained within chamber 432 to flow under pressure through port 415, into passageway 477, into passageway 124, past the valve seat 128 into fluid passageway 126 of the coupler means and then into passageway 103 of the container valve means. The fluid under pressure will next flow through radially extending passageways 94 of the container valve and rapidly into the interior of the container 510 in the manner shown by the arrows in FIG. 37. This flow of fluid under pressure into the drug vial initiates the mixing or reconstitution process and causes the container assembly to move outwardly (upwardly as shown in FIG. 37).

In all forms of the invention previously described, the plunger of the container valve is preferably constructed from a rubber or silicon material. The valve member which reciprocates within the plunger is preferably constructed of higher durometer rubber or silicon, or from glass or plastic materials such as polypropylene, polycarbonate, polystyrene, ABS, PTFE or high density teflon or nylon. Similarly, valve member 137 is preferably constructed from silicon rubber, rubber, flexible PVC, polyurethane, PTFE, or fluorsilicon elastomers.

Referring now to FIGS. 39 through 53, still another embodiment of the invention is shown. In this embodiment, the construction of the cylindrical housing portion 600 and the base assembly 604 are of similar construction to housing portion 400 and base assembly 406 shown in FIGS. 23 through 28 and like numbers are used to designate like components. However, the container assembly, the details of construction of which will presently be described, is of a somewhat different construction. More particularly, the apparatus of this new form of the invention uniquely permits controlled intermixing of the diluent or other parenteral fluid with the medicament by providing flow rate control means for precisely controlling the rate of fluid flow between the storage reservoir and the medicament mixing chambers.

Figure 39:
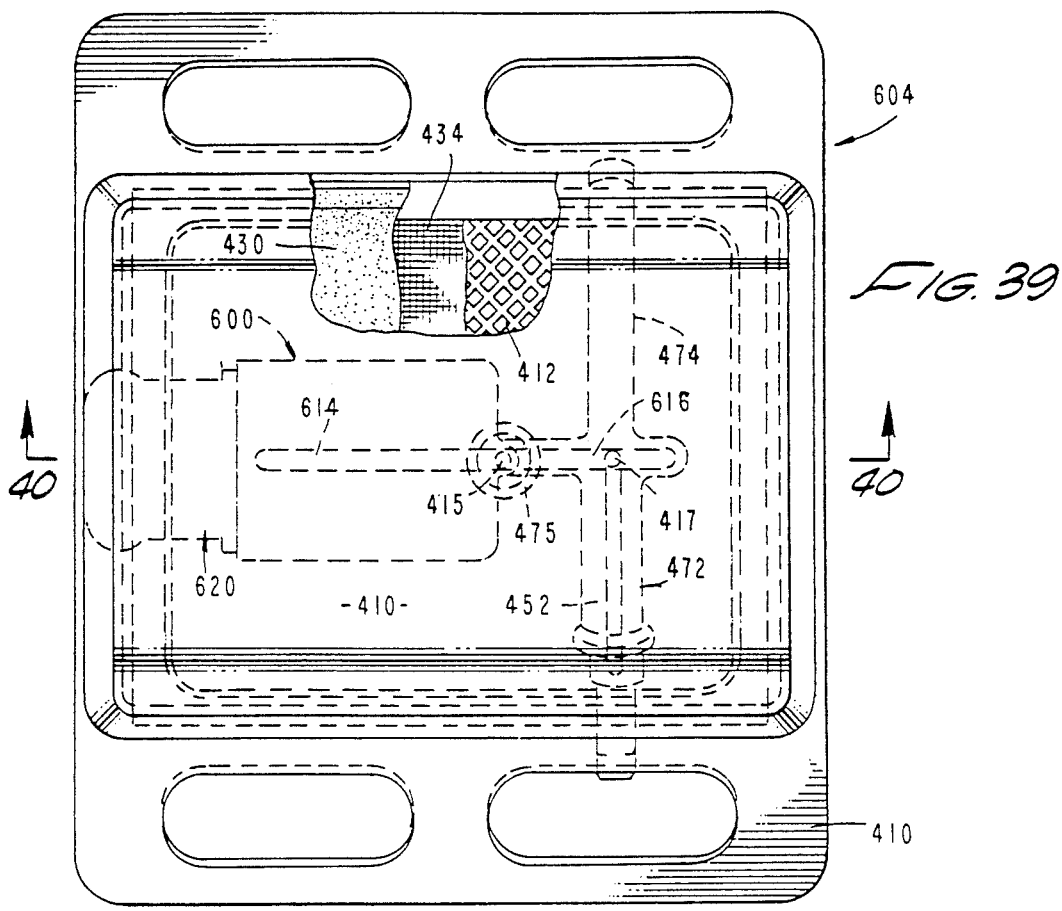
FIG. 39 is a plan view partly broken away to show internal construction, of yet another embodiment of the drug delivery system of the invention.
Figure 40:
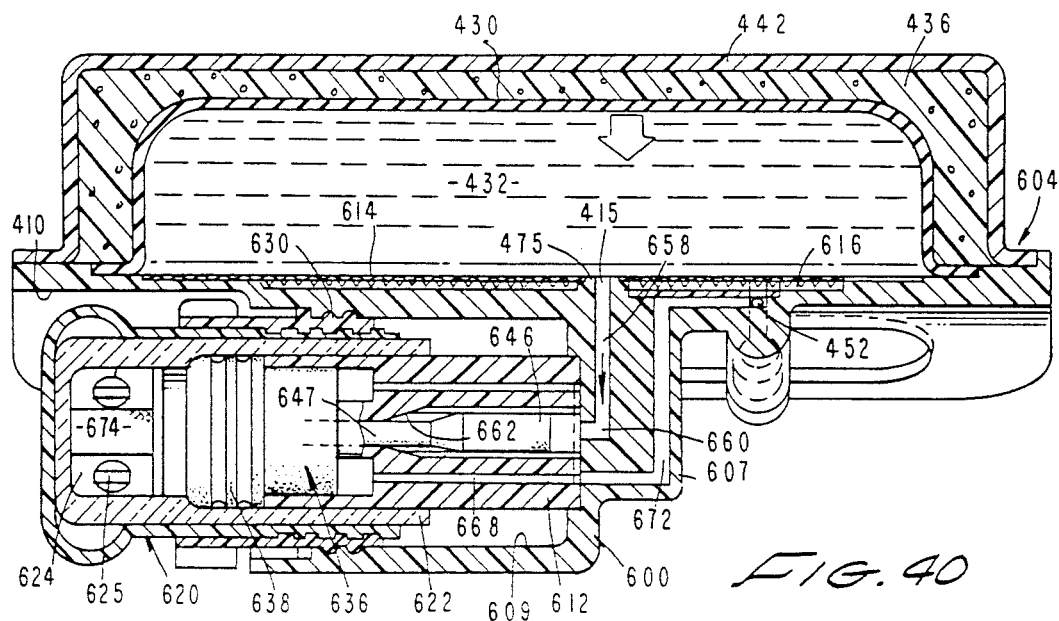
FIG. 40 is a cross-sectional view taken along lines 40—40 of FIG. 39.

In this latest form of the invention, cylindrical portion 600 is integrally connected to the back or concave surface 410 of the base member by means of a connector flanges 470 (FIG. 23). Portion 600 also includes a transversing extending base wall 607 having a socket 609 which supports a coupling member 612 in a manner best seen in FIG. 40. Base 406 is provided with longitudinally extending passageways 614 and 616. Passageway 614 communicates with storage reservoir 432 and with port 415. Passageway 616 communicates with the outlet port of the device formed in outlet passageway housing 472. Similarly, a needle valve housing 474 of the character previously described extends angularly outwardly from back surface 410 (See also FIGS. 26 and 28). It is to be noted that the front surface of the base member is provided with crossing micro flow channels 412 and with an upstanding mounting boss 475 which surrounds port 415 and to which a filter membrance 434 is bonded (FIG. 39). Filter means and micro flow channels 412 function in the same manner to accomplish the same result as previously described herein.

Referring now to FIGS. 41 and 42, the container assembly 620 of this form of the invention comprises a glass vial 622 having a chamber 624 for containing a medicament which may be an extended time release medicament, which is here shown as capsules or tablets 625. A plastic cover or overpackage 626 is closely received over vial 622 and includes a metering thread 627 (FIG. 53), the purpose of which will presently be described. Surrounding cover 626 is a collar 628 having external threads 630 and system interlock stops 632. Threads 630 are adapted to mate with internal threads 634 provided on cylindrical portion 600. Housed within vial 622 is the flow control means of this form of the invention for substantially controlling the flow of fluid into and out of mixing chamber 624. Here the flow control means comprises a plunger 636 sealably received within vial 622. Plunger 636 is of generally similar construction to previously described plunger 86 being cylindrical in shape and having a skirt portion 638 adapted to sealably engage the inner wall of vial 622 (FIG. 44).

Figure 50:
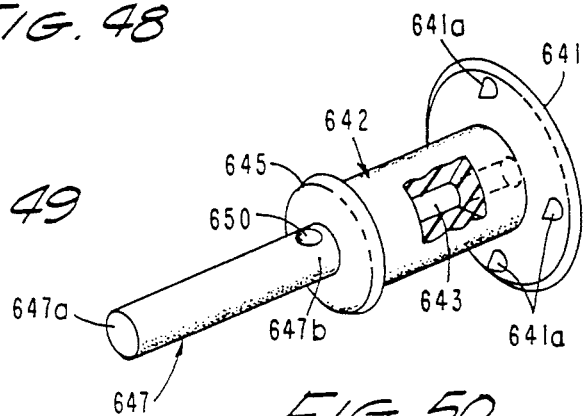
FIG. 50 is a fragmentary, generally perspective view of the fine control valving means of the drug vial of this further embodiment.

Plunger 636 is provided with a centrally disposed bore 639 and a plurality of circumferentially spaced fluid passageways 640. An inlet or fine flow control valve member 642 also forms a part of the flow control means and includes a centrally disposed inlet passageway 643. Member 642 is reciprocally movable within bore 639 and is provided with a first flange portion 641 which functions to control fluid flow through passageways 640. Member 642 also includes a second or inboard flange 645 which guides the travel of the valve member within an annular channel 636a provided within plunger 636. Valve member 642 further includes a stem 647 which, in a manner presently to be described, cooperates with a check valve 646 carried within an internal passageway 649 provided in coupling member 612 (FIG. 43). Stem 647 forms an integral part of the valve member 642 and terminates at an in-board end 647a. Proximate the opposite end 647b of stem 647 is a transverse fluid passageway 650 which permits fluid flowing past check valve 646 to enter inlet passageway 643 (FIG. 50).

In operating the apparatus of this latest form of the invention, the vial closure cap 651 and the cap 652 which closes the passageway of the drug vial (FIGS. 43 and 44) are first removed. The open end 653 of the drug vial assembly is then ready to be inserted into end 601 of cylindrical portion 600 (FIG. 45) which in some instances may be closed began sterile peal away closure seal (not shown). As best seen by referring to both FIGS. 43 and 44, as the drug vial assembly 620 is received within open end 601 of the infusion portion of the apparatus, threads 630 will move toward engagement with a first internal thread 634a provided within cylindrical portion 600. By griping finger grips 654 of collar 628 the drug vial can be rotated in a clockwise direction causing the drug vial to advance within cylindrical portion 600 to the position shown in FIG. 45. At this secured position, system interlock steps 632 will move toward locking engagement with an internal shoulder 655 provided on cylindrical housing portion 600. As the drug vial thus mates with cylindrical portion 600, stem 647 of valve member 642 will move into proximity with check valve 646.

Turning now to FIG. 45, it is to be observed that clockwise rotation of vial 620 relative to collar 628 will cause stem 644 to engage check valve 646. Because of the pressure being exerted on valve 646 by the fluid in the reservoir, movement of the check valve to the open position will be resisted. Accordingly operating valve 642 will move to the left to the position shown in FIG. 45. However, when flange 645 seats against shoulder 636a on plunger 636, continued clockwise rotation of the vial within collar 628 will cause stem 644 to move the check valve 646 to the left into the open position shown in FIGS. 45. With the check valve of the flow control means in this open position, distendable membrane 430 will cause the fluid contained within chamber 432 to flow under pressure through port 415 (FIGS. 40 and 45) into passageway 658, then into passageway 660, past the valve seat 662 into fluid passageway 664 of the coupling member and then into central passageway 643 of the inlet valve member 642. The fluid under pressure will next flow rapidly into the medicament chamber 624 of the glass container in the manner shown by the arrows in FIG. 45. This flow of fluid under pressure into chamber 624 causes controlled diluent flow around capsules 625 and initiates the controlled mixing or reformulation process to produce the beneficial agent to be infused into the patient.

Referring particularly to FIG. 45, it is to be noted that rotation of vial 620 relative to collar 628 not only opened check valve 640 but also caused flange 641, including protuberances 641a of member 642 to move from the position shown in FIG. 44 wherein fluid flow through passageways 640 of plunger 636 was blocked to the open flow position shown in FIG. 45. This movement of valve 642 to the right as shown in FIG. 45 permits fluid to flow rearwardly from medicament chambers 624 into passageways 640 of plunger 636 in the manner shown by the arrows 665 in FIG. 45.

With valve member 642 in the position shown in FIG. 45, the mixed solution, or beneficial agent, will continue to flow under pressure through passageways 640, into passageways 668 formed in coupling member 612, into annular collector passageway 670 (FIG. 47) into passageway 672 formed in cylindrical portion 600 and thence to the outlet port via passageway 452. A filter member 674 is provided within medicament chambers 624 to filter out particulate matter prior to the dispensing of the reformulate dbeneficial agent from the device.

Figure 48:
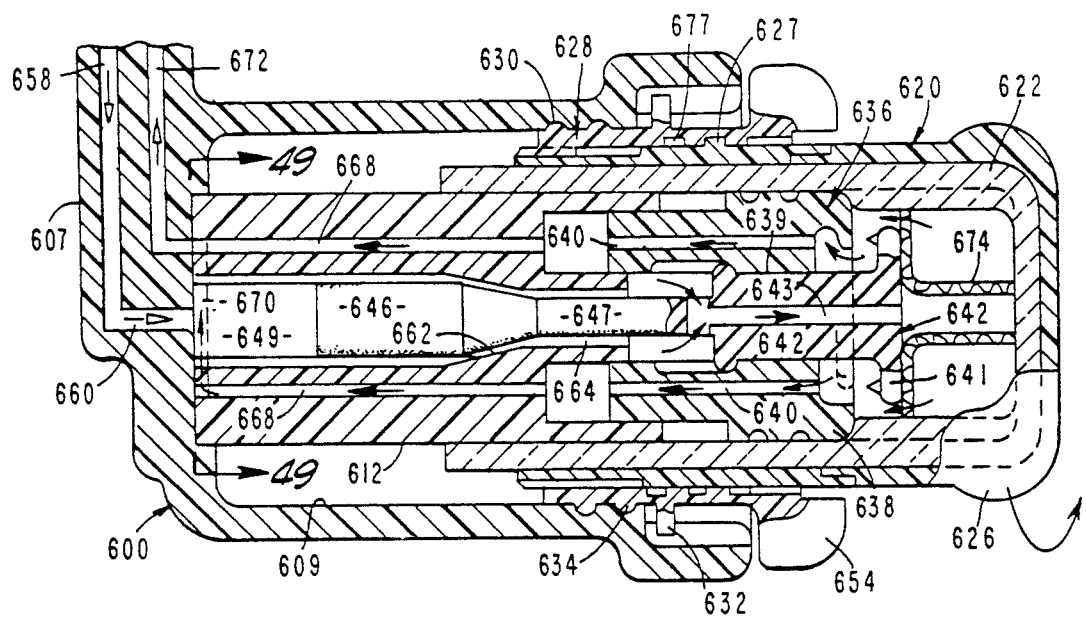
FIG. 48 is an enlarged cross-sectional view similar to FIG. 45 showing further rotation of the drug vial in a manner to throttle down the flow of fluid toward the mixing chamber of the drug vial.
Figure 49:
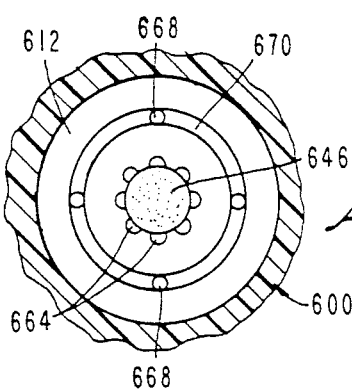
FIG. 49 is a cross-sectional view taken along lines 49—49 of FIG. 48.
Figure 51:
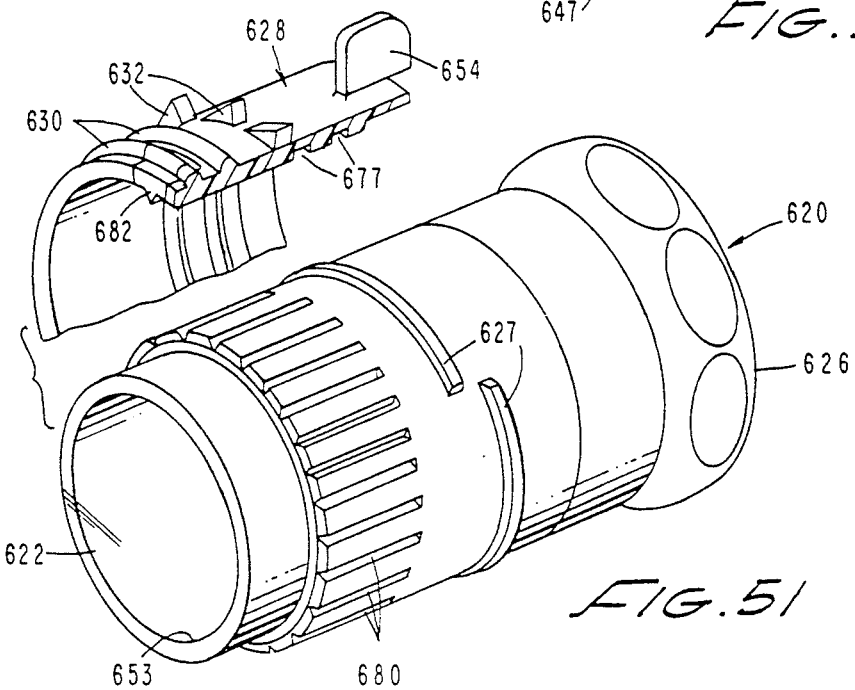
FIG. 51 is an enlarged, generally perspective exploded view of the drug vial illustrating the construction of the fine flow control adjustment means of the invention.

After commencement of the controlled mixing of the medicament with the diluent, the rate of flow of the diluent from the reservoir 432 toward the drug vial and back toward the reservoir can be precisely regulated by counter clockwise rotation the drug vial relative to metering threads 677 provided on collar 628 in the manner illustrated in FIG. 48. This counter clockwise rotation of the vial as indicated in FIG. 48 causes the check valve 646 to move toward the closed position shown in FIG. 48 tending to throttle fluid flow toward the mixing chamber. In this way fluid flow toward the mixing chamber 624 can be precisely controlled. Referring to FIGS. 47 and 51, it is to be noted that vial overpackage 626 is provided with a plurality of circumferentially spaced grooves 680 while collar 628 is provided with a radially inwardly extending rib 682. As the vial is rotated relative to the collar, the rib 682 will sequentially engage the grooves causing a clicking sound and permitting very fine rotational adjustments to be made. As shown in FIG. 41, overpackage 628 is provided with a pointer 684 which indexes with indicia 686 which may be color coded to show fluid flow rate bused on the position of the vial relative to the collar. Ratchet teeth can also be provided on the overpackage to mate with resilient ratchet teeth provided within housing portion 600 so as to substantially lock collar 628 in position within housing portion 600 as the flow rate adjustments are made.

Referring now to FIGS. 52 through 62, yet another embodiment of the invention is shown. In this embodiment, the construction of the infusion portion of the device including the cylindrical housing portion and the base assembly are of identical construction to that of the embodiment of the invention shown in FIGS. 39 through 51 and like numbers are used to designate like components. However, once again the container assembly, the details of construction of which will presently be described, is of a somewhat different construction. As was the case with the embodiment of FIGS. 39 through 51, the apparatus of this latest form of the invention also uniquely permits controlled intermixing of the diluent or other pareteral fluid with the medicament by providing flow rate control means for precisely controlling the rate of fluid flow between the storage reservoir and the medicament mixing chambers.

Referring particularly to FIGS. 52 and 53, the container assembly 720 of this form of the invention comprises a glass vial 722 having a chamber 724 for containing a medicament which is here shown as dissolvable drug compounds 725. A plastic cover or overpackage 726 is closely received over vial 722 and includes a metering thread 727 (FIG. 53), the purpose of which will presently be described. Surrounding cover 726 is a collar 728 having external threads 730 and system interlock stops 732. Threads 730 are adapted to mate with internal threads 634 provided on cylindrical portion 600 (FIG. 55). Housed within vial 722 is the slightly differently configured flow control means of this latest form of the invention for controlling the flow of fluid into and out of mixing chamber 724. Here the flow control means comprises a plunger 736 sealably received within vial 722. Plunger 736 is of generally similar construction to previously described plunger 86 being cylindrical in shape and having a skirt portion 738 adapted to sealably engage the inner wall of vial 722 (FIG. 55).

Plunger 736 is provided with a centrally disposed bore 739 and a plurality of circumferentially spaced fluid passageways 740. An inlet or fine flow control valve member 742 of slightly different construction also forms a part of the flow control means. Member 742 is reciprocally movable within bore 739 and is provided with a first flange portion 741 which functions to control fluid flow through passageways 740. Member 742 also includes a second or inboard flange 745 which guides the travel of the valve member within an annular channel 736a provided within plunger 736. Valve member 742 also includes a stem 747 which is disposed within a central flow passageway 742a and which, in a manner presently to be described, cooperates with a check valve 746 carried within an internal passageway 749 provided in coupling member 612 (FIG. 55). Stem 747 forms an integral part of the valve member 742 and terminates at an inboard end 747a (see also FIG. 61) Proximate the opposite end of stem 747 is an enlarged diameter portion 747b which terminates in the previously identified flange 741. Extending angularly through portion 747b are circumferentially spaced fluid passageways 750 which, in a manner presently to be described, permit fluid flowing past check valve 746 to enter chamber 724. (FIG. 56). Enlarged diameter portion 747b is also provided with circumferentially spaced, radially extending flow passageway 742b.

In operating the apparatus of this latest form of the invention, the vial closure cap 651 and the cap 652 which closes the passageway of the drug vial (FIGS. 54 and 55) are first removed. The open end 753 of the drug vial assembly is then ready to be inserted into open end 601 of cylindrical portion 600 which may also have been previously sealed by a removable cover (not shown) (FIG. 54). As best seen by referring to both FIGS. 54 and 55, as the drug vial assembly is received within open end 601 of the infusion portion of the apparatus, threads 730 will move toward engagement with a first internal thread 634a provided within cylindrical portion 600. By griping finger grips 754 of collar 728 the drug vial can be rotated in a clockwise direction causing the drug vial to advance within cylindrical portion 600 to the position shown in FIG. 55. At this position, system interlock steps 632 will move toward locking engagement with an internal shoulder 655 provided on cylindrical housing portion 600. As the drug vial thus mates with cylindrical portion 600, stem 747 of valve member 742 will move into proximity with check valve 746.

Turning now to FIG. 56, it is to be observed that clockwise rotation of vial 720 relative to collar 728 will cause stem 747 to engage check valve 746. Because fluid under pressure within the reservoir resists movement of the check valve, operating valve 742 will move to the left to the position shown in FIG. 56. However, when flange 745 seats against internal shoulder 736a of plunger 736, continued clockwise rotation of vial 720 within collar 728 will cause stem 747 to move check valve 746 to the left into the open position shown in FIG. 56. With the check valve in this open position, distendable membrane 430 will cause the fluid contained within chamber 432 .to flow under pressure through port 415 (FIGS. 40 and 46) into passageway 658, then into passageway 660, past the valve seat 762 into fluid passageway 664 of the coupling member and then into central passageway 742a of the inlet or operating valve member 742. The fluid will then flow into passageways 742b and 750 and then vigorously into mixing chamber 724. (See also FIGS. 59 and 60). This flow of fluid under pressure into chamber 724 causes controlled diluent flow through and around drug compound 725 as shown in FIG. 56 and initiates the mixing or reformulation process to produce the beneficial agent to be infused into the patient.

Referring particularly to FIG. 55, it is to be noted that so long as valve member 742 is in the position there shown, flange 741, including protuberances 741a as provided thereon, will block fluid flow through passageways 740 of plunger 736. However, as previously mentioned, clockwise rotation of the vial assembly 720 within the overpackage 726 will cause valve member 742 will move to the right due to the urging of check valve 746. So long as member 742 is in the position shown in FIG. 56, The mixed solution, or beneficial agent, will continue to flow under pressure in a reverse direction toward reservoir 432 through passageways 740, into passageways 668 formed in coupling member 612, into annular passageway 670 (FIG. 49) into passageway 672 formed in cylindrical portion 600 and thence to reservoir 432. As before a filter member 774 is provided within medicament chambers 724 to filter out particulate matter prior to the beneficial agent being dispensed from the device.

After commencement of the mixing of the medicament or drug 725 with the diluent, the rate of flow of the diluent from the reservoir 432 toward the mixing chambers of the drug vial and outwardly of the device can be precisely regulated by rotating the drug vial in a counter clockwise direction relative to metering threads 777 provided on collar 728 in the manner previously described and as illustrated in FIG. 58.

Refering to FIG. 62, the mixing chamber 747 is shown to contain a medicament in the form of a dissolvable tablet 725a. This tablet is comprised of a beneficial agent such as a muscle relaxant.

Turning now to FIGS. 63 through 67, still another embodiment of the invention is shown. In this embodiment, the construction of the cylindrical housing portion 800 and the base assembly 804 are of similar construction to housing portion 400 and base assembly 406 shown in FIGS. 23 through 28 and like numbers are used to designate like components. However, the container assembly, the details of construction of which will presently be described, is of a somewhat different construction. More particularly, the apparatus of this latest form of the invention uniquely permits controlled intermixing of a first component such as a diluent, solvent or other parenteral fluid with an additive such as a medicament or other beneficial agent which is presented to the first component by a unique adding means, the character of which will presently be described.

In the paragraphs which follow, wherein the details of this unique intermixing process will be discussed, the following terms will have the following meanings:

Element—any of the fundamental substances that consist of atoms of only one kind and that singly or in combination constitute all matter.

Additive—the element, compound, substance, agent, biologically active material, or other material which is to be added, all or in part, to the fluid introduced into the device of the invention.

Polymer—a chemical compound or mixture of compounds formed by polymerization and consisting essentially of repeating structural units.

Parenteral Fluid—any solution which may be delivered to a patient other than by way of the intestines, including water, saline solutions, alkalizing solutions, dextrose solutions acidifying solutions, electrolyte solutions, reagents, solvents and like acquous solutions.

Beneficial Agents—any drug, medicament, pharmaceutical, medical polymer, enzyme, hormone, antibody, element, chemical compound or other material useful in the diagnosis, cure, mitigation, treatment or prevention of disease and for the maintenance of the good health of the patient.

Biologically Active Material—a substance which is biochemically, Immunochemically, physiologically, or pharmaceutically active or reactive. Biologically active material includes at least one or more of the following: biochemical compounds (such as amino acids, carbohydrates, lipids, nucleic acids, proteins, and other biochemicals and substances which may complex or interact with biochemical compounds), such biochemical compounds biologically functioning as antibodies, antigenic substances, enzymes, cofactors, inhibitors, lectins, hormones, hormone producing cells, receptors, coagulation factors, growth enhancers, histones, peptides, vitamins, drugs, cell surface markers and toxins, among others known to those skilled in the art. Of the group of biologically active materials described, proteins are of utmost current interest because of the large molecule genetically engineered biopharmaceuticals as those species to be immobilized and congregated on the additive carriers hereinafter to be described. A discussion of the use of biomosaic polymers as carriers for biologically active materials is set forth in European Patent Application 0,430,517 A2.

Adding Means—an additive and any means for presenting the additive to the fluid flowing through the fluid passageways of the fluid delivery device of the invention in a manner such that all or any part of the additive will be added to the fluid. The adding means comprises the additive and the additive presentation means which may take the form of a functional support, or carrier, an anchorage, a deposition or reaction site or an element holder with or without some type of intermediate matrix or other release composition.

Additive Presentation Means—Any means such as a functional support or substrate for presenting the additive to the fluid flowing through the device. The functional substrate can comprise a polymer, copolymer, an inter-polymer, a ceramic, a crystal sponge, a carbon based matrix, a celullosic, glass, plastic, biomosaic polymers, azlactone-functional polymer beads, adduct beads, carboxylate-functional polymer beads, gums, gels, filaments and like carriers.

The adding means of the invention can take several different forms such as those illustrated in FIG. 66. However, in its preferred form, the adding means comprises a cylindrically shaped, microporous polymeric functional support structure which is disposed within the mixing chamber of the container assembly and to which various additives, including beneficial agents such as drugs, biologically active materials, and chemical elements and compounds can be releasably connected. These additives are carried by the structure in a manner such that, as the liquid, such as a diluent, reagent, or other aqueous solvent flows around, about and through the support assembly in the manner shown by the arrows in FIG. 64, the additives will be presented to the liquid flow and efficiently released and added to the liquid as it flows through the chamber which houses the adding means.

The additives themselves can also take various physical forms including .liquid, solid, granular, powder, particle, gel, wax, hydrocolloid carrier, a gum, film, tablet, crystalline, emulsions, microcrystalline, microspherical, spray dried compounds and lypohilized compounds and saturants. The additives can be removably connected to, immobilized on, impregnated within or supported by the support means in a number of ways. The additives can be chemically or mechanically attached, affixed, or bound directly or indirectly through cooperation with an intermediate matrix. They can be captured, affixed, linked or cross linked, anchored to the surfaces of the support, or surface active agent, or they can be absorbed, reaction catalyzed, electrostatically encapsulated, attached by chemical modification in to the carrier surface, polymerized on or through the carrier, localized, entrapped, deposited, suspended or occluded within voids, cells, tubules, and intersticies formed in the support. One important method for removably affixing the additive to the functional support means includes treating the functional support means with a compound having reactive functional groups such as azlactone functional compounds with their high binding capacity. In certain applications, the biologically active material can be bound at the surfaces of biomosaic polymers in the manner described in EPO Patent No. 0 430 517 A2. Similaraly, graft copolymers can be used in the manner described in U.S. Pat. No. 5,013,795 issued to Coleman, et al. In this way complexing agents, catalysts and biological materials such as enzymes or other proteins as well as biomacromolecules can be attached to the carrier.

Similarly, the additives can be immediately separated from the functional support and added to or intermixed with the liquid flowing through the device by one or more of various mechanisms, including chemical reaction, dissolution, debinding, delinking, displacement, bioseparation, diffusion, washing, disintegration, errosion, dissassociation, desorbsion, solubilization, leeching, enzymatic cleavage, biological reaction, osmosis, separation from ring opening materials by a ring .opening reaction and like separation means.

Turning particularly to FIG. 66 various forms of adding means, or additive carriers are there illustrated. These additive carriers are disposed within the container assembly of the invention, the construction of which will now be described.

Figure 63:
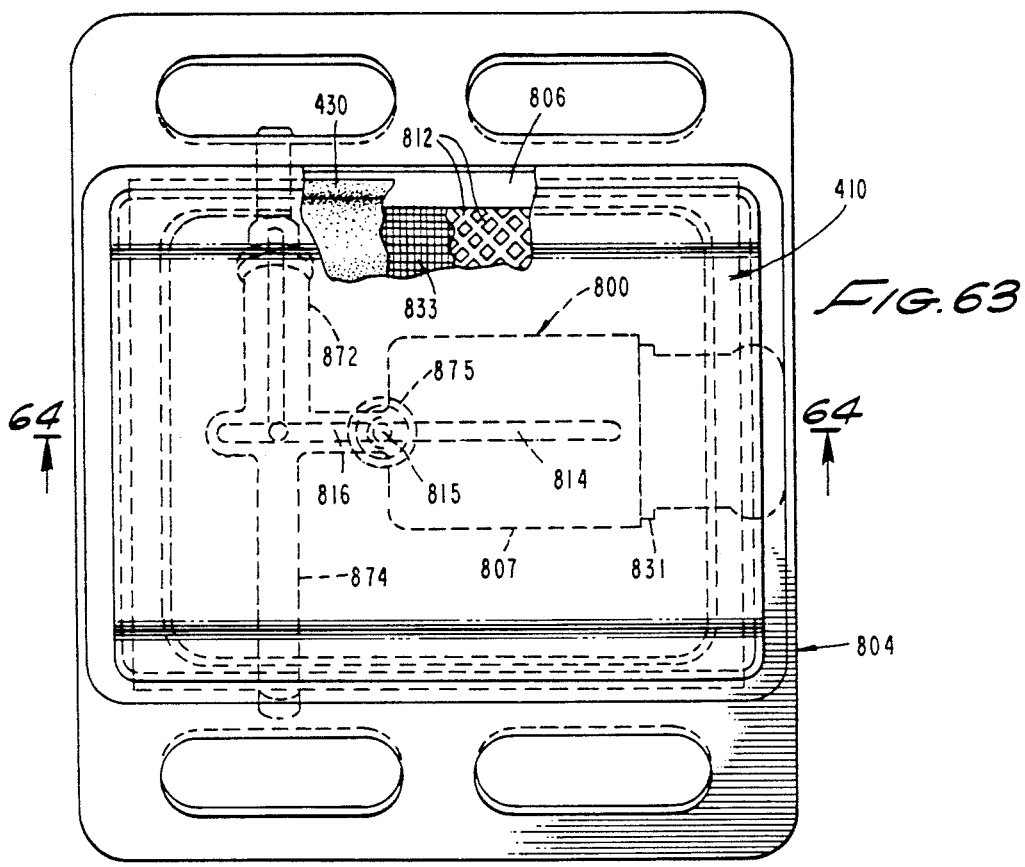
FIG. 63 is a plan view of yet another form of the drug vial assembly of the present invention.
Figure 64:
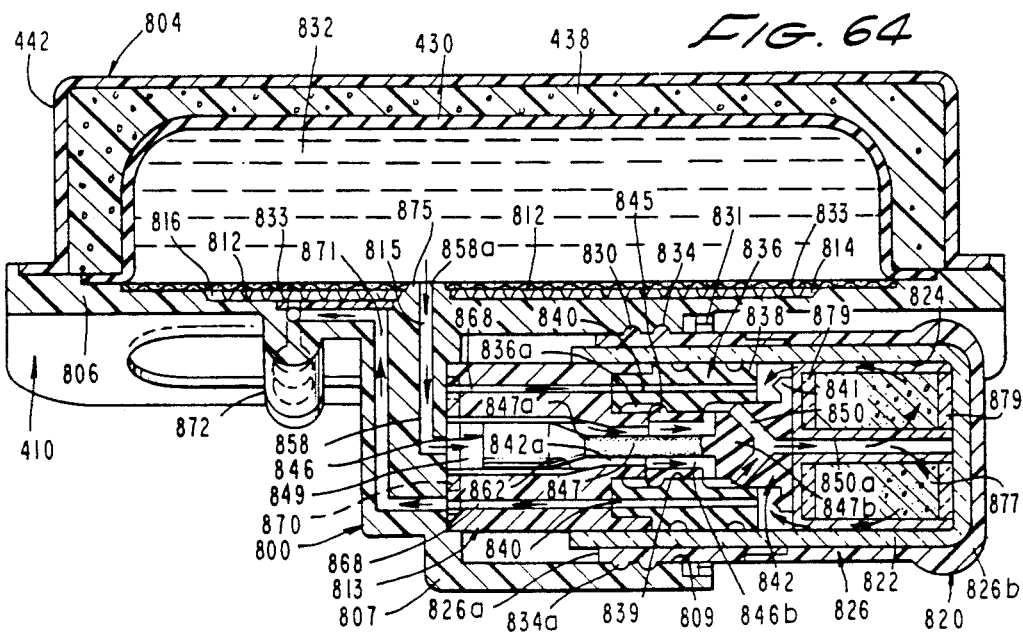
FIG. 64 is a cross-sectional view taken along lines 64—64 of FIG. 63.

As best seen in FIGS. 63 and 64, in this latest form of the invention, cylindrical portion 800 is integrally connected to the back or concave surface 410 of the base member by means of connector flanges 470 (FIG. 23). Portion 800 also includes a transversing extending base wall 807 having a socket 809 which supports a coupling member 812 in a manner best seen in FIGS. 40 and 64. Base 806 is provided with longitudinally extending passageways 814 and 816. Passageway 814 communicates with storage reservoir 832 and with port 815. Passageway 816 communicates with the outlet port of the device formed in the outlet passageway housing 872. This passageway can also be used to aseptically prefill the reservoir during the manufacturing process. Similarly, a needle valve housing 874 of the character previously described extends angularly outwardly from back surface 410 (See also FIGS. 26 and 28) and carries the second flow control means of the invention for controlling the flow of fluid through the fluid outlet of the base assembly. It is to be noted that the front surface of the base member is provided with crossing micro flow channels 812 and with an upstanding mounting boss 875 which surrounds port 815 to which a filter membrane 834 is bonded (FIG. 63). Filter means and micro-flow channels 812 function in the same manner to accomplish the same result as previously described herein.

Referring particularly now to FIG. 64, the container assembly 820 of this form of the invention is there shown and comprises a glass vial 822 having a fluid flow passageway therethrough and walls defining a mixing chamber 824 in communication with the fluid flow passageway. Chamber 824 functions to contain the adding means of this latest form of the invention. A two-part plastic cover or overpackage 826 is closely received over vial 822. Cover 826 includes first and second portions 826a and 826b. Portion 826a is provided with external threads 830 and system interlock stops 831. Threads 830 are adapted to mate with internal threads 834 provided on cylindrical portion 800 (FIG. 64). Housed within vial 822 is the first flow control means of this form of the invention for substantially controlling the flow of fluid into and out of mixing chamber 824. Here the first flow control means comprises a plunger 836 sealably received within vial 822. Plunger 836 is of generally similar construction to previously described plunger 86 being cylindrical in shape and having a skirt portion 838 adapted to sealably engage the inner wall of vial 822 (FIG. 64).

Plunger 836 is provided with a centrally disposed bore 839 and a plurality of circumferentially spaced fluid passageways 840. An inlet or fine flow control valve member 842 also forms a part of the flow control means. Member 842 is reciprocally movable within bore 839 and is provided with a first flange portion 841 which functions to control fluid flow through passageways 840. Member 842 also includes a second or inboard flange 845 which guides the travel of the valve member within an annular channel 836a provided within plunger 836. Valve member 842 also includes a stem 847 which is disposed within a central flow passageway 842a and which, in a manner presently to be described, cooperates with a check valve 846 carried within an internal passageway 849 provided in coupling member 812 (FIG. 64). Stem 847 forms an integral part of the valve member 842 and terminates at an inboard end 847a (see also FIG. 65). Proximate the opposite end of stem 847 is an enlarged diameter portion 847b which terminates in the previously identified flange 841. Extending angularly through portion 847*b* are circumferentially spaced fluid passageways 850 which, in a manner presently to be described, permit fluid flowing past check valve 846 to enter chamber 824 via passageway 850*a*.

In operating the apparatus of this latest form of the invention, the vial closure end cap 851 and the cap which closes the socket or open end 809 of cylindrical portion 800 (not shown) are first removed. The open end of the drug vial assembly is then ready to be inserted into open end 809 of cylindrical portion 800. As the drug vial assembly is received within open end 809 of the infusion portion of the apparatus, threads 830 will move toward engagement with a first internal thread 834*a* provided within cylindrical portion 800. Rotation of the drug vial in a clockwise direction will cause the vial to advance within cylindrical portion 800 causing stem 847 to engage check valve 846. Because fluid under pressure within the reservoir resists movement of the check valve, operating valve 842 will move to the left. However, when flange 845 seats against internal shoulder 836*a* of plunger 836, continued clockwise rotation of vial 820 will cause stem 847 to move check valve 846 to the left into the open position shown in FIG. 64. With the check valve in this open position, distendable elastomeric membrane 430 will cause the fluid contained within chamber 832 to flow under pressure through port 858*a* into passageway 858, then into circumferentially spaced passageways 849, past the valve seat 862 and into fluid passageway 846*b* of the coupling member. The fluid will then flow into passageway 850 and then vigorously into mixing chamber 824 via a central fluid passageway 850*a* formed in the adding means. This flow of fluid under pressure into chamber 824 causes controlled flow of the first component, such as a diluent, through, around and about the adding means.

Referring particularly to FIG. 64, it is to be noted that so long as valve member 842 is in the position there shown, the mixed or dosed solution will continue to flow under pressure in a reverse direction through passageways 840, into passageways 868 formed in coupling member 812, and into annular passageway 870. From passageway 870 the fluid flows into passageway 87 formed in cylindrical portion 800 and thence toward the outlet port of the device for controlled delivery.

It is important to recognize that in the adding means of this form of the invention, affinity matrix supports can be provided that are capable of binding capacity at a level that enables highly efficient, biospecific attachment to the support of additives in substantial amounts. A substantial portion of the additives can subsequently be efficiently released immediately or, alternatively, over an extended period of time thereby permitting controlled infusion in a manner which is most therapeutically efficacious to a patient. Alternate disassociation reaction kinetics for desorption of the absorbed component from the affinity matrix can be established in a manner to critically determine the optimal conditions for elution over time of the bound additives. The appropriate elution diluent acts as the desorption agent to break the affinity attachment bond as a function of time. In this embodiment, by providing different drug vial assemblies with alternate extended drug release rates, a diluent flow rate can be established independent of the dosing rate, (disassociation, debonding or displacement of the additive from the activated substrate support). In this way selective dosing and flow rate opportunities can be optimized for individual patient physiology.

As indicated in FIG. 64, the adding means disposed within mixing chamber 824 is here provided in the form of a cylindrically shaped, functional support structure or scaffold to which various additives including beneficial agents, such as drugs, biologically active materials, and chemical elements and compounds can be releasably connected. These additives are carried by the structure in a manner such that, as the liquid flows through chamber 824 and circulates through the scaffold in the manner shown by the arrows in FIG. 64 the additives will be presented to the liquid flow and efficiently added over time to the liquid as it flows through the mixing chamber. Disposed on either side of scaffold 877 are glass flow distribution frits 879 (FIG. 65) which function to evenly distribute the fluid flow into and out of the chamber.

In addition to the additive presentation means previously discussed, a polymer can also be used as the carrier or support for the additive. Three classes of polymeric supports can be used, namely polymeric reagents, polymeric catalysts and polymeric substrates. A discussion of polymers as carriers or supports is contained in *Principles of Polymerization,* Second Edition by George Odian. Microporous polymers usable as carriers are also fully described in U.S. Pat. No. 4,519,909 issued to Castro.

The second component, such as a parenteral fluid, or elution agent which flows into chamber 824 can include, by way of example, a reagent, a solvent, a sterile diluent, various electrolytes, aqueous solutions such as aqueous solutions of dextrose, saline solutions, alkalinizing solutions, acidifying solutions, polar solutions and any other liquids that can serve as an appropriate vehicle for the administration of therapeutic or beneficial agents which are desirable to administer to the patient by infusion.

Turning now to FIG. 66, various other forms of adding means are there illustrated. For example, numeral 880 identifies an assembly comprising an insoluble, polystyrene porous substrate having an axially extending fluid passageway 881 and interconnecting voids 880*a* interstitially of which one or more additives are releasably carried. The selected additives such as elements, chemical compounds, drugs and functional intermediates are provided on or within the voids by techniques well known to those skilled in the art. The additives are, of course, introduced into the elution agent such as a sterile diluent as the diluent flows around, about and through substrate 880.

Another form of additive assembly designated in FIG. 66 by the numeral 882, comprises a plugged pore substrate having an internal, axially extending fluid passageway 883. The pores of this alternate sized substrate releasably carry the additives such as time released chemical compounds and beneficial agents, or medicaments.

Still another form of additive assembly is identified in FIG. 66 by the numeral 884. This assembly comprises a cylindrical, porous plug like member made up of a multiplicity of fused together microspheres or beads 884*a*, each of which is coated with a separation or reactive coating upon which is deposited an additive such as a biologically active material or other beneficial agent. The microspheres which embody internal crochannels can be formed of glass, plastic or other suitable materials.

The numeral 886 of FIG. 66 identifies yet another form of the adding means of the invention. In this form of the invention a generally cylindrically shaped functional support serves as an affinity attachment for attachment and subsequent release of the additive. Support 886 has an axial fluid passageway 887 and is formed from a multiplicity of microporous polymers presenting a multiplicity of reactive sites over a wide area for species immobilization.

The additive assembly designated in FIG. 66 by the numeral 888 comprises a solid tubular member having an axial fluid passageway 889. The exterior surface of the member is coated with a selected additive by any suitable means including interfacial polymerization means with the use of an interpolymer.

Alternatively, member 888 can be constructed of an ion exchange resin material to which the additive, such as a drug can be bound, to provide a drug-resin complex of a character that permits the drug to later be controllably released over time when exposed to an appropriate elution fluid.

Another slightly more complex additive assembly is identified by the numeral 890. This assembly is made up of a plurality of spaced apart, porous bung wafers 890a, 890b, 890c, and 890d, each wafer being of the same or different construction and porosity and each having reactive sites presenting to the liquid flow specially selected additives such as beneficial agents, elements or compounds so that multiple reactivities and selectivities can be achieved. With this construction, a wide variety of liquid flow rates, and complex sequential separations and priority staged substance introduction into the system output can be achieved by specially designing each of the wafers that cooperate to make up the structural support.

Still another form of activating assembly is designated in FIG. 66 by the numeral 892. This assembly comprises a cylindrically shaped structure made up of a plurality of elongated fibrous members 892a at least some of which are coated, pluged or impregnated with selected additives and, as necessary, functional intermediate materials.

The functional support member identified by the numeral 894 exemplifies yet another form of adding means of the invention. This member, which is also of a generally cylindrically shaped configuration, is constructed from a plurality of discrete layers such as polymer films 894a onto which selected additives and intermediate compounds have been removably affixed.

Functional support member 896 is constructed from a multiplicity of glass spaghetti-like strands 896a forming open cell, sponge-like construction, the cells of which are interconnected by tortious interstitial flow paths. Some or all of the open cells carry the selected additive or additives desired.

Functional support member 898 is constructed from a polymer foam which efficiently functions as the additive carrier.

It is to be understood that other forms of supports such as gells, biomosaic polymers and other porous forms of polymer reactive supports can be emplaced within mixing chamber 824 including joined azlactone-functional materials such as foams or polymer beads suitable for the attachment of functional materials.

Assemblies 880 through 898, which may be soluble or insoluble, hydrophillic or hydrophobic, are intended to merely exemplify, not to limit, the wide variety of materials and constructions that can be used to present the desired additives to the liquid flow introduced into the mixing chamber of the device.

As previously mentioned, the additives can be removably affixed to the scaffolds, matrices or functional support means in various ways including the process of chemical modification of the matrix. One important manner of removably affixing the additives enables the use of special separation techniques broadly defined by the term chromotography. Chromotography as used herein refers to a group of separation techniques which are characterized by a distribution of the molecules to be separated between two phases, one stationary and the other mobile. Affinity chromotography involves the use of biological interactions and contemplates the use of affinity chromotography supports through which the eluting fluid flows. In the present embodiment of the invention, the various additive presentation means, as described herein, can assume the character of an affinity chromotography support to which various ligands are attached. In the practice of affinity chromotography techniques, one of the members of the pair in the interaction, the ligand, is immobilized on a solid phase, while the other, the counterligand (most often a protein), is absorbed from the extract that is passing the substrate during the manufacturing process. Importantly, affinity chromotography techniques can include the use of highly versatile azlactone functional compounds, such as azlactone functional beads, as well as the use of a wide variety of other media for activation and coupling chemistry. Examples of ligands that can be attached to the affinity supports include antibodies, enzymes, lectins, nucleic acids hormones and vitamins. Examples of important counterligands include antigens, virus, cells, cell surface receptors and the like. Chromotography and affinity chromotography techniques are described in detail in Protein Purification by Janson and Ryden, Copyright 1989 and reference should be made to this work to provide a working understanding of the techniques.

Polymeric azlactones are well known in the prior art. Their use in the production of homopolymers and copolymers has been described in a number of patents. See for example, U.S. Pat. No. 3,488,327 (issued Jan. 6, 1970 to F. Kollinsky et al.); U.S. Pat. No. 3,583,950 (issued Jun. 8, 1971 to F. Kollinsky et al.); U.S. Pat. No. 4,304,705 (issued Dec. 8, 1981 to S. M. Heilmann et al.); and U.S. Pat. No. 4,737,560 (issued Apr. 12, 1988 to S. M. Heilmann et al.); and U.S. Pat. No. 5,013,795 issued May 7, 1991 to Coleman, et al.

Azlactones, or oxazolones, are cyclic anhydrides of N-acylamino acids and have been used extensively in organic synthesis. The formation of a five-membered azlactone of particularly useful functionality for immobilization purposes can be accomplished through the reaction of a carboxylate group with a-methyl alanine using a two-step process (See *Immobilized Affinity Techniques*-Hermanson, Mallia and Smith, Copyright 1992). One method of forming azlatone beads, the use of which has been previously mentioned herein, makes use of this process in the polymerization of monomers to first yield a carboxyl group on the matrix. In the second step, the azlactone ring is formed in anhydrous conditions through the use of a cyclization catalyst. Suitable cyclization agents that will drive this reaction include acetic anhydride, alkyl chloroformates, and carbondiimides. The process of forming these active groups and of making beaded polymeric supports containing them has been thoroughly described in patents assigned to 3M Corporation (U.S. Pat. No. 4,871,824 the tradename "Emphase". U.S. Pat. Nos. 5,045,615 and 5,013,795 which have been assigned to 3M Corporation also describe recent advances in this technology.

As pointed out in the 3M Corporation U.S. Pat. No. 4,737,560, azlactone-functional polymer beads are useful reactive supports for the attachment of functional materials to provide novel adduct beads. The adduct beads are useful as complexing agents, catalysts, reagents, and as enzyme or other proteinbearing supports. The term "support" or "affinity support" as used in this sense is usually understood to refer to a combination of (1) a ligand (usually of some known molecular configuration), that is firmly attached (e.g., immobilized), often by covalent means, and (2) a matrix (usually a solid insoluble substance). Azlactone support matrix materials and coupling chemistry is also of special interest because of its accessible matrix surface area and effective ligand density that can be attached to that surface.

U.S. Pat. No. 4,072,566 issued to Lynn on Feb. 7, 1978, and entitled "Immobilized Biologically Active Proteins" discloses a method of bonding enzymes or other biologically active proteins to an inorganic support material using p-phenylenediamine. The support materials disclosed as useful in the invention include siliceous materials, stannic oxide, titania, manganese dioxide, and zirconia.

The functional support structure 877 of the present embodiment of the invention can take on the character of an affinity support and is uniquely constructed to permit enzymes or other biologically active proteins to be bound thereto for later removal. This is accomplished by treating functional support 877 in the manner disclosed in the prior art patents identified in the preceding paragraphs with a compound having selected reactive functional groups such as azlactone functional compounds. In this way complexing agents, catalysts and biological materials such enzymes, proteins or other affinity absorbants, as well as biomacromolecules can be attached to the carrier for later removal and recovering.

When attaching certain biologically active proteins and other macro molecules, the use of spacer arms or leashes have been found to be very beneficial. Spacer arms or leashes are low-molecular-weight molecules that are used as intermediary linkers between a support material and an affinity ligand. Usually spacers consist of linear hydrocarbon chains with functionalities on both ends for each coupling to the support and ligand. First, one end of the spacer is attached chemically to the matrix using traditional immobilization chemistries; the other end is connected subsequently to the ligand using a secondary coupling procedure. The result is an immobilized ligand that sticks out from the matrix backbone by a distance equal to the length of the spacer arm chosen.

Figure 66B:
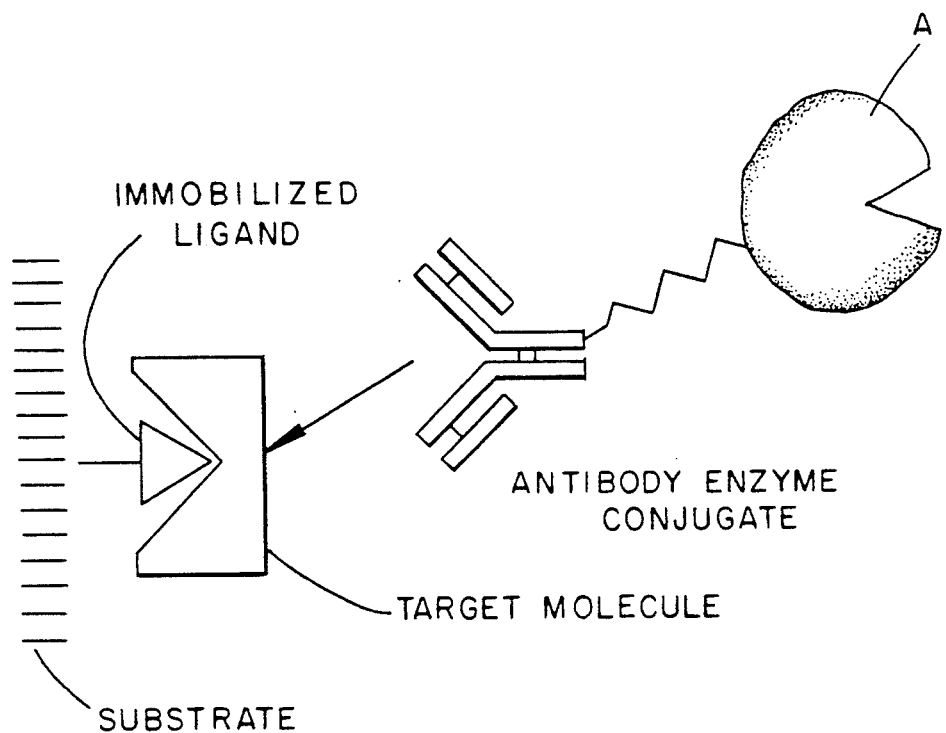

Referring to FIGS. 66A, 66B, 66C, and 66D, the use of spacer arms to attach proteins and enzymes to the substrate is there schematically illustrated. The principal advantage of using a spacer arm is that it provides ligand accessibility to the binding site of a target molecule. When the target molecule is a protein with a binding site somewhat beneath its outer surface, a spacer is essential to extend the ligand out far enough from the matrix to allow interaction. As indicated in FIG. 66A, when the ligand binding site S is buried or disposed in a pocket located just below the surface of the protein P, a ligand L that is either below the surface of the support material (upper portion) or a ligand L-1 that is attached directly to the surface (middle portion) cannot reach the level of the binding site S on an approaching protein molecule. The result may be weakened interaction or no binding at all. Accordingly, in these instances, spacer arm 899 is required to provide the ligand L-2 accessibility to the binding site of the protein molecule (lower portion of FIG. 66A). The details covering the use of spacer arms are fully set forth in Section 3.1.1 of the previously referred to work entitled Immobilized Affinity Ligand Techniques. This Section 3.1.1 is incorporated herein by reference.

Figure 66C:
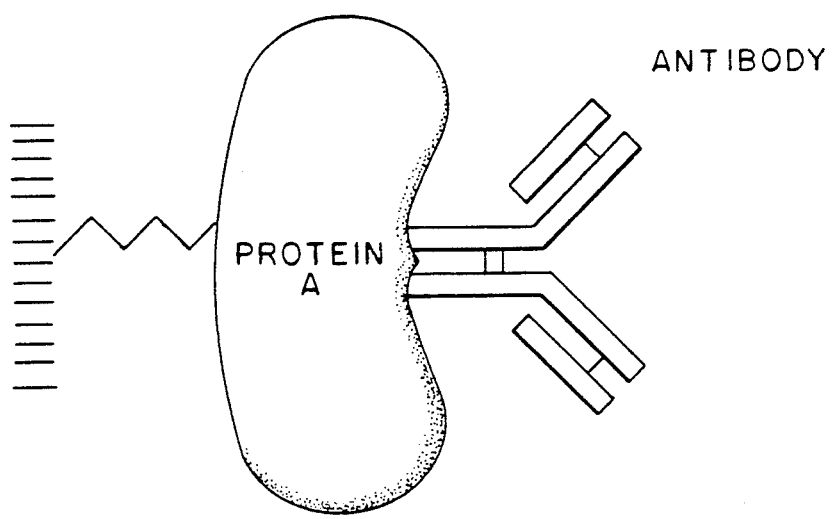
Figure 66D:
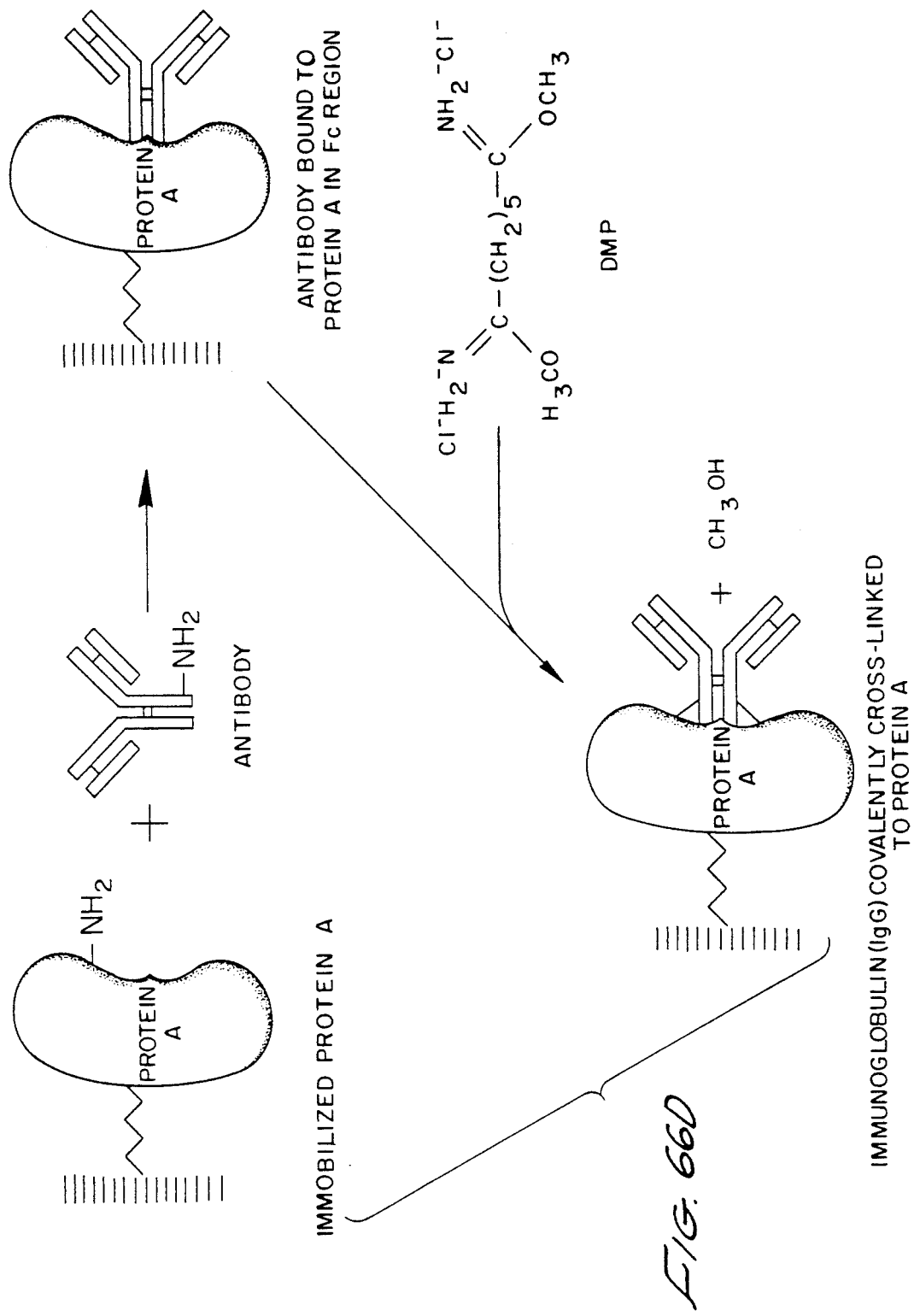

Turning now to FIGS. 66B, 66C, and 66D, it is to be noted that immobilized protein A can be used to immobilize an antibody molecule by taking advantage of the natural affinity of protein A for immunoglobulins. Incubation of a specific antibody with protein A matrix will bind the antibody in the Fc region, away from the antigen binding sites. Subsequent cross-linking of this complex with DMP (dimethyl pimelimidate) yields a covalently attached antibody with the antigen binding sites facing outward and free to interact with antigen.

With rigid support materials, a spacer molecule may also provide greater flexibility, allowing the immobilized ligand to move into position to establish the correct binding orientation with a protein. The degrees of freedom that a hydrocarbon extender can provide are much greater than the movement possible within the polymeric backbone of a matrix.

The choice of spacer molecule can affect the relative hydrophilicity of the immediate environment of an immobilized ligand. Molecules containing long hydrocarbon chains may increase the potential for nonspecific hydrophobic interactions, especially when the affinity ligand is small and of low molecular weight. Selecting spacers that have more polar constituents, such as secondary amines, amide linkages, ether groups or hydroxyls will help keep hydrophobic effects at a minimum.

It is also important to consider the ionic effects a spacer molecule may impart to a gel. Spacers with terminal primary amine groups should be completely coupled with ligand or blocked by a nonrelevant molecule (e.g., acetic anhydride; see Section 3.1.1.9 of *Immobilized Affinity Ligand Techniques*) to eliminate the potential for creating a positive charge on the support. With small ligands, these residual charges can form a secondary environment that may cause considerable nonspecific interactions with proteins. The same holds true for spacers with terminal carboxylic groups. In general, a negatively charged spacer will cause less nonspecific protein binding than a positively charged one, but blocking excess remaining groups is still a good idea. A good blocking agent for use with carboxylic residues is ethanolamine, which leaves a terminal hydroxyl group (See *Immobilized Affinity Ligand Techniques* for an expanded discussion of types of spacers and various immobilization and coupling protocols.)

As pointed out in *Protein Purification*, Janson and Ryden, Copyright 1989 which describes some alternate form of protein immobilization at Page 310:

> Ligand-protein interaction is often based on a combination of electrostatic, hydrophobic and hydrogen bonds. Agents which weaken such interactions might be expected to function as effective non-specific eluants.

This work provides further teaching of the techniques described herein.

The three important modes of chromatographic development applicable to the present invention, namely isocratic elution, gradient elution and displacement chromatography, are also discussed in the above-noted work.

Referring to FIGS. 67 through 70, another embodiment of the invention is shown. In this embodiment, the construction of the cylindrical housing portion 900 and the base assembly 901 are of similar construction to those of the last discussed embodiment and like numbers are used to designate like components. However, the latest form of the invention is unique in that the immobilized drug is contained in its own vial assembly 902 and the liquid component, or parenteral fluid, is contained in a separate assembly 904 that can be mated with the vial assembly and with the cylindrical housing portion to mix the drug with the liquid component and then to charge the reservoir by distending the energy source or distendable membrane 430 in a manner presently to be described in detail. Like the apparatus of the form of the invention just described, this embodiment also uniquely permits controlled intermixing of the first liquid component with the second component or additive such as a medicament or other beneficial agent which is presented to the first component by a unique additive presentation means, of the character defined in the preceding section of this specification.

Figure 67:
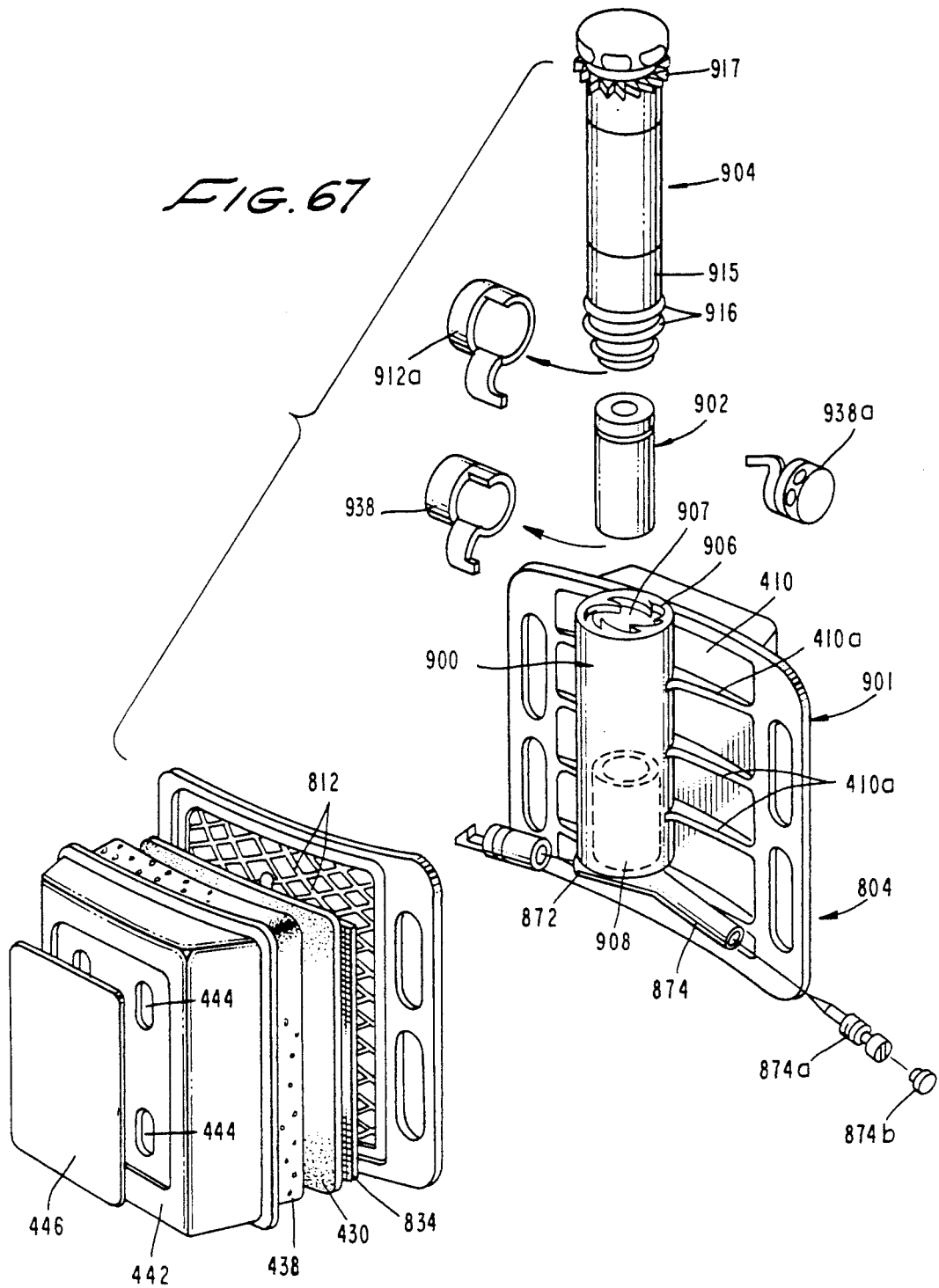
FIG. 67 is an enlarged, generally perspective exploded view of still another embodiment of the invention.

As best seen in FIG. 67, in this latest form of the invention, cylindrical portion 900 is integrally connected to the back or concave surface 410 of the base member by means of connector flanges 410a. Portion 900 also includes a transversely extending base wall 906 having a socket 907 within which assemblies 902 and 904 are supported in a manner best seen in FIGS. 68 and 69. Base portion 908 (FIG. 68) is provided with a longitudinally extending passageway 909 which communicates with storage reservoir 910 in the manner shown in FIG. 69. The outlet port of the device is in communication with reservoir 910 via passageway 872 which is of a dissimilar construction and arrangement to that previously described herein.

As seen in FIG. 67, a needle valve housing 874 of the character previously described extends angularly outwardly from back surface 410 (See also FIGS. 26 and 28). Needle valve 874a is carried by housing 874 and functions in the manner previously described, with cap 874b securing the adjustment end of the valve. It is to be noted that the front surface of the base member is also provided with crossing micro flow channels 812 which communicate with port 815 to which a filter membrane 834 is bonded. Filter means and micro-flow channels 812 function in the same manner to accomplish the same result as previously described herein.

Turning now particularly to FIGS. 68 and 69, the liquid vial assembly 904 comprises a vial 912 having a chamber 914 for containing the liquid component such as a diluent D. A plastic cover or overpackage 915 is closely received over vial 912. Cover 915 is provided with external threads 916 and system interlock stops 917 (FIG. 67). Threads 916 are adapted to mate with first and second sets of longitudinally spaced internal threads 918a and 918b provided on cylindrical housing portion 900. The manner of interconnection of the liquid vial and the housing will presently be discussed.

The open end of vial 912 is closed by a sealing member or stopper 920 which is provided with a centrally disposed, sealably interconnected blunt cannula 921 that provides communication between chamber 914, which contains the liquid component, or diluent D, and the exterior of the vial assembly. For a purpose that will presently become apparent, stopper 920 is movable within chamber 914 from a first position proximate the open end of the vial to a second position proximate the closed end. Prior to use, the open end of vial 912 and cannula 921 are sealed by a tear-off cap 912a of standard design (FIG. 67).

The drug vial assembly 902 includes a glass vial 922 having internal threads 923 and a chamber 924. Chamber 924 is sealed at one end by an elastomeric seal 925 that is held in place by a crimp cap 922a which fits closely over vial 922 (FIG. 68). The opposite, internally threaded end of chamber 924 is also sealed by an elastomeric sealing member 926 which is adapted to be pierced by a centrally disposed, blunt end cannula 927 that is carried by a check valve housing 930 disposed within a chamber 931 provided in base 908. Cannula 927 provides communication between chamber 924 and a fluid passageway 928 that extends through the check valve housing and communicates with reservoir 910 via passageway 909 when a check valve 932 is in an open position. Check valve 932 is guided by circumferentially spaced splines or ribs 912a. The operation of check valve 932 during the charging of reservoir 910 will presently be described.

Disposed proximate seals 925 and 926 are porous glass distribution frits 933 and 934 which function to properly control and distribute the elution diluent flowing through the adding means of the invention which is disposed intermediate the distribution frits. The adding means of the embodiment of the invention shown in FIGS. 68, and 69 is provided in the form of a cylindrically shaped, porous functional support structure 937 which is carried within chamber 924 and to which various additives including beneficial agents such as drugs, biologically active materials and chemical elements and compounds can be releasably connected in the manner previously described herein. These additives are carried by the structure in a manner such that, as the liquid flows through chamber 924 and circulates around, about and through the support assembly the additives will efficiently removed from the support and mixed with the liquid. It is to be understood that the adding means disposed within chamber 924 can be of the general character of any one, or a combination of, those previously described herein and illustrated in FIG. 66.

In operating the apparatus of this latest form of the invention, the sterile vial closure caps 938 and 938a, which are provided the ends of the vial 922 as well as a sterile closure cap which closes the open end of cylindrical portion 900 are first removed and discarded. As the drug vial assembly is received within open end 907 of portion 900, threads 923 will move toward engagement with threads 930a provided on housing body 908. Rotation of the drug vial in a clockwise direction will cause the vial to advance within cylindrical portion 900 causing cannula 927 to pierce elastomeric sealing member 926. After the drug vial assembly is fully seated, scalloped cap 938a, which is used to rotate the vial, is removed and discarded.

With the drug vial assembly in place within cylindrical portion 900, the open end of liquid vial assembly 904 is inserted into an annular space 900a and threads 916 provided on cover or overpackage 915 are mated with internal threads 918a provided proximate the mouth of cylindrical portion 900. Rotation of assembly 904 will cause cannula 921 to pierce drug vial sealing member 925 in the manner shown in FIG. 69 thereby opening fluid communication between chamber 914 of the diluent vial assembly and chamber 924 of the drug vial assembly.

Continued rotation of the diluent vial assembly will cause threads 916 to move into an open annular space 942 thereby permitting the vial assembly to be forcibly pushed to the right from the position shown in FIG. 68 to the position shown in FIG. 69. This movement causes elastomeric member 920 to move to the left within chamber 914 thereby forcing the diluent D through cannula 921 and into the drug vial assembly under substantial pressure. The elution diluent will flow through glass frit 933 and then forcibly around, about and through support structure 937 of the adding means. The diluent flowing through glass frit 934 and into cannula 927 under pressure will cause check valve member 932 to move to the right into the open position shown in FIG. 69 thereby permitting the fluid mixture to flow toward the reservoir 910 via passageway 909. This fluid mixture flowing toward the reservoir will cause distendable membrane 430 to distend outwardly into the position shown in FIG. 69. In its distended configuration, membrane 430 provides the energy source for controllably expelling the fluid mixture from the device in the manner previously described.

Once the reservoir is charged, and the diluent vial assembly has moved into engagement with the second set of threads 918b, continued rotation of the assembly will cause threads 912a on the overpackage to engage threads 918b and securely lock the vial and drug assemblage in position within cylindrical portion 900 pending infusion of the beneficial agent into the patient.

Turning to FIGS. 71 through 75, still another embodiment of the invention is shown. In this embodiment, the construction of the cylindrical housing portion 950 and the base assembly 951 are once again of similar construction to those last discussed and like numbers are used to designate like components. However, the latest form of the invention is different from the embodiment just described in that while the immobilized drug is contained in its own vial assembly 952 and a first portion of the liquid component, or parenteral fluid, is contained in a separate assembly 954, the reservoir is prefilled with a second portion of the liquid component.

As before, vial assembly 954 can be mated with vial assembly 952 and with the cylindrical housing to mix the drug with the liquid component. With the unique construction of this last form of the invention, the liquid already within the prefilled reservoir can be controllably intermixed with the fluid within assembly 954 and with the addititive contained within assembly 952 to form an infusible mixture which can be later discharged by the energy source or distendable membrane 430 of the invention. Stated another way, like the apparatus of the form of the invention just described, this embodiment permits controlled intermixing of the portion of the first liquid component or carrier component, contained within vial 954 with the second component or additive contained within vial 952 to produce a first mixture. This mixture of the carrier liquid and the additive can then be introduced into the reservoir which has been previously filled with a diluent or other liquid to produce a second, injectable mixture for later infusion into a patient.

Figure 75:
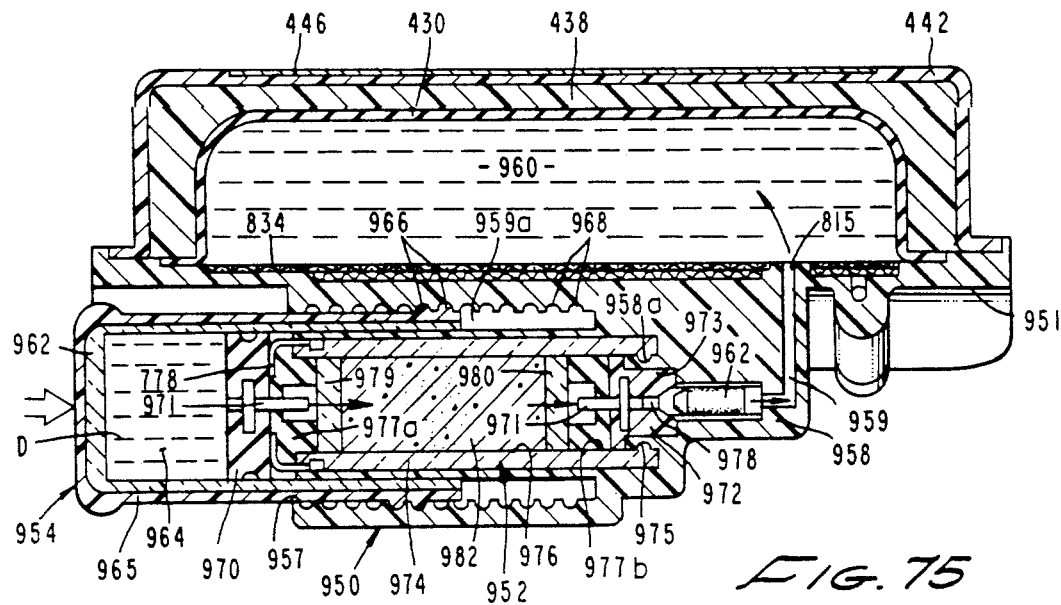
FIG. 75 is an enlarged cross-sectional view of the embodiment shown in FIG. 71 as it appears in an assembled configuration.

As best seen in FIGS. 71 and 75, in this latest form of the invention cylindrical portion 950 is integrally connected to the back or concave surface 410 of the base member by means of connector flanges 410a. Portion 950 also includes a base wall 956 having a socket 957 which receives assemblies 952 and 954 in a manner illustrated in FIG. 75. As best seen in FIG. 75, base 958 is provided with a passageway 959 which communicates with storage reservoir 960. The outlet port of the device is in communication with reservoir 960 via passageway 872 which is of similar construction and arrangement as previously described herein.

Similarly, a needle valve housing 874 of the character previously described which houses a needle valve assembly 874a extends angularly outwardly from back surface 410 (See also FIGS. 26 and 28). Valve 874a comprises the second flow control means of the invention for controlling fluid flow outwardly of the device. It is to be noted that the front surface of the base member is also provided with crossing micro flow channels 812 which communicate with port 815 to which a filter membrane 834 is bonded. Filter means and micro-flow channels 812 function in the same manner to accomplish the same result as previously described herein.

Figure 73:
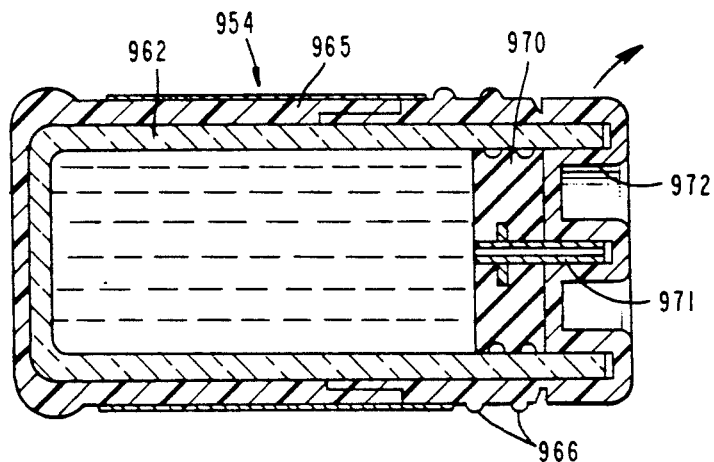
FIG. 73 is a cross-sectional view taken along lines 73—73 of FIG. 72.

Turning now particularly to FIG. 73, the liquid vial assembly 954 comprises a vial 962 having a chamber 964 for containing the carrier liquid component such as a diluent. A two-part plastic cover or overpackage 965 is closely received over vial 962. Cover 965 is provided with external threads 966 which are adapted to mate with the coupling means of the invention shown here as internal threads 968 provided on cylindrical housing portion 950 (FIG. 75). The manner of interconnection of the liquid vial and the housing will presently be discussed.

The open end of vial 962 is closed by a sealing member or stopper 970 which is provided with a centrally disposed, sealably interconnected blunt cannula 971. Cannula 971 provides communication between chamber 964, which contains the carrier liquid component, and the exterior of the vial assembly. For a purpose that will presently become apparent, stopper 970 is movable longitudinally of chamber 964 from a first position proximate the open end of the vial to a second position proximate the closed end. Prior to use, the open end of vial 962 and cannula 971 are substantially sealed by a tear-off cap 972 of standard design.

Figure 74:
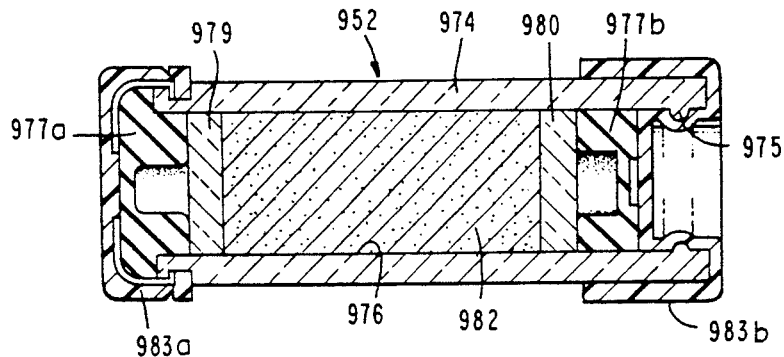
FIG. 74 is an enlarged cross-sectional view of the drug vial of the apparatus prior to being inserted into the coupling assembly of the apparatus.

Turning now to FIG. 74, the drug vial assembly 952 includes a glass vial 974 having internal threads 975 and a chamber 976. Chamber 976 is sealed at one end by an elastomeric seal 977a that is held in place by a crimp cap 778 which fits closely over vial 974. The opposite, internally threaded end of chamber 976 is also sealed by an elastomeric sealing member 977b which is adapted to be pierced by a centrally disposed blunt cannula 971 that is carried by a check valve housing 972 disposed within a chamber 973 provided in base 958. Cannula 971 provides communication between chamber 976 and a fluid passageway 978 that extends through the check valve housing and communicates with reservoir 960 via passageway 959 when a check valve 962 is in an open position. The operation of check valve 962 during the fluid mixture transfer reservoir 960 will presently be described, Disposed proximate seals 977a and 977b are porous glass distribution frits 979 and 980 which function, as before, to properly control and distribute the liquid flowing through the chamber containing the adding means of the invention which is disposed intermediate the distribution frits. The adding means of the embodiment of the invention shown in FIGS. 74 and 75 is provided in the form of a cylindrically shaped porous scaffold 982 which is carried within chamber 976 and to which any one or a combination of the various additives previously described herein can be releasably connected. As before, these additives are carried by the scaffold matrix in a manner such that, as the liquid flows through chamber 976 and circulates around, about and through the scaffold in the manner previously discussed herein the additive will be released from the scaffold and thoroughly intermixed with the liquid. It is to be understood that the adding means disposed within chamber 976 can be of the general character of any one of those previously described herein and illustrated in FIGS. 66 and 67.

In operating the apparatus of this latest form of the invention, the sterile vial closure caps 972 and 983b which close the ends of the vials 962 and 974 as well as a sterile closure cap which closes the open end of cylindrical portion 950 are first removed and discarded. As the drug vial assembly is received within open end 957 of portion 950, threads 975 will move toward engagement with threads 958a provided in base 958 proximate check valve housing 972. Rotation of the drug vial in a clockwise direction will cause the vial to advance within cylindrical portion 950 causing blunt end cannula 971 to pierce elastomeric sealing member 977b.

With the drug vial assembly in place within cylindrical portion 950, cap 983a is removed and the open end of liquid vial assembly 954 is inserted into annular space 958a. Next, threads 966 provided on cover or overpackage 965 are mated with internal threads 968 provided proximate the mouth of cylindrical portion 950. Rotation of assembly 954 will cause cannula 971 to pierce drug vial sealing member 977a thereby opening fluid communication between chamber 964 of the liquid carrier diluent vial assembly and chamber 976 of the drug vial assembly.

Continued rotation of the liquid carrier vial assembly will cause it to move to the right as viewed in FIG. 75. This causes movement of elastomeric member 970 to the left within chamber 964 thereby forcing the carrier liquid diluent D through cannula 971 into the drug vial assembly under substantial pressure. The diluent will flow through glass frit 979 and then forcibly around, about and through scaffold matricies 982 of the adding means. The elution diluent flowing under pressure through glass frit 980 and into cannula 971 will cause check valve member 962 to move to the right into the open position shown in FIG. 75 permitting the fluid mixture to flow toward the reservoir 960 via passageway 959. This fluid mixture flowing toward the reservoir will controllably intermix with the liquid component contained within the prefilled reservoir to form the infusible liquid mixture. In its distended configuration, elastomeric membrane 430 provides the energy source for controllably expelling the infusible mixture from the device in the manner previously described.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for use in infusing fluids into a patient at a controlled rate, said apparatus comprising:
   (a) a container assembly including:
      (i) a container having a fluid flow passageway and walls defining an internal chamber in communication with said fluid passageway;
      (ii) adding means disposed within said chamber for adding an additive to fluid flowing through said chamber, said adding means comprising an additive and an additive presentation means for presenting said additive to the fluid; and
   (b) an infusion device comprising a housing having first and second portions, said first portion including coupling means for coupling said container assembly with said first portion of said housing, said coupling means having a first passageway adapted to communicate with said fluid flow passageway of said container, said second portion of said housing comprising:
      (i) a base having a fluid outlet and first and second fluid passageways formed therein, said first passageway being in communication with said first passageway of said coupling means and said second passageway being in communication with said fluid outlet; and p2 (ii) a thin, generally planar distendable membrane constructed of an elastic material, said membrane overlying and cooperating with said base to define a reservoir for containing a fluid, said reservoir being in communication with said first and second passageways of said base, said membrane being distendable by fluid introduced into said chamber under pressure and having a tendency to return to a substantially less distended configuration, whereby the fluid contained within said reservoir will be urged to flow selectively into said first and second passageways of said base.

2. A device as defined in claim 1 in which said additive comprise a beneficial agent which is removable from said additive presentation means using affinity chromotography techniques.

3. A device as defined in claim 1 in which said additive is removably connected to said additive presentation means using azlactone functional compounds.

4. A device as defined in claim 1 in which said additive presentation means comprises a structural support disposed within said container, said structural support having biologically active proteins bound thereto.

5. An apparatus as defined in claim 1 in which said container assembly further includes first flow control means for controlling the flow of fluid through said fluid flow passageway of said container.

6. An apparatus as defined in claim 5 in which said container includes second flow control means for controlling the flow of fluid through said fluid outlet of said base.

7. An apparatus as defined in claim 6 in which said coupling means further includes operating means for operating said first flow control means.

8. An apparatus as defined in claim 6 in which said base further includes an inlet port in communication with said reservoir.

9. A mixing apparatus comprising:
   (a) a container assembly including:
      (i) a first container having a fluid flow passageway and walls defining an internal chamber in communication with said fluid flow passageway;

(ii) adding means disposed within said chamber for adding an additive to fluid flowing through said chamber, said adding means comprising an additive and an additive presentation means for presenting said additive to the fluid;

(b) a dispensing device comprising a housing having an outlet port and first and second portions, said first portion including:

(i) coupling means for coupling said container assembly with said first portion of said housing, said coupling means having a first passageway adapted to communicate with said fluid flow passageway of said first container;

(ii) flow control means for controlling the flow of fluid through said first passageway;

said second portion comprising:

(i) a base having first and second fluid passageways formed therein, said first passageway being in communication with said first passageway of said coupling means and said second passageway being in communication with said fluid outlet;

(ii) a thin, generally planar distendable membrane constructed of an elastic material, said membrane overlaying and cooperating with said base to define a reservoir for containing a fluid, said reservoir being in communication with said first and second passageways of said base, said membrane being distendable by fluid introduced into said chamber under pressure and having a tendency to return to a substantially less distended configuration, whereby the fluid contained within said reservoir will be urged to flow into said first and second passageways of said base.

10. An apparatus as defined in claim 9 in which said container assembly further comprises a second container having a chamber containing a liquid, said second container being adapted to be coupled with said first container.

11. An apparatus as defined in claim 10 in which said fluid flow passageway of said first container includes an inlet and an outlet and in which said coupling means includes a cannula disposed in communication with said first passageway of said base and in which said outlet of said fluid flow passageway of said first container is closed by a first sealing member pierceable by said cannula upon coupling said container assembly with said first portion of said housing.

12. An apparatus as defined in claim 11 in which said inlet of said fluid flow passageway of said first container is closed by a second sealing member and in which said second container includes a sealing assembly movable within said chamber thereof, said sealing assembly including a cannula adapted to pierce said second sealing member of said first container to permit fluid flow between said chamber of said second container and said fluid flow passageway of said first container via said cannula.

13. An apparatus as defined in claim 11 in which said liquid in said chamber of said Second container comprises a diluent.

14. An apparatus as defined in claim 13 in which said additive comprises a medicament.

15. An apparatus as defined in claim 13 in which said additive comprises a beneficial agent.

16. An apparatus as defined in claim 15 in which said adding means comprises an additive which provides for extended release of a beneficial agent to the fluid over time.

17. An apparatus as defined in claim 15 in which said additive presentation means provides for extended release of said additive over time.

18. A mixing and delivery apparatus comprising:

(a) a container assembly including:

(i) a container having a fluid flow passageway and walls defining an internal chamber in communication with said fluid passageway;

(ii) adding means disposed within said chamber for adding an additive to fluid flowing through said fluid flow passageway into said chamber, said adding means comprising an additive and an additive presentation means being disposed within said chamber in the path of fluid flowing into said chamber through said fluid flow passageway; and (b) a delivery device comprising a housing having first and second portions, said first portion including coupling means for coupling said container assembly with said first portion of said housing, said coupling means having a first passageway adapted to communicate with said fluid flow passageway of said container, said second portion of said housing comprising:

(i) a base having a fluid outlet and first and second fluid passageways formed therein, said first passageway being in communication with said first passageway of said coupling means and said second passageway being in communication with said fluid outlet; and (ii) a thin, generally planar distendable membrane constructed of an elastic material, said membrane overlaying and cooperating with said base to define a reservoir for containing a fluid said reservoir being in communication with said first and second passageways of said base, said membrane being distendable by fluid introduced into said chamber under pressure and having a tendency to return to a substantially less distended configuration, whereby the fluid contained within said reservoir will be urged to flow selectively into said first and second passageways of said base.

19. An apparatus as defined in claim 18 in which said additive comprise a biologically active material.

20. An apparatus as defined in claim 18 in which said adding means comprises a polymer.

21. An apparatus as defined in claim 18 in which said additive presentation means comprises a scaffold disposed within said container and adapted to releasably carry said additive.

22. An apparatus as defined in claim 18 in which said additive is substantially removable from said additive presentation means using affinity chromotography techniques.

23. An apparatus as defined in claim 22 in which a ligand is connected to said support and a target molecule is connected to said ligand.

24. An apparatus as defined in claim 23 in which a spacer arm is connected to said Support and in which a ligand is connected to said spacer arm.

25. An apparatus as defined in claim 24 in which an enzyme is connected to said target. molecule.

26. An apparatus as defined in claim 24 in which target molecule is a protein.

27. An apparatus as defined in claim 26 in which an antibody is connected to said protein.

28. An apparatus as defined in claim 26 in which a immunoglobulin is connected to said protein.

29. An apparatus as defined in claim 26 in which an antibody is covalently attached to said protein, said antibody having binding sites facing outwardly from said protein.

30. An apparatus as defined in claim 29 in which an antibody enzyme conjugte is applied that has specificity for the bound target molecule.

* * * * *